(12) United States Patent
Kanavarioti

(10) Patent No.: US 11,884,968 B2
(45) Date of Patent: Jan. 30, 2024

(54) OSMIUM TAGGED PROBES FOR NUCLEIC ACID DETECTION

(71) Applicant: Anastassia Kanavarioti, El Dorado Hills, CA (US)

(72) Inventor: Anastassia Kanavarioti, El Dorado Hills, CA (US)

(*) Notice: Subject to any disclaimer, the term of this patent is extended or adjusted under 35 U.S.C. 154(b) by 0 days.

(21) Appl. No.: 17/897,743

(22) Filed: Aug. 29, 2022

(65) Prior Publication Data

US 2023/0203569 A1 Jun. 29, 2023

Related U.S. Application Data

(60) Continuation of application No. 17/466,931, filed on Sep. 3, 2021, now Pat. No. 11,427,859, which is a division of application No. 17/063,245, filed on Oct. 5, 2020, now Pat. No. 11,111,527.

(51) Int. Cl.
| | |
|---|---|
| *C12Q 1/68* | (2018.01) |
| *C07H 21/00* | (2006.01) |
| *C12Q 1/6832* | (2018.01) |
| *C12Q 1/6825* | (2018.01) |

(52) U.S. Cl.
CPC .......... *C12Q 1/6832* (2013.01); *C07H 21/00* (2013.01); *C12Q 1/6825* (2013.01)

(58) Field of Classification Search
CPC ..... C12Q 1/6832; C12Q 1/6825; C07H 21/00
See application file for complete search history.

(56) References Cited

U.S. PATENT DOCUMENTS

| | | |
|---|---|---|
| 2014/0228247 A1 | 8/2014 | Flechsig et al. |
| 2017/0137457 A1 | 5/2017 | Kanavarioti |
| 2019/0055592 A1 | 2/2019 | Morin et al. |

OTHER PUBLICATIONS

"Nanopore Protocol: Direct RNA Sequencing Control Experiment (SQK-RNA002)", Oxford Nanopore Technologies, Aug. 2019, 2 pages.
Aggarwal et al., "Emergence of Circulating MicroRNAs in Breast Cancer as Diagnostic and Therapeutic Efficacy Biomarkers", Molecular Diagnosis & Therapy, 2020, pp. 153-173, vol. 24, No. 2.
Alles et al., "An Estimate of the Total Numbers of True Human miRNAs", Nucleic Acids Research, 2019, pp. 3353-3364, vol. 47, No. 7.
Ambros, "MicroRNAs: Tiny Regulators with Great Potential", Cell, Dec. 28, 2001, pp. 823-826, vol. 107.
Arata et al., "Rapid Sub-Attomole MicroRNA Detection on a Portable Microfluidic Chip", Analytical Sciences, Jan. 2014, pp. 129-135, vol. 30.
Bartel, "MicroRNAs: Genomics, Biogenesis, Mechanism, and Function", Cell, Jan. 23, 2004, pp. 281-297, vol. 116.
Bronkhorst et al., "Early Detection of Cancer Using Circulating Tumor DNA: Biological, Physiological and Analytical Considerations", Critical Reviews in Clinical Laboratory Sciences, 2019, pp. 1-17.
Butler et al., "Ionic Current Blockades from DNA and RNA Molecules in the ?-Hemolysin Nanopore", Biophysical Journal, Nov. 2007, pp. 3229-3240, vol. 93, No. 9.
Cao et al., "Single-Molecule Sensing of Peptides and Nucleic Acids by Engineered Aerolysin Nanopores", Nature Communications, 2019, pp. 1-11, vol. 10, No. 4918.
Cao et al., "Structure of the Nonameric Bacterial Amyloid Secretion Channel", Proceedings of the National Academy of Sciences of the United States of America, 2014, pp. E5439-E5444.
Chang et al., "Osmium-Labeled Polynucleotides. The Reaction of Osmium Tetroxide with Deoxyribonucleic Acids and Synthetic Polynucleotides in the Presence of Tertiary Nitrogen Donor Ligands", Biochemistry, 1977, pp. 33-38, vol. 16, No. 1.
Chaudhary et al., "Nanotechnology Based Approaches for Detection and Delivery of MicroRNA in Healthcare and Crop Protection", Journal of Nanobiotechnology, 2018, pp. 1-18, vol. 16, No. 40.
Chen et al., "Nanotechnology Strategies for the Analysis of Circulating Tumor DNA: A Review", Medical Science Monitor, 2020, pp. e921040-1-e921040-9, vol. 26.
Debnath et al., "Osmium Tag for Post-Transcriptionally Modified RNA", ChemBioChem, 2018, pp. 1653-1656, vol. 19.
Ding et al., "Single Pyrimidine Discrimination During Voltage-Driven Translocation of Osmylated Oligodeoxynucleotides via the ?-Hemolysin Nanopore", Beilstein Journal of Nanotechnology, 2016, pp. 91-101, vol. 7.
Farazi et al. "MicroRNAs in Human Cancer", Advances in Experimental Medicine and Biology, 2013, pp. 1-20, vol. 774.
Ferracin et al., "Quantification of Circulating MicroRNAs by Droplet Digital PCR", Methods in Molecular Biology, 2018, pp. 445-457, vol. 1768.
Finotti et al., "Liquid Biopsy and PCR-free Ultrasensitive Detection Systems in Oncology (Review)", International Journal of Oncology, 2018, pp. 1395-1434, vol. 53, No. 4.
Fojta et al., "Multiply Osmium-Labeled Reporter Probes for Electrochemical DNA Hybridization Assays: Detection of Trinucleotide Repeats", Biosensors and Bioelectronics, 2004, pp. 985-994, vol. 20, No. 5.
Fulci et al., "Quantitative Technologies Establish a Novel MicroRNA Profile of Chronic Lymphocytic Leukemia", Blood, Jun. 2007, pp. 4944-4951, vol. 109, No. 11.

(Continued)

*Primary Examiner* — Jezia Riley
(74) *Attorney, Agent, or Firm* — Thompson Coburn LLP; William A. Holtz

(57) ABSTRACT

Provided for herein is a method for detecting the presence of a nucleic acid target molecule in a biological sample. In certain aspects, the method comprises contacting a test sample that comprises (i) a biological sample comprising a nucleic acid target molecule and (ii) an osmylated single-stranded oligonucleotide probe comprising at least one pyrimidine residue covalently bonded to a substituted or unsubstituted Osmium tetroxide $(OsO_4)$-2,2'-bypyridine group (OsBp group).

Figure 1A:
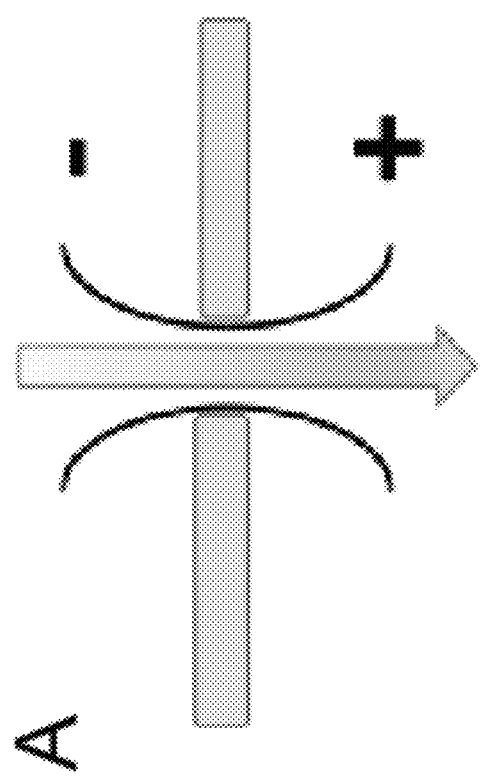

20 Claims, 48 Drawing Sheets
Specification includes a Sequence Listing.

(56) References Cited

OTHER PUBLICATIONS

Fuller et al., "Real-Time Single-Molecule Electronic DNA Sequencing by Synthesis Using Polymer-Tagged Nucleotides on a Nanopore Array", Proceedings of the National Academy of Sciences of the United States of America, May 2016, pp. 5233-5238, vol. 113, No. 19.
Galenkamp et al., "Direct Electrical Quantification of Glucose and Asparagine from Bodily Fluids Using Nanopores", Nature Communications, 2018, pp. 1-8, vol. 9, No. 4085.
Gene Characterization Kits, Stratagene Catalog, 1988, p. 39.
Giannopoulou et al., "Liquid Biopsy in Ovarian Cancer: Recent Advances on Circulating Tumor Cells and Circulating Tumor DNA", Clinical Chemistry and Laboratory Medicine, 2017, pp. 186-197, vol. 56, No. 2.
Gines et al., "Emerging Isothermal Amplification Technologies for MicroRNA Biosensing: Applications to Liquid Biopsies", Molecular Aspects of Medicine, Apr. 2020, pp. 1-9, vol. 72, Article 100832.
Gu et al., "Nanopore Single-Molecule Detection of Circulating MicroRNAs", Methods in Molecular Biology, 2013, pp. 255-268, vol. 1024.
Haque et al., "Solid-State and Biological Nanopore for Real-time Sensing of Single Chemical and Sequencing of DNA", Nano Today, 2013, pp. 56-74, vol. 8.
Henley et al., "Osmium-Based Pyrimidine Contrast Tags for Enhanced Nanopore-Based DNA Base Discrimination", PLOS One, 2015, pp. 1-12, vol. 10, No. 12.
Huang et al., "Electro-Osmotic Capture and Ionic Discrimination of Peptide and Protein Biomarkers with FraC Nanopores", Nature Communications, 2017, pp. 1-11, vol. 8, No. 935.
International Search Report and Written Opinion for PCT/US2020/054271 dated Mar. 1, 2021.
Kanavarioti et al., "Capillary Electrophoretic Separation-Based Approach to Determine the Labeling Kinetics of Oligodeoxynucleotides", Electrophoresis, 2012, pp. 3529-3543, vol. 33.
Kanavarioti et al., "Extract OsBp Translocation Events from ONT bulk FAST5", See RNA(OsBp) Event Detection Python Package in a public repository, 3 pages, accessed on Oct. 4, 2020, retrieved from https://github.com/kangaroo96/osbp_detect <https://protect-us.mimecast.com/s/7efCCxklovc1grrAC84NfPd> on Feb. 17, 2021.
Kanavarioti et al., "OsBp Detection: Installation Instructions for MacOS", 2 pages, accessed on Oct. 4, 2020, retrieved from https://github.com/kangaroo96/osbp_detect <https://protect-us.mimecast.com/s/7efCCxklovc1grrAC84NfPd>/blob/master/instructions.md on Feb. 17, 2021.
Kanavarioti, "False Positives and False Negatives Measure Less Than 0.001% in Labeling ssDNA with Osmium Tetroxide 2,2'-Bipyridine", Beilstein Journal of Nanotechnology, 2016, pp. 1434-1446, vol. 7.
Kanavarioti, "HPLC Methods for Purity Evaluation of Man-Made Single-Stranded RNAs", Scientific Reports, 2019, pp. 1-13, vol. 9, No. 1019.
Kanavarioti, "Osmylated DNA, a Novel Concept for Sequencing DNA Using Nanopores", Nanotechnology, 2015, 11 pages, vol. 26.
Kao et al., "Urine miR-21-5p as a Potential Non-Invasive Biomarker for Gastric Cancer", Oncotarget, 2017, pp. 56389-56397, vol. 8, No. 34.
Karlin et al., "Applications and Statistics for Multiple High-Scoring Segments in Molecular Sequences", Proceedings of the National Academy of Sciences of the United States of America, Jun. 1993, pp. 5873-5877, vol. 90.
Kasianowicz et al., "Characterization of Individual Polynucleotide Molecules Using a Membrane Channel", Proceedings of the National Academy of Sciences of the United States of America, Nov. 1996, pp. 13770-13773, vol. 93.
Kim et al., "Transfer RNA-Derived Small RNAs: Another Layer of Gene Regulation and Novel Targets for Disease Therapeutics", Molecular Therapy, Nov. 2020, pp. 1-18, vol. 28, No. 11.

Kwapisz, "The First Liquid Biopsy Test Approved. Is it a New Era of Mutation Testing for Non-Small Cell Lung Cancer?", Annals of Translational Medicine, 2017, pp. 1-7, vol. 5, No. 3.
Lai et al., "MicroRNA-21 in Glomerular Injury", Journal of the American Society of Nephrology, 2014, pp. 805-816, vol. 26.
Laszlo et al., "Decoding Long Nanopore Sequencing Reads of Natural DNA", Nature Biotechnology, 2014, pp. 829-833, vol. 32.
Li et al., "Elevated Plasma miRNA-122, -140-3p, -720, -2861, and -3149 During Early Period of Acute Coronary Syndrome are Derived from Peripheral Blood Mononuclear Cells", PLoS ONE, 2017, pp. 1-14, vol. 12.
Maglia et al., "Analysis of Single Nucleic Acid Molecules with Protein Nanopores", Methods in Enzymology, 2010, pp. 591-623, vol. 475.
Majilessi et al., "Advantages of 2?-O-methyl Oligoribonucleotide Probes for Detecting RNA Targets", Nucleic Acids Research, 1998, pp. 2224-2229, vol. 26, No. 9.
Mall et al. "Stability of miRNA in Human Urine Supports its Biomarker Potential", Biomarkers in Medicine, 2013, pp. 623-631, vol. 7, No. 4.
Meseure et al., "Long Noncoding RNAs as New Architects in Cancer Epigenetics, Prognostic Biomarkers, and Potential Therapeutic Targets", Biomed Research International, 2015, 14 pages, vol. 2015.
Mitchell et al., "Circulating MicroRNAs as Stable Blood-Based Markers for Cancer Detection", Proceedings of the National Academy of Sciences of the United States of America, 2008, pp. 10513-10518, vol. 105, No. 30.
Oellerich et al., Circulating Cell-Free DNA-mDiagnostic and Prognostic Applications in Personalized Cancer Therapy, Therapeutic Drug Monitoring, Apr. 2019, pp. 115-120, vol. 41, No. 2.
Palecek, "Probing DNA Structure with Osmium Tetroxide Complexes in vitro", Methods in Enzymology, 1992, pp. 139-155, vol. 212.
Pogribny, "MicroRNAs as Biomarkers for Clinical Studies", Experimental Biology and Medicine, 2017, pp. 1-8.
Poller et al., "Non-Coding RNAs in Cardiovascular Diseases: Diagnostic and Therapeutic Perspectives", European Heart Journal, 2017, pp. 1-20.
Pös et al., "Circulating Cell-Free Nucleic Acids: Characteristics and Applications", European Journal of Human Genetics, 2018, pp. 937-945, vol. 26, No. 7.
Raabe et al., "Biases in Small RNA Deep Sequencing Data", Nucleic Acids Research, 2014, pp. 1414-1426, vol. 42, No. 3.
Reske et al., "Kinetics of the Labeling Reactions of Thymidine, Cytosine and Uracil with Osmium Tetroxide Bipyridine", Microchim Acta, 2009, pp. 197-201, vol. 166.
Rupaimoole et al., "MicroRNA Therapeutics: Towards a New Era for the Management of Cancer and Other Diseases", Nature Reviews, 2017, pp. 203-222, vol. 6.
Satyal et al., "Urine Biopsy—Liquid Gold for Molecular Detection and Surveillance of Bladder Cancer", Frontiers in Oncology, Nov. 2019, pp. 1-9, vol. 9, No. 1266.
Stewart et al., "Circulating Cell-Free DNA for Non-Invasive Cancer Management", Cancer Genetics, Dec. 2018, pp. 169-179, vol. 228.
Sultan et al., "Nanopore Device-Based Fingerprinting of RNA Oligos and MicroRNAs Enhanced with an Osmium Tag", Scientific Reports, 2019, pp. 1-18, vol. 9, No. 14180.
Thum et al., "MicroRNA-21 Contributes to Myocardial Disease by Stimulating MAP Kinase Signalling in Fibroblasts", Nature, 2008, pp. 980-984, vol. 456.
Tian et al., "Designing a Polycationic Probe for Simultaneous Enrichment and Detection of MicroRNAs in a Nanopore", ACS Nano, 2013, pp. 3962-3969, vol. 7, No. 5.
Tian et al., "Polycationic Probe-Guided Nanopore Single-Molecule Counter for Selective miRNA Detection", Methods in Molecular Biology, 2017, pp. 255-268, vol. 1632.
UCLA Chemistry & Biochemistry, "Standard Operating Procedure Working with Osmium Tetroxide", Procedures for Safe Use of Osmium Tetroxide, 2009, pp. 1-5.
Valihrach et al., "Circulating miRNA Analysis for Cancer Diagnostics and Therapy", Molecular Aspects of Medicine, 2019, pp. 1-19.

(56) References Cited

OTHER PUBLICATIONS

Valpione et al., "Detection of Circulating Tumor DNA (ctDNA) by Digital Droplet Polymerase Chain Reaction (dd-PCR) in Liquid Biopsies", Methods in Enzymology, 2019, pp. 1-15, vol. 629.

Vidal et al., "Dynamic Treatment Stratification Using ctDNA", Recent Results in Cancer Research, Abstract, 2020, 1 page.

Wang et al., "Circulating MiRNA-21 as a Diagnostic Biomarker in Elderly Patients with Type 2 Cardiorenal Syndrome", Scientific Reports, 2020, pp. 1-9, vol. 10, No. 4894.

Wang et al., "Selective Single Molecule Nanopore Sensing of MicroRNA Using PNA Functionalized Magnetic Core? Shell Fe3O4 ?Au Nanoparticles", Analytical Chemistry, 2019, pp. 7965-7970, vol. 91, No. 12.

Wanunu et al. "Rapid Electronic Detection of Probe-Specific MicroRNAs Using Thin Nanopore Sensors", Nature Nanotechnology, 2010, pp. 807-814, vol. 5, No. 11.

Wilson et al., "High-Fidelity Nanopore Sequencing of Ultra-Short DNA Targets", Analytical Chemistry, 2019, pp. 6783-6789, vol. 91.

Workman et al. "Nanopore Native RNA Sequencing of a Human Poly(A) Transcriptome", Nature Methods, 2019, pp. 1297-1305, vol. 16, No. 12.

Xi et al., "Nanopore-Based Selective Discrimination of MicroRNAs with Single-Nucleotide Difference Using Locked Nucleic Acid-Modified Probes", Analytical Chemistry, 2016, pp. 10540?10546, vol. 88.

Zahid et al., "Sequence-Specific Recognition of MicroRNAs and Other Short Nucleic Acids with Solid-State Nanopores", Nano Letters, 2016, pp. 2033-2039.

Zhang et al., "Sequence-Specific Detection of MicroRNAs Related to Clear Cell Renal Cell Carcinoma at fM Concentration by an Electroosmotically Driven Nanopore-Based Device", Analytical Chemistry, Abstract, 2017, 1 page.

$I_r/I_o$ in 0.05 bins

```
/\/\/\/\/\/\/\/\
(O|x|B|p|D|e|t|e|c|t)
\/\/\/\/\/\/\/\/
=========== Thresholds ============
Event duration (in tps): 4 - 300
Lowest Ir/Io < 0.55
All Ir/Io < 0.6
================================
Processing channel 1...
400 events detected.
# Channel 1, Sampling rate: 3012.0 Hz, Io: 251.7634153356089 pA
    1    353587    353611    0.09775701
    2    398370    398375    0.11623832
    3    407336    407348    0.08820084
    4    412256    412438    0.21670561
    5    447187    447197    0.07593458
    6    453217    453249    0.06600467
    7    491322    491371    0.07008346
    8    493357    493361    0.32476636
    9    497967    498043    0.21728972
   10    520164    520179    0.19742991
   11    542446    542455    0.06074766
   12    567601    567612    0.08528037
   13    595027    595031    0.33294393
   14    650430    650488    0.08002336
   15    650828    650858    0.16647196
   16    742841    743058    0.04614486
   17    792186    792318    0.12733645
   18    832875    832913    0.04672897
   19    841164    841188    0.28387851
   20    907859    907866    0.27686916
   21    1073757   1073771   0.19801402
   22    1075537   1075541   0.34521028
   23    1080276   1080460   0.15887851
   24    1081066   1081078   0.15478972
   25    1101348   1101364   0.21378505
   26    1110665   1110672   0.26108813
   27    1132460   1132678   0.23948598
   28    1178961   1179019   0.39252336
   29    1211889   1211901   0.26518692
   30    1267382   1267386   0.28679907
```

Fig. 8

```
∧∧∧∧∧∧∧∧∧∧
|O|s|B|p|O|e|t|e|c|t|
∨∨∨∨∨∨∨∨∨∨
=========== Thresholds ===========
Event duration (in bps): 4 - 300
Lowest r/o < 0.55
All r/o < 0.6

==================================
Processing channel 1...
Processing channel 2...
Processing channel 3...
Processing channel 4...
39 events detected.
# Channel 4, Sampling rate: 3012.0 Hz, t0: 240.234571248129282 g.
        1    967674     967705   0.09469523
        2    766999     767209   0.29651763
        3    918896     918923   0.09469523
        4   1080173    1080204   0.30946963
        5   1599317    1599525   0.30379437
        6   1680746    1680758   0.28580171
        7   2049151    2049182   0.16034372
        8   2051214    2051247   0.18665851
        9   2087063    2087068   0.18359853
       10   2397779    2397785   0.15422377
       11   2544443    2544458   0.26376989
       12   2862924    2862940   0.28533373
       13   3044089    3044100   0.41003672
       14   3150965    3150971   0.35495716
       15   4810901    4810911   0.41554468
       16   4810943    4810950   0.41615667
       17   4811778    4811783   0.48347613
       18   4812081    4812139   0.41432069
       19   4812197    4812203   0.46511625
       20   5915973    5915996   0.43329233
       21   5916909    5916984   0.41432069
       22   6204350    6204361   0.29620563
       23   6218384    6218451   0.13219094
       24   6314244    6314248   0.33459731
       25   6533152    6533163   0.24235006
       26   6694009    6694020   0.34210536
       27   6716411    6716419   0.19828641
       28   7095854    7095865   0.43941249
       29   7136165    7136282   0.45777234
       30   7214310    7214328   0.18849449
```

Fig. 8 Cont.

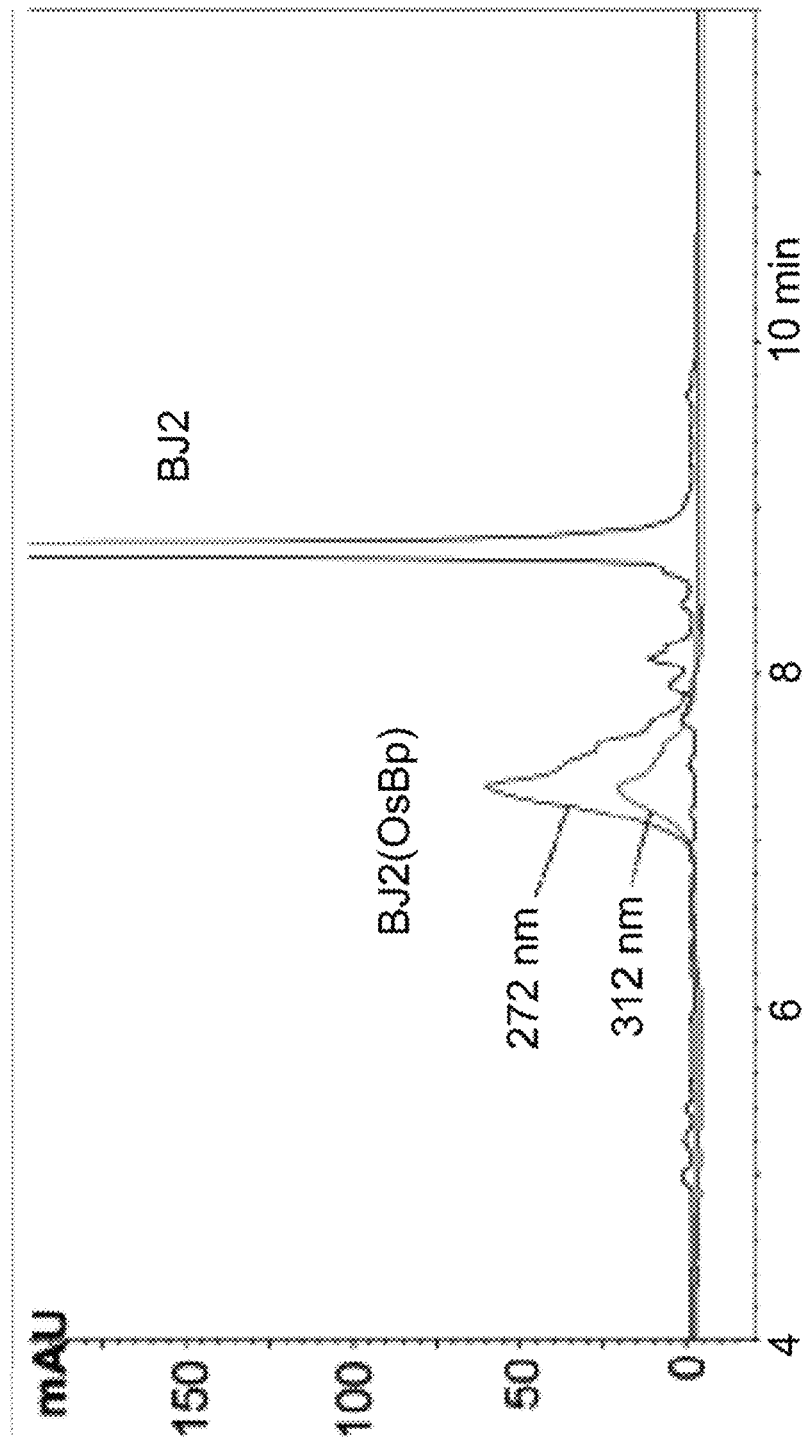

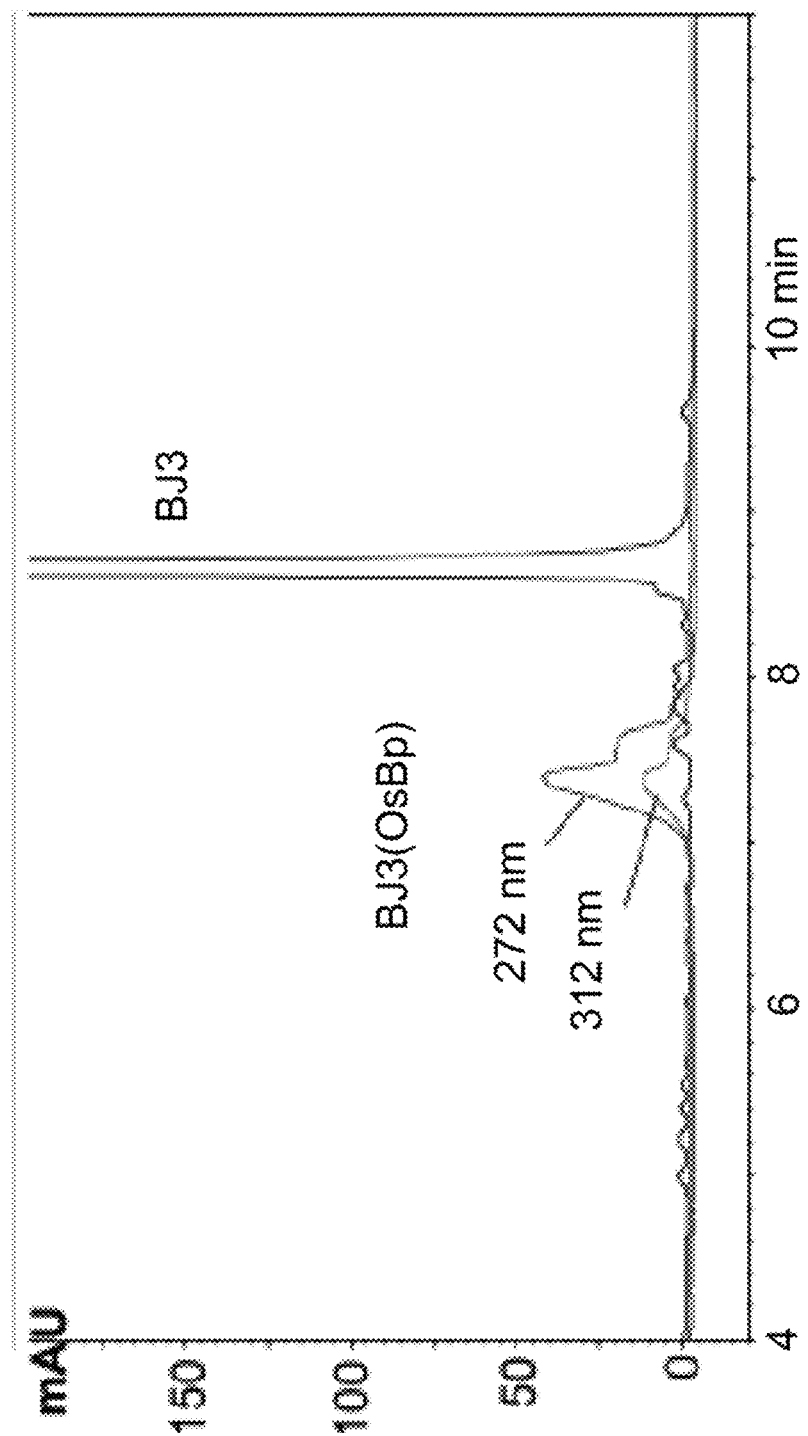

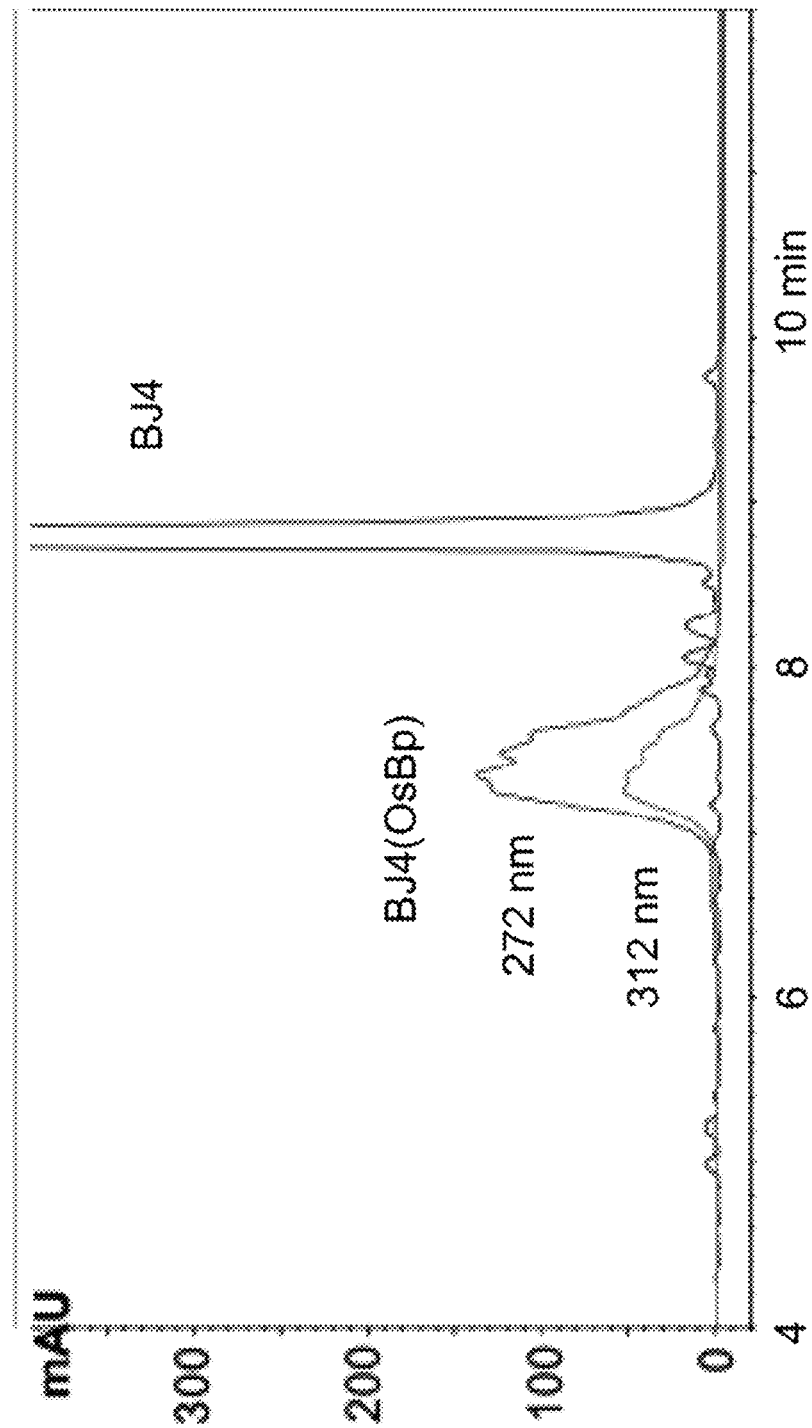

OSMIUM TAGGED PROBES FOR NUCLEIC ACID DETECTION

CROSS-REFERENCE TO RELATED APPLICATIONS

This application is a Continuation of U.S. patent application Ser. No. 17/466,931, filed Sep. 3, 2021, now U.S. Pat. No. 11,427,859, issued Aug. 30, 2022, which is a Divisional of U.S. patent application Ser. No. 17/063,245, filed Oct. 5, 2020, now U.S. Pat. No. 11,111,527, issued Sep. 7, 2021, which are incorporated herein by reference in their entireties.

STATEMENT REGARDING FEDERALLY-SPONSORED RESEARCH AND DEVELOPMENT

This invention was made with government support under grant #R43HG010841 awarded by the NIH/NHGRI, SBIR program. The government has certain rights in the invention.

REFERENCE TO SEQUENCE LISTING SUBMITTED ELECTRONICALLY

The content of the electronically submitted sequence listing in XML text file (Name: 68812-221738_SL.xml; Size: 140,055 bytes; and Date of Creation: Oct. 25, 2022) filed with the application is incorporated herein by reference in its entirety.

BACKGROUND

Blood draw or other body fluid samples, known as liquid biopsies (Bronkhorst, A. J., Ungerer, V., & Holdenrieder, S. (2019); Vidal, J., Taus, A., & Montagut, C. (2020); Pös, O., Biró, O., Szemes, T., & Nagy, B. (2018); Oellerich, M., Schütz, E., Beck, J., & Walson, P. D. (2019); Stewart, C. M., & Tsui, D. (2018); Giannopoulou, L., Kasimir-Bauer, S., & Lianidou, E. S. (2018); Satyal, U., Srivastava, A., & Abbosh, P. H. (2019); Finotti, A. et al. (2018); Valpione, S., & Campana, L. (2019); and Kwapisz D. (2017)) contain pertinent information regarding the health status of an individual, the progress of a disease, whether or not an individual is disease-free after surgery, and even whether or not a certain therapy strategy seems promising (Vidal, J., Taus, A., & Montagut, C. (2020)). Liquid biopsies are far less invasive procedures than surgical/tumor biopsy. Body fluids contain cell-free DNA (cfDNA), a fraction of which can originate from a tumor (circulating tumor DNA; ctDNA). In 2016 the US Food and Drug Administration approved the first liquid biopsy test for EGFR-activating mutations in patients with non-small-cell lung cancer as a companion diagnostic test to enable therapy selection (Kwapisz D. (2017)). Cell-free DNA is believed to be fragmented and shorter in diseased individuals compared to healthy (Pös, O., Biró, O., Szemes, T., & Nagy, B. (2018)). In addition to DNA, body fluids contain transfer RNA-derived fragments and non-coding RNA oligos in the range of 20 to 300 nucleotides (nt) (Kim H K, Yeom J H, Kay M A. (2020); Poller W, et. al. (2018); Mitchell, P. et al. (2008); Aggarwal, V., Priyanka, K., & Tuli, H. S. (2020): Meseure, D., Drak Alsibai, K., Nicolas, A., Bieche, I. & Morillon, (2015)). Among them is a group of single-stranded (ss) RNAs, 17 to 25 nt long, known as microRNAs or miRNAs. They were discovered 20 years ago and proven to be the tiny regulators that control the post-transcriptional expression of proteins (Ambros, V. (2001): Bartel, D. P. (2004)). miRNAs are highly conserved and surprisingly stable in body fluids (Mitchell, P. et al. (2008); Mall, C., Rocke, D. M., Durbin-Johnson, B., & Weiss, R. H. (2013)). Currently there are over 2,300 human miRNAs known (Alles J. et al. (2019)), the subject of over 100,000 scientific publications. Up- or down-regulation of miRNAs is associated with various human diseases including cancer, heart disease, kidney disease, obesity, diabetes, etc. (Bartel, D. P. (2004)); miRNAs are proposed as biomarkers (Farazi, T. A., Hoell, J. I., Morozov, P., & Tuschl, T. (2013); Pogribny, I. P. (2017)) and as potential therapeutics (Rupaimoole, R. & Slack, F. J. (2017)) in personalized medicine. Body fluids contain trace amounts of cfDNA, ctDNA, fragmented coding RNAs (Kim H K, Yeom J H, Kay M A. (2020)), non-coding RNAs (Poller W, et. al. (2018)), and miRNAs, that require simple, validated, and highly sensitive assays for testing (Finotti, (2018); Valpione, S., & Campana, L. (2019); Raabe, C., Tang T., Brosius J., & Rozhdestvensky, T. (2014)). Current technologies for "small RNA" identification and quantitation, include microarray, NGS sequencing (Ion Torrent or Illumina (small RNA-seq)), and qRT-PCR-based methods that have been employed so far with great success (Ferracin, M., & Negrini, M. (2018); Valihrach, L., Androvic, P., & Kubista, M. (2020); Gines, G., Menezes, R., Xiao, W., Rondelez, Y., Taly, V. (2020)). These technologies, however, require substantial infrastructure and skilled personnel, are not well-suited for point-of-care testing, and are out of the question for home testing.

Figure 1B:
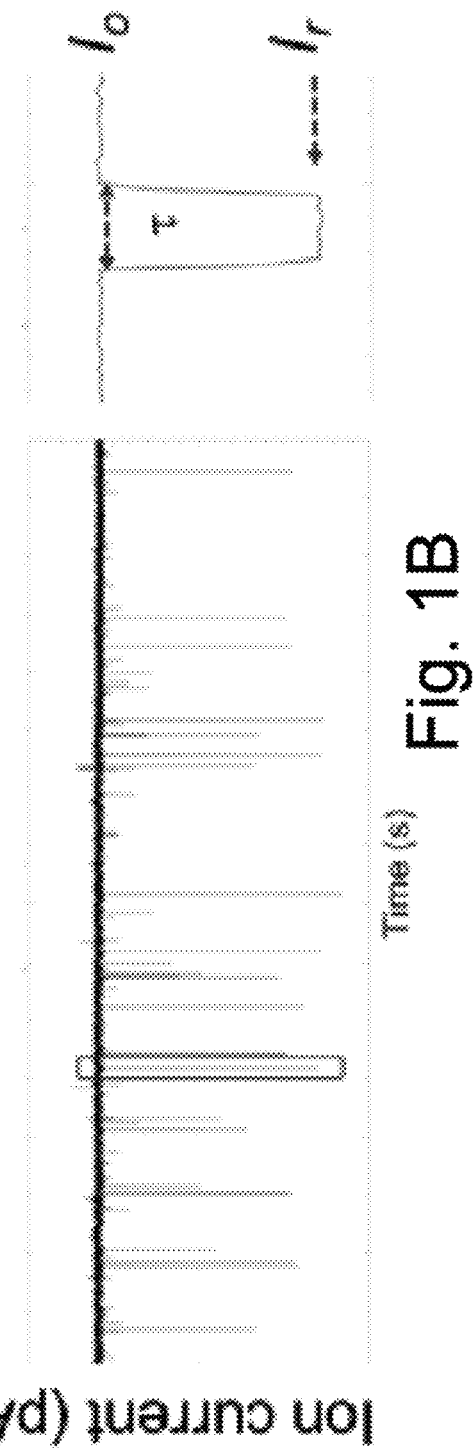

The last 30 years have seen a surge in nanopore-based technologies using either solid-state or protein nanopores (Kasianowicz, J. J., Brandin, E., Branton, D. & Deamer, D. W. (1996); Butler, T. Z., Gundlach, J. H. & Troll, M. (2007); Maglia, G., Heron, A. J., Stoddart, D., Japrung, D. & Bayley, H. (2010); Haque, F., Li, J., Wu, H. C., Liang, X. J. & Guo, P. S (2013); Fuller C. W. et al. (2016); Laszlo, A. H. et al. (2014); Oxford Nanopore Technologies website: nanoporetech.com, under Resources/Publications). In 2014 Oxford Nanopore Technologies (ONT) introduced and commercialized the first portable nanopore device to sequence DNA and RNA practically anywhere, as long as a computer and internet are available (Oxford Nanopore Technologies website: nanoporetech.com, under Resources/Publications). The ONT technology is based on the CsGg protein nanopore (Cao, B. et al. (2014)), with a sub 2 nm diameter, inserted in a planar lipid bilayer membrane that separates two electrolyte filled compartments (FIG. 1A). Applying a voltage across the two compartments leads to a constant flow of electrolyte ions (Io) via the pore, recorded as a function of time (i-t). The passage of a single molecule through the pore reduces Io to a lower level of residual ion current (Ir). This is recorded as an "event" with (Ir) and residence time (c) (FIG. 1B). Currently the ONT platform is exclusively used for DNA/RNA sequencing (Oxford Nanopore Technologies website: nanoporetech.com, under Resources/Publications), while comparable nanopore platforms are successfully employed for single molecule analyses (Chen, X., Wang, L., & Lou, J. (2020); Chaudhary, V., Jangra, S. & Yadav, N. R. (2018); Wanunu M, Dadosh T, Ray V, Jin J, McReynolds L, Dmdid M. (2010); Gu, L. Q. & Wang Y. (2013); Arata, H., Hosokawa, K., & Maeda, M. (2014); Henley, R. Y., Vazquez-Pagan, A. G., Johnson, M., Kanavarioti, A. & Wanunu, M. (2015); Xi, D. et al. (2016); Zahid, O. K., Wang, F., Ruzicka, J. A., Taylor, E. W. & Hall, A. R. (2016); Ding, Y. & Kanavarioti, A. (2016); Tian, K., Shi, R., Gu, A., Pennella, M., & Gu, L. Q. (2017); Zhang, Y., Rana, A., Stratton, Y., Czyzyk-Krzeska, M. F., & Esfandiari, L.

(2017); Huang, G., Willems, K., Soskine, M., Wloka, C. & Maglia, G. (2017); Galenkamp, N. S., Soskine, M., Hermans, J., Wloka, C. & Maglia, G. (2018); Sultan M., Kanavarioti, A. (2019); Cao, C. et al. (2019); Hao, W., Haoran T., Cheng Y., & Yongxin, L. (2019)).

ONT provides portable nanopore devices that carry two types of flow cells; the MinION with 512 channels and the Flongle with 126 channels, all monitored simultaneously (Oxford Nanopore Technologies website: nanoporetech.com, under Resources/Publications). ONT promotes these devices for direct sequencing of DNA and RNA with a minimum length of 200 nucleotides (nt) (Oxford Nanopore Technologies website: nanoporetech.com, under Resources/Publications). To date, however, attempts to sequence RNAs shorter than 200 nt following ONT protocol appear unsuccessful (Workman, R. E. et al. (2019)), absent circularization and rolling circle amplification to produce long DNA with 100 nt repeats (Wilson, B. D., Eisenstein, M. & Soh, H. T. (2019)). Most of the DNA/RNA available in biological fluids is fragmented with lengths estimated in the range of 200 bp (Pös, O., Biró, O., Szemes, T., & Nagy, B. (2018)) and miRNAs are very short (Ambros, V. (2001)), and therefore not amenable to direct ONT sequencing protocols. Although several other experimental nanopore platforms have been successfully used for miRNA profiling, they have not been shown as suitable for commercial utilization. Thus, there remains a need for a technology that is accessible, ready-to-use, relatively inexpensive, and does not require any special skills or infrastructure.

SUMMARY

Provided for herein is a method for detecting the presence of a nucleic acid target molecule in a biological sample. In certain aspects, the method comprises the steps of: (a) contacting a test sample that comprises (i) a biological sample comprising a nucleic acid target molecule and (ii) an osmylated single-stranded oligonucleotide probe comprising at least one pyrimidine residue covalently bonded to a substituted or unsubstituted Osmium tetroxide (OsO4)-2,2'-bypyridine group (OsBp group), wherein the sequence of the probe is at least partially complementary to the sequence of the nucleic acid target molecule, to allow the formation of a hybridized probe/target complex; (b) using a nanopore device to detect in the test sample the number of events wherein unhybridized osmylated-probe traverses the nanopore; and (c)(i) comparing the number of events detected in the test sample to a number of corresponding probe sample events wherein unhybridized osmylated-probe traverses the nanopore in the absence of the nucleic acid target, wherein a reduction in the number of events detected in the test sample relative to the number of probe sample events is indicative of the formation of the hybridized probe/target complex in step (a) and the presence of the nucleic acid target molecule in the test sample; (c)(ii) comparing the number of events detected in the test sample to the noise of a corresponding baseline sample that does not contain any osmylated-probe, wherein an absence of an increase in the number of events detected in the test sample relative to the noise of the baseline sample is indicative of the formation of the hybridized probe/target complex in step (a) and the presence of the nucleic acid molecule in the test sample; and/or (c)(iii) comparing the number of events detected in the test sample to a number of corresponding control sample events wherein unhybridized osmylated-probe traverses the nanopore in the presence of a known amount of the nucleic acid target molecule, wherein a reduction in the number of events detected in the test sample relative to the number of control sample events is indicative of increased formation of the hybridized probe/target complex in step (a) and the presence of a higher amount of the nucleic acid target molecule in the test sample over the control sample or wherein an increase in the number of events detected in the test sample relative to the number of control sample events using the same amount of probe is indicative more unhybridized probe and thus of a lower amount of the nucleic acid target molecule in the test sample compared to the control sample. In certain aspects, at least one osmylated pyrimidine is a thymine residue (T).

Further, certain aspects provide for a kit comprising an osmylated probe of this disclosure and a control nucleic acid target molecule that can hybridize to the probe and for the use of such probe for detection of a nucleic acid target molecule with a nanopore device, wherein the nucleic acid target molecule is optionally a ctDNA, cfDNA, miRNA, or a non-coding RNA, optionally, wherein the non-coding RNA is less than about 300 bases long.

BRIEF DESCRIPTION OF THE DRAWINGS/FIGURES

FIG. IA-D. (FIG. IA) Schematic representation of a nanopore within a planar bilayer lipid membrane that separates two electrolyte filled compartments. Applying a constant voltage to the flow cell guides the passage of ions through the nanopore creating a measurable ionic current. (FIG. 1B) The i-t trace obtained from a voltage-driven ion-channel experiment where the constant flow of electrolyte ions (Io) via the pore is interrupted by the passage of molecules. These molecules appear as "events" with residual ion current Ir and residence time τ. (FIG. iC) OsBp labeling reaction: OsO4 and 2,2-bipyridine (bipy) have a low association constant, but their mixture adds to the C5-C6 double bond of pyrimidines and forms a stable conjugate. The addition of OsBp creates a chromophore that absorbs in the range of 312 nm where native nucleic acids do not absorb (see Examples). (FIG. 1D) Illustration of the concept behind the proposed diagnostic test. ssDNA and ssRNA traverse the nanopore and exhibit few counts because they traverse faster, compared to the device's relatively slow acquisition rate; ds nucleic acids are too big and do not traverse this nanopore. Despite being bulkier than ss native nucleic acids, osmylated ss nucleic acids traverse the pore, but more slowly compared to the device's acquisition rate and consequently produce numerous events. When an osmylated nucleic acid (probe) is added to a sample that contains its complementary nucleic acid (target), the probe and the target form a hybrid. When the target's concentration is equal or higher than the probe's concentration, the probe is hybridized. The probe is then prevented from traversing the pore, and few or no events are observed. The absence of target in the sample is evidenced by the numerous events produced by the probe while it freely traverses the pore.

Figures 2A, 2B:
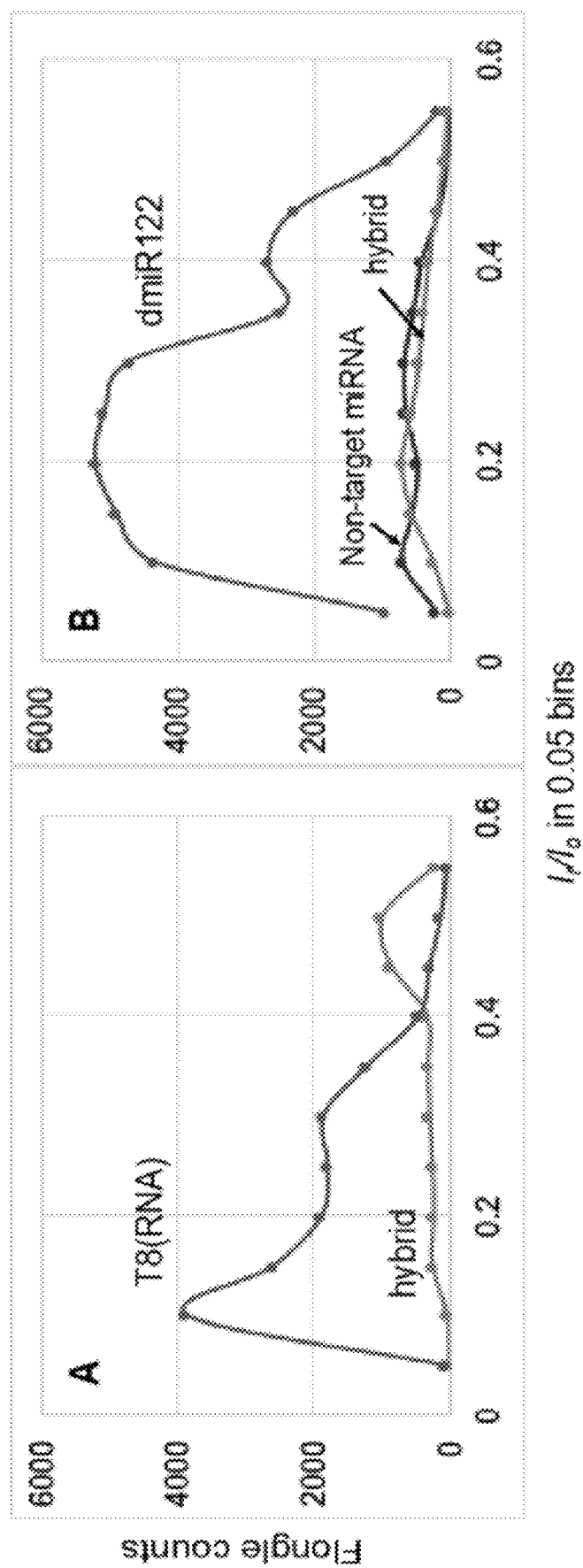

FIG. 2A,B. Voltage-driven ion-channel (nanopore) experiments conducted with the Flongle ONT device; samples in >90% ONT buffer. (FIG. 2A) 1 h at −200 mV using the same Flongle flow cell: (i) 5 μM probe T8(RNA) and (ii) 5 μM each a mixture of T8(RNA) and d(CT)10. It is noticeable that these two molecules are only partially complementary to each other. Count of events (counts) were obtained using the OsBp_detect software to analyze and report the raw fast-5 tile data acquired with MINKNOW (Kanavarioti, A., & Kang, A. See RNA(OsBp) event detection Python package in a public repository: on the world wide web at github.com/kangaroo96/osbp_detect and for step-by-step installation instructions see at the world wide web at github.com/kangaroo96/osbp_detect/blob/master/instructions.md; see Examples). Counts were plotted as a function of Ir/Io with a bin size of 0.05. (FIG. 2B) 2 h at −190 mV using the same Flongle flow cell: (i) 5 µM probe dmiR122, (ii) 5 µM each a mixture of dmiR122 and miRNA122, and (iii) 1 h at −180 mV a mixture 10 µM each of miRNA122 and miRNA140 using a different Flongle flow cell. It is noticeable that dmiR122 carries 4 OsBp moieties and its sequence is perfectly complementary to miRNA122. Data acquisition and analysis as described under (FIG. 2A).

FIG. 3A-D. Alternative approaches to testing hybridization between osmylated probes and targets. (FIG. 3A) Enzymatic elongation of osmylated primers using ssM13mp18 DNA as the template and DNA polymerase; time points obtained at 5, 10 and 20 min. No primer and M13rev(−48) used as negative controls. With the exception of BJ1, all the other osmylated primers exhibit enzymatic elongation comparable to the positive control M13fwd(6097). Absence of elongation with BJ1 is attributed to the presence of a T(OsBp) at the 3'-end. (FIG. 3B), (FIG. 3C) and (FIG. 3D) Overlapping HPLC profiles from the analyses of different samples, with samples at about 5 µM in about 90% ONT buffer. The same HPLC method B was used for all the samples (see Examples). Intact ss oligos and ds oligos appear as sharp peaks, whereas osmylated oligos and hybrids with one osmylated strand appear as broad peaks: hybrids elute later compared to ss nucleic acids. (FIG. 3B) Sample composition: intact BJ2, intact complement of primerM13for(−41). The HPLC profile of their equimolar mixture is consistent with hybridization. (FIG. 3C) Sample composition: miRNA21, probe 21EXT carrying 8 dT(OsBp) moieties, and equimolar mixture of the two. HPLC profile of the mixture consistent with NO hybridization, attributed to the high number of single OsBp tags, 6 within a sequence of 22 nt, likely to distort the helical structure of the probe, and prevent ds formation. (FIG. 3D) Sample composition practically the same as under (FIG. 3B), with the exception that in these samples BJ2 carries 6 dT(OsBp) moieties (first peak with broad shape and absorbance at 312 nm). HPLC profile of the mixture is consistent with hybridization, attributed to the fact that most of the OsBp moieties are adjacent, so that the rest of the sequence can still hybridize with the target.

FIG. 4A-D. Same samples tested by HPLC and by nanopore; samples in >90% ONT buffer. (FIG. 4A) Overlapping HPLC profiles of samples, at about 0.2 nmoles, in ONT buffer (i) probe BJ1, (ii) target is shown here at a much higher load, and (iii) mixture of probe at about 0.2 nmoles and target with about 30% excess over the probe (hybrid). The HPLC profile of the mixture is consistent with hybridization. (FIG. 4C) Overlapping HPLC profiles (i) of the probe BJ2 TA(OMe) at about 0.2 nmole load and (ii) its approximately equimolar mixture with the complementary target, complementary primerM13for(−41). Target identified as a small peak, at 5% excess over the probe. The HPLC profile of the mixture (hybrid) is consistent with ds formation. HPLC profiles for these two samples are shown at both the 272 and 312 nm (see Examples). (FIG. 4B) and (FIG. 4D) One hour long nanopore experiments conducted with a MinION flow cell using the same samples as in (FIG. 4A) and (FIG. 4C), respectively; Samples in (FIG. 4B) were used as is, while samples in (FIG. 4D) were used after a 1000-fold or 100-fold dilution in ONT buffer. (FIG. 4B) Probe BJ1 was tested at −180 mV (dashed trace) and showed few counts. No sample was added, the voltage was raised to −220 mV and an additional nanopore experiment was conducted at −220 mV (solid trace) with counts exceeding 100,000. In contrast to the counts obtained with BJ1, the hybrid sample exhibited remarkably few counts (solid trace, every close to the x-axis, tested 1 h at −490 mV). (FIG. 4D) Nanopore experiments using the same flow cell: (i) control/buffer test (0.75 h tested at −180 mV), (ii) probe BJ2 TA(OMe) at 0.38 pmole load (2 h tested at −210 mV), (iii) equimolar mixture of probe and target at 0.38 pmole load each (1 h tested at −210 mV). The observation of lower counts with the hybrid sample compared to the probe sample suggest target identification for either (FIG. 4B) and (FIG. 4D), in agreement with the HPLC results. The nanopore experiment with BJ2 TA(OMe) probe at the 0.38 pmole load suggests probe detectability at the sub-pmole level. The experiment with the hybrid sample in (d) indicates that the hybrid endures under the experimental conditions of duration and applied voltage. Data acquisition and analysis as described under FIG. 2A.

FIG. 5A-D. Nanopore experiments testing advanced probe designs and probe detection in 15% human serum—85% ONT buffer. (FIG. 5A) Three consecutive nanopore experiments conducted with the same flow cell. (i) Buffer test 0.75 h at −180 mV, (ii) probe 2XdmiR122 tested 1.5 h at −180 mV (dashed line) and (iii) no sample added, voltage raised to −220 mV and experiment run for 1.5 h. This set of experiments provided solid evidence that, at least, this probe is not traversing the ONT nanopores at −180 mV even during a 1.5 h long experiment. In addition, it illustrates that this probe traverses the pores under applied voltage of −220 mV, and produces a high count of detectable events. (FIG. 5B) Four consecutive nanopore experiments conducted with the same but previously used flow cell that carries only around half, i.e., 250, working nanopores. (i) buffer test at −180 mV, (ii) probe 122EXT at a load 3-times less compared to regular load of 5 µM (corresponding to 0.38 nmoles) tested at −180 mV (dashed line), (iii) no sample added, voltage raised to −220 mV and (iv) new sample with same load of probe 122EXT as in (ii), but prepared in 15% human serum—85% ONT buffer. (FIG. 5C) HPLC profiles of (i) intact miRNA122, (ii) probe 2XdmiR122 at 0.5 µM, a 10-fold lower concentration compared to the typical 5 µM sample concentration and (iii) mixture probe to target=1:2, also at a 0.5 µM concentration in probe (hybrid). All three samples in >900% ONT buffer and monitored at 260 nm using HPLC method B (see Examples). The latter two samples were used, as is, for the nanopore experiments shown in FIG. 5D. (FIG. 5D) Consecutive nanopore experiments on the same flow cell. (i) Buffer test, 1 h at −220 mV, (ii) probe 2XdmiR122, 3 h at −220 mV and (iii) hybrid sample with miRNA122, in excess over the probe, tested for 1 h at −220 mV. This experiment confirms sensitivity in the detection of 2XdmiR122, albeit via a 3 h long experiment, and confirms that hybridization with target results in severely reduced counts, i.e., silencing. Data acquisition and analysis for the nanopore experiments as described under FIG. 2A.

Figure 6A:
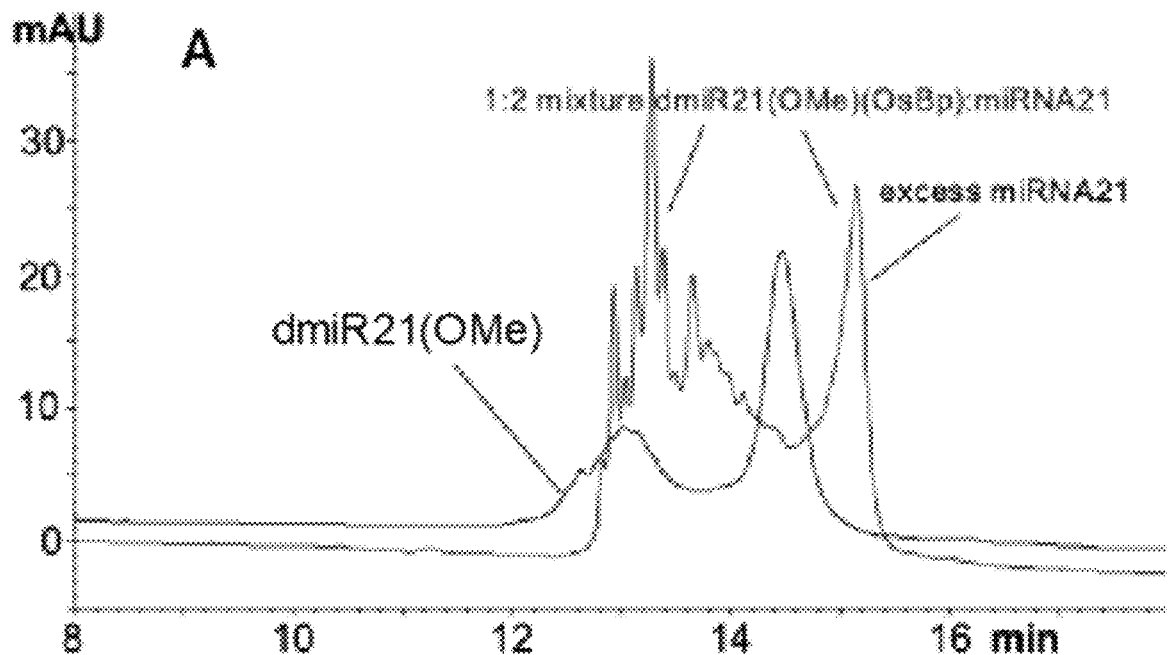

FIG. 6A,B. Targeting miRNA21 in a complex mixture. (FIG. 6A) HPLC profiles of two samples analyzed with HPLC method B (see Examples): (i) probe dmiR21(OMe) at 0.15 nmole load and (ii) 1:2 mixture of this probe with miRNA21 at a 0.30 nmole probe load. The probe's HPLC profile exhibits two peaks, the larger one eluting after the minor one. This profile is consistent with the determined value of 2.85 OsBp moieties per molecule, on average, meaning that this preparation includes molecules with 2 and molecules with 3 OsBp tags. The HPLC profile of the 1:2 mixture of probe to target exhibits a single rather sharp peak eluting after a broad rather complex peak. It was confirmed that the sharp peak corresponds to the excess miRNA21 target. We attribute the broad complex peak to multiple hybrids, the result of one target and many probes, all complementary to the target, but each one of them carrying OsBp moieties at a different nucleobase. It is reasonable to assume that the chromatography resolves these hybrids, as it resolves topoisomers with such short osmylated oligos (Kanavarioti, A. (2016)) (HPLC method B in Examples). The observation of distinct HPLC profiles between probe and mixture samples is consistent with hybridization. (FIG. 6B) Four nanopore MinION experiments two of them using the exact samples analyzed by HPLC in (FIG. 6A): (i) probe dmiR21(OMe), tested for 2 h at −180 mV, exhibited over 100,000 events, (ii) 1:2 mixture of this probe with miRNA21, tested for 1 h at −180 mV, exhibited negligible counts (hybrid). Two additional experiments tested the effect of excess non-target RNA in the translocation properties of probe dmiR21(OMe) and its hybrid with miRNA21. The excess non-target RNA was at a 10-fold higher load compared to the probe and was composed of equimolar amount of miRNA140 and a 100 nt long RNA. Nanopore experiments in the presence of excess non-target RNA (iii) hybrid with miRNA21, 1 h at −180 mV, and (iv) probe dmiR21 (OMe), 2 h at −200 mV. Higher voltage used here to compensate for the hours that this flow cell had worked already, per ONT protocol. The effect of the excess non-target RNA on the hybrid, if any, is not detectable, as the counts are too few. The effect of the excess non-target RNA on the probe appears to be a profile shift and reduced counts by a factor of 2, even though this reduction can be attributed to the number of working nanopores that is also reduced by a factor of about 2. It was noted that probe dmiR21(OMe) translocates efficiently at an applied voltage of −180 mV, as it does not contain any adjacent osmylated dTs. Data acquisition and analysis as described under FIG. 2A.

FIG. 7A-D. Nanopore experiments targeting miRNA140 or miRNA21 at single-digit attomole load. (FIG. 7A) Consecutive nanopore experiments conducted with the same flow cell: (i) buffer test, 1 h at −210 mV, (ii) probe 140EXT (mU) at a 47 fmole load, 1.5 h at −210 mV. (FIG. 7B) Consecutive nanopore experiments conducted with the same used flow cell with less than 200 working nanopores: (i) buffer test, 1 h at −210 mV, (ii) probe 140EXT(mU) at a 3.5 amole load, 1.5 h at −210 mV and (iii) equimolar mixture of 140EXT(mU) and miRNA140, at 3.5 amole load each, 1.5 h at −210 mV (hybrid). (FIG. 7C) HPLC profile of a sample with equimolar concentration of probe 21EXT(mU) and target miRNA21 using HPLC method B (Examples). The appearance of a single peak is consistent with hybridizations. Sample monitored at two different wavelengths to show the absorbance at 312 nm attributed to the presence of the osmylated probe. (FIG. 7D) Consecutive nanopore experiments with the same flow cell; samples were first tested by HPLC, then diluted with ONT buffer by a factor of 109 or 3×108 for probe and hybrid, respectively (see Examples). (i) buffer test, (ii) probe 21EX(mU) at 0.9 amole, and (iii) 1:1 mixture of probe 21EXT(mU) with miRNA21 at 2.8 amole load each, (hybrid). Hybrid exhibits dramatically fewer counts compared to the probe. Data acquisition and analysis for the nanopore experiments as described under FIG. 2A.

FIG. 8. Samples of tsv files, obtained by running the OsBp_detect software on fast-5 files. Left, sample probe T8(RNA); right, sample is a mixture of d(CT)10:T8(RNA)= 1:1, both in about 90% ONT buffer (see FIG. 2A for experimental conditions).

FIG. 9A-D. I-t recordings from two nanopore experiments ranging from 15 to 60 s. Top, probe T8(RNA), i-t recordings from two different channels (see FIG. 9A,B). Bottom, mixture of d(CT)10: T8(RNA)=1:1, i-t recordings from the same two channels as on the top (see FIG. 9C,D). Vertical lines that cross the x-axis (=0 pA) are instrument generated lines by voltage reversal, and not events. Top recordings show multiple and deep events, bottom recordings show few and shallow events. Shallow events are attributed to molecules bumping at the pore aperture, without traversing the pore and they are not counted when selecting "All Ir/Io<0.6" (see FIG. 8 and Examples).

FIG. 10A-D. HPLC profiles of individual components and their 1:1 mixtures in a sample solvent about 90% ONT buffer. All HPLC profiles shown at 260 nm, with the exception of the osmylated probe and hybrid in the top right profile that is shown at 272 nm and 312 nm. Hybridization is evident by a mixture HPLC profile where the main peak elutes after the individual components. (FIG. 10A) Hybridization shown for two intact oligos, BJ1 and its complementary intact oligo (complement primerM13for(−20)). See FIG. 3B for comparable result with another pair of intact oligos. (FIG. 10B) Hybridization shown for probe BJ1 with 5 OsBp out of 30 nt, and its complementary intact oligo (complement primerM13for(−20)). (FIG. 10C) Only partial hybridization is shown for intact BJ1 and its complementary osmylated complement primerM13for(−20) with 11 OsBp out of 35 nt. (FIG. 10D) Hybridization is shown for intact BJ2 and its complementary osmylated complement primerM13for(−41) with 6 OsBp out of 35 nt. HPLC method B is used for analysis (see Examples).

Figure 11:
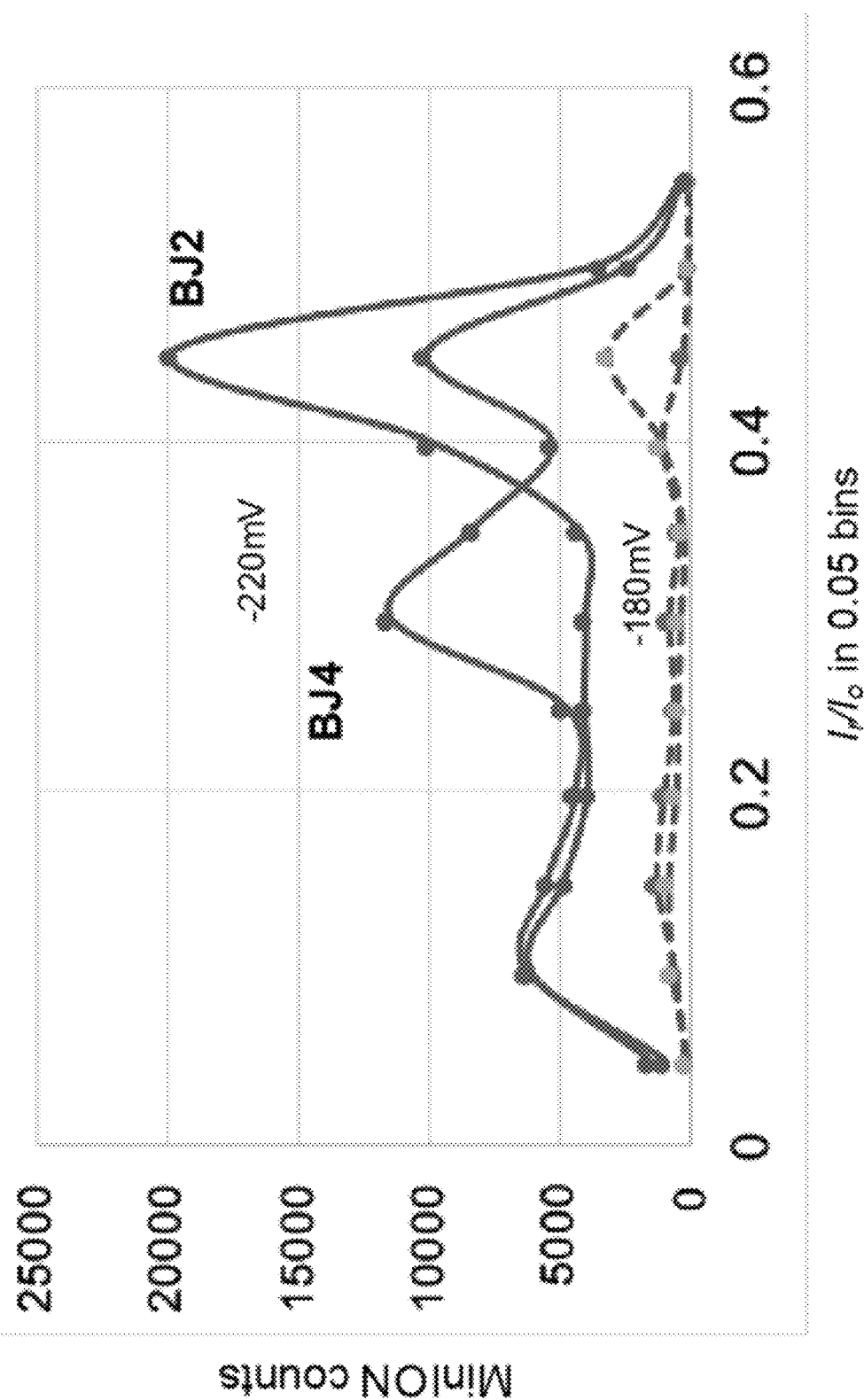

FIG. 11. Nanopore experiments with probes BJ2 and BJ4 show few events at −180 mV and numerous events at −220 mV. Probes BJ2 and BJ4 tested at −180 mV (dashed traces) show negligible number of counts. No new sample was added, the voltage was raised to −220 mV and probes were tested at −220 mV (solid traces) and numerous events were detected. Both probe samples were used at a 0.2 nmole load. Experiments were conducted on the same flow cell in the order BJ2 at −180 mV, BJ2 at −220 mV, BJ4 at −180 mV and BJ4 at −220 mV: the duration of each experiment was 1 h. Data acquisition and analysis as described under FIG. 2A. The dramatic difference in counts at the different applied voltage clearly suggests that these probes and other probes, of similar design, do not traverse the proprietary CsGg nanopore at the lower voltage and require high applied voltage of about −220 mV to translocate.

Figure 12A:
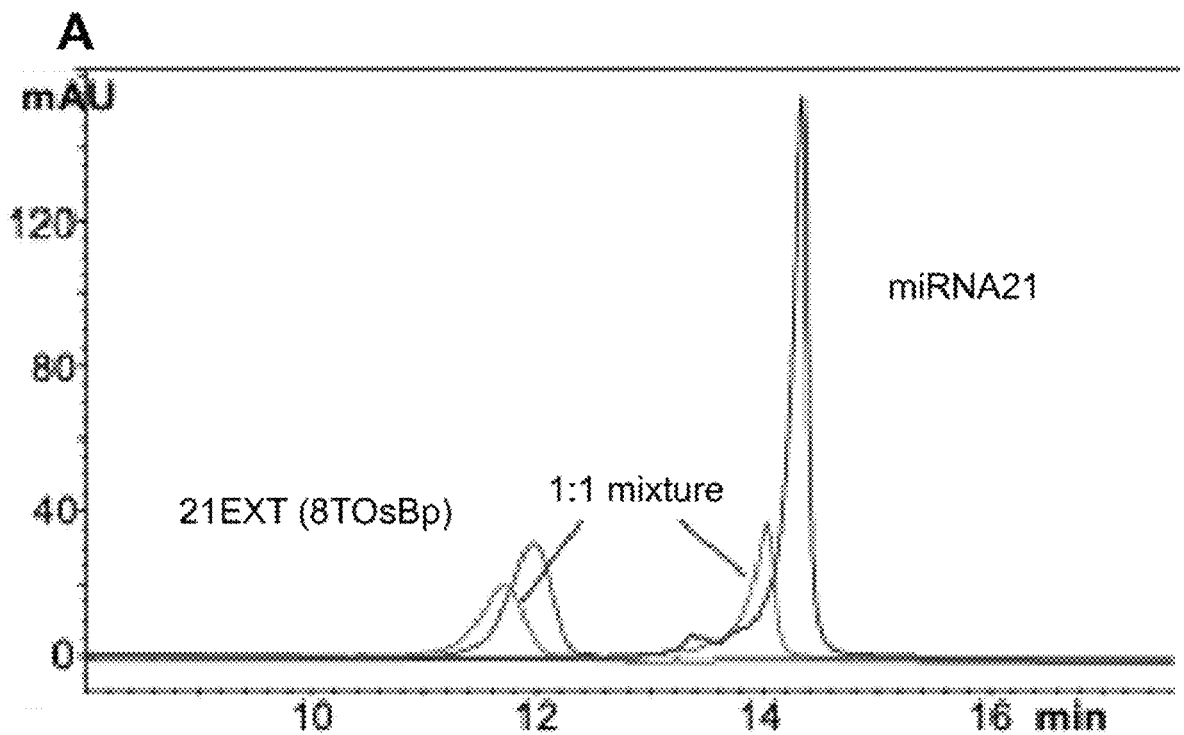

FIG. 12A,B. HPLC profiles of 1:1 mixtures (non-hybrids) of miRNA21 (FIG. 12A) or miRNA21-$A_{15}$ (FIG. 12B) using probe 21 EXT (with 8 T(OsBp), see sequence in Table 1). Samples in about 90% ONT buffer as the sample solvent. HPLC profiles obtained with HPLC method B (Examples). HPLC profile of the mixture sample matches closely the sum of the HPLC profiles of the two components, providing evidence for no detectable hybridization in these two cases. The difference in these two cases is that, due to the added Ali-tail, miRNA21-$A_{15}$ elutes couple of min later compared to miRNA21.

Figure 13:
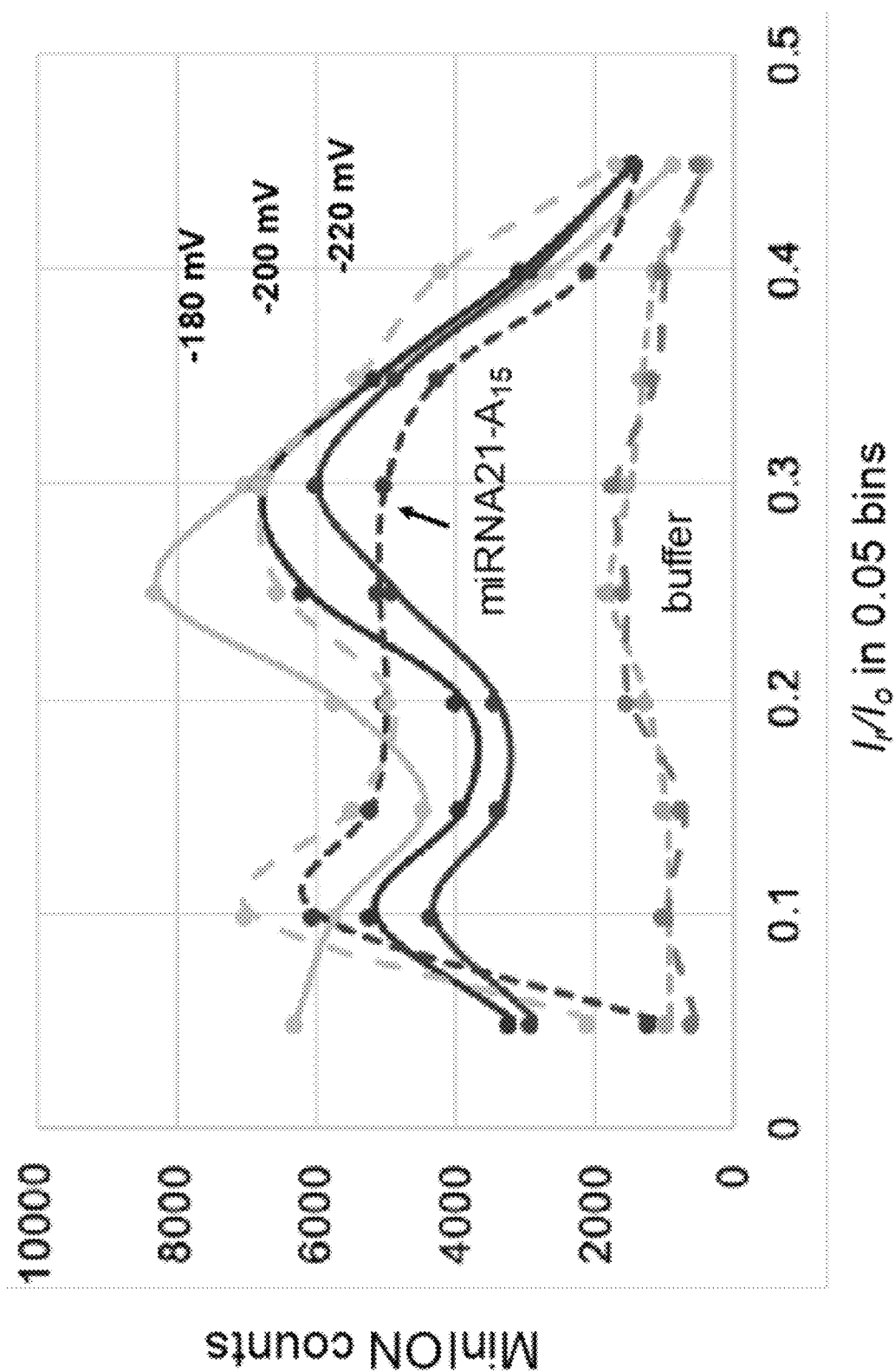

FIG. 13. Effect of applied voltage on the counts observed with a mixture of intact miRNA122 and miRNA140 at 10 µM each at −180 mV, at −200 mV, at −220 mV. Data shown at −180 mV are the same data as in FIG. 2B (Flongle) but normalized by multiplying with 10, as the MinION has about 10 times more working channels compared to the Flongle. Increased applied voltage reduces slightly the count of events, consistent with faster translocation and reduced detectability. An experiment with 10 µM of miRNA21-A15 at −220 mV exhibits comparable counts with the combo of miRNA122 and miRNA140, but a distinct profile compared to the miRNA with no A15-tail. The effect of voltage on the intact RNAs is in stark contrast to the effect of voltage on most of the probes tested in this study. No detectable difference in counts is observed with the control/buffer between −200 and −220 mV.

Figure 14:
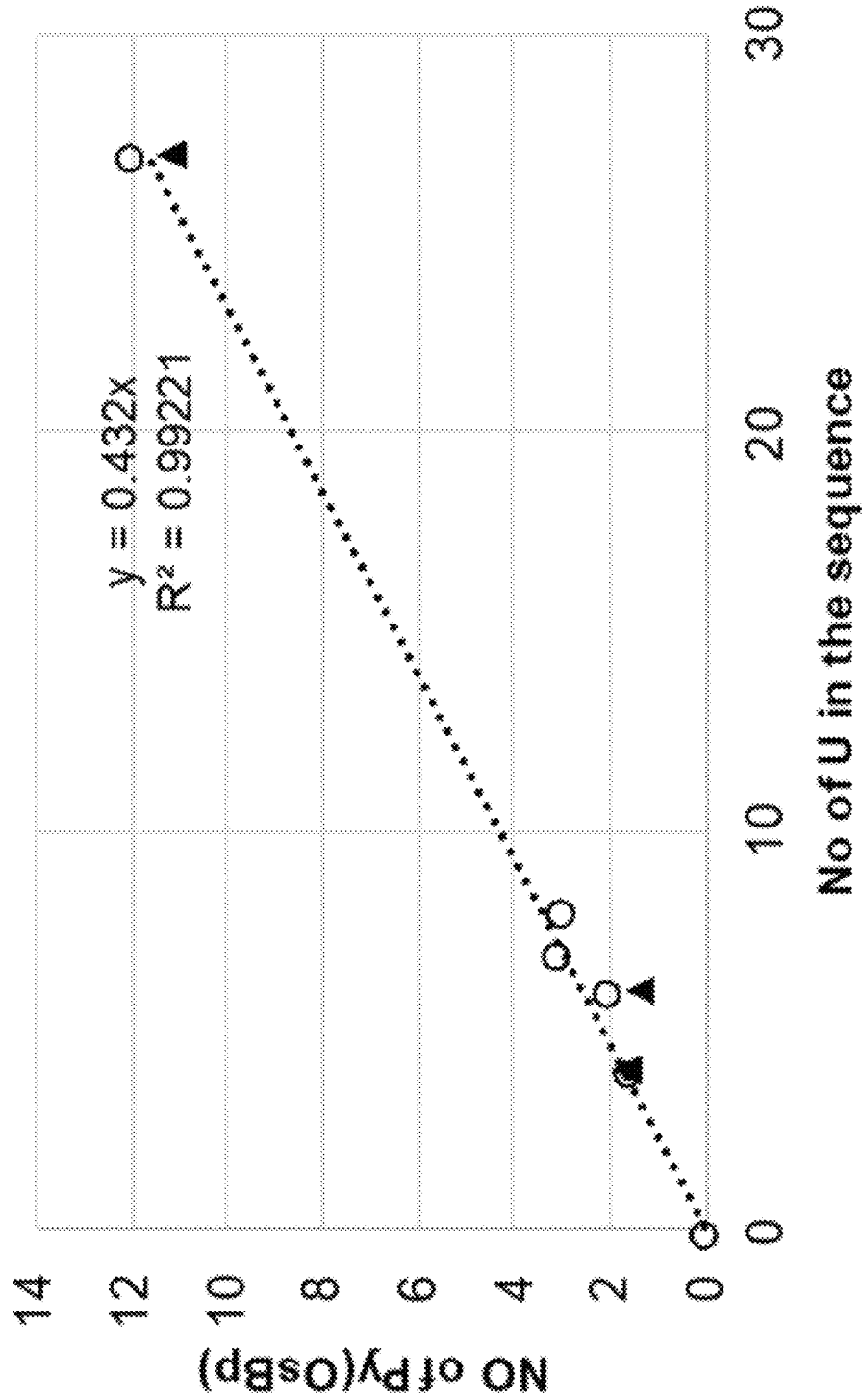
Figure 15A:
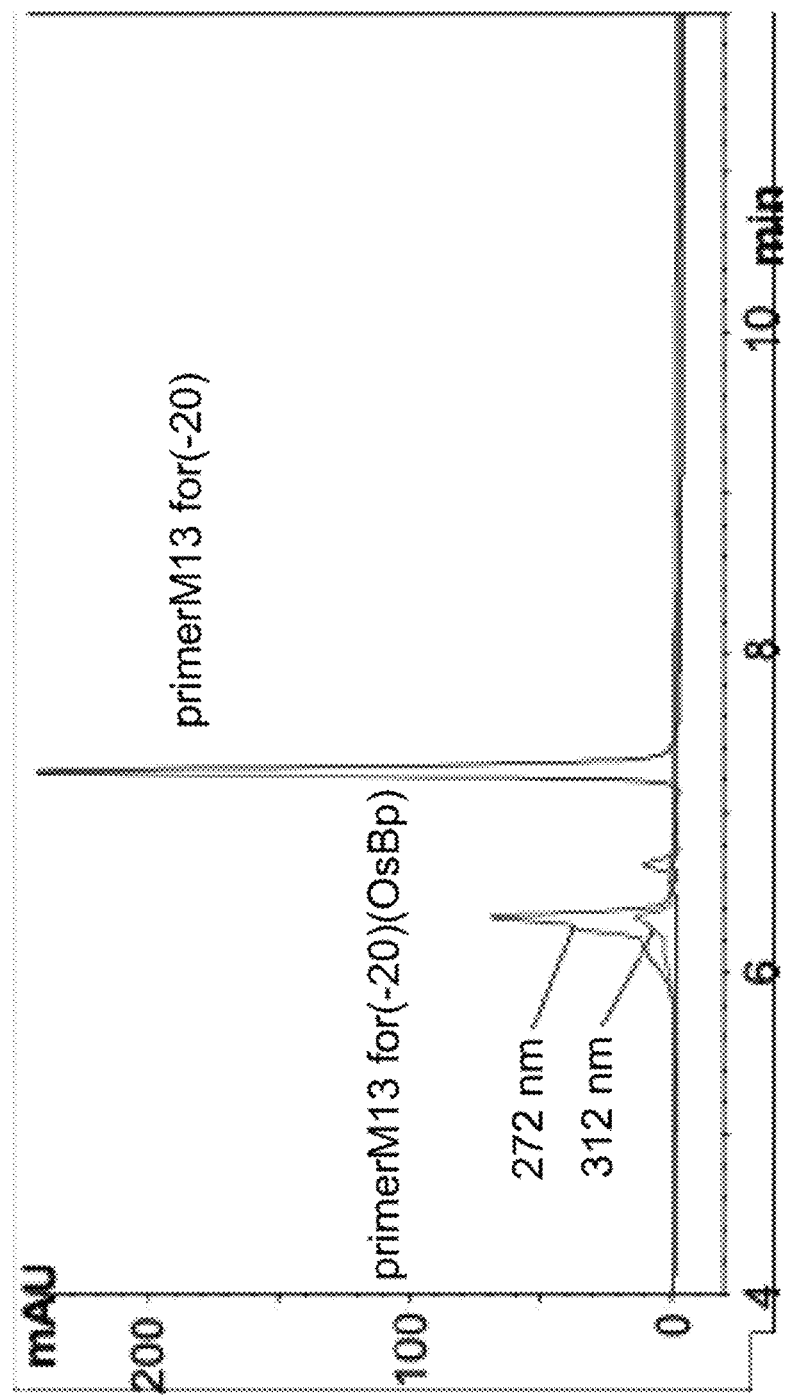
Figure 15B:
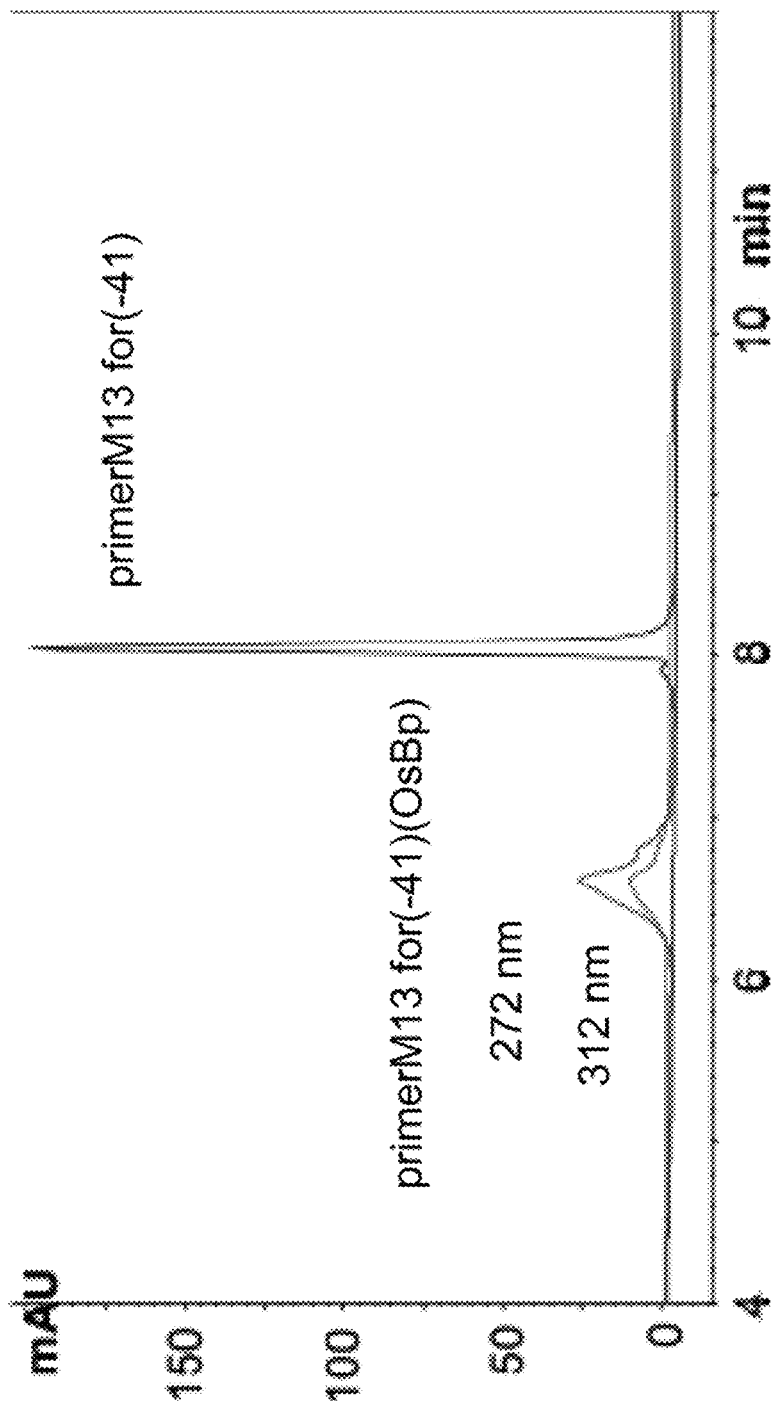
Figure 15C:
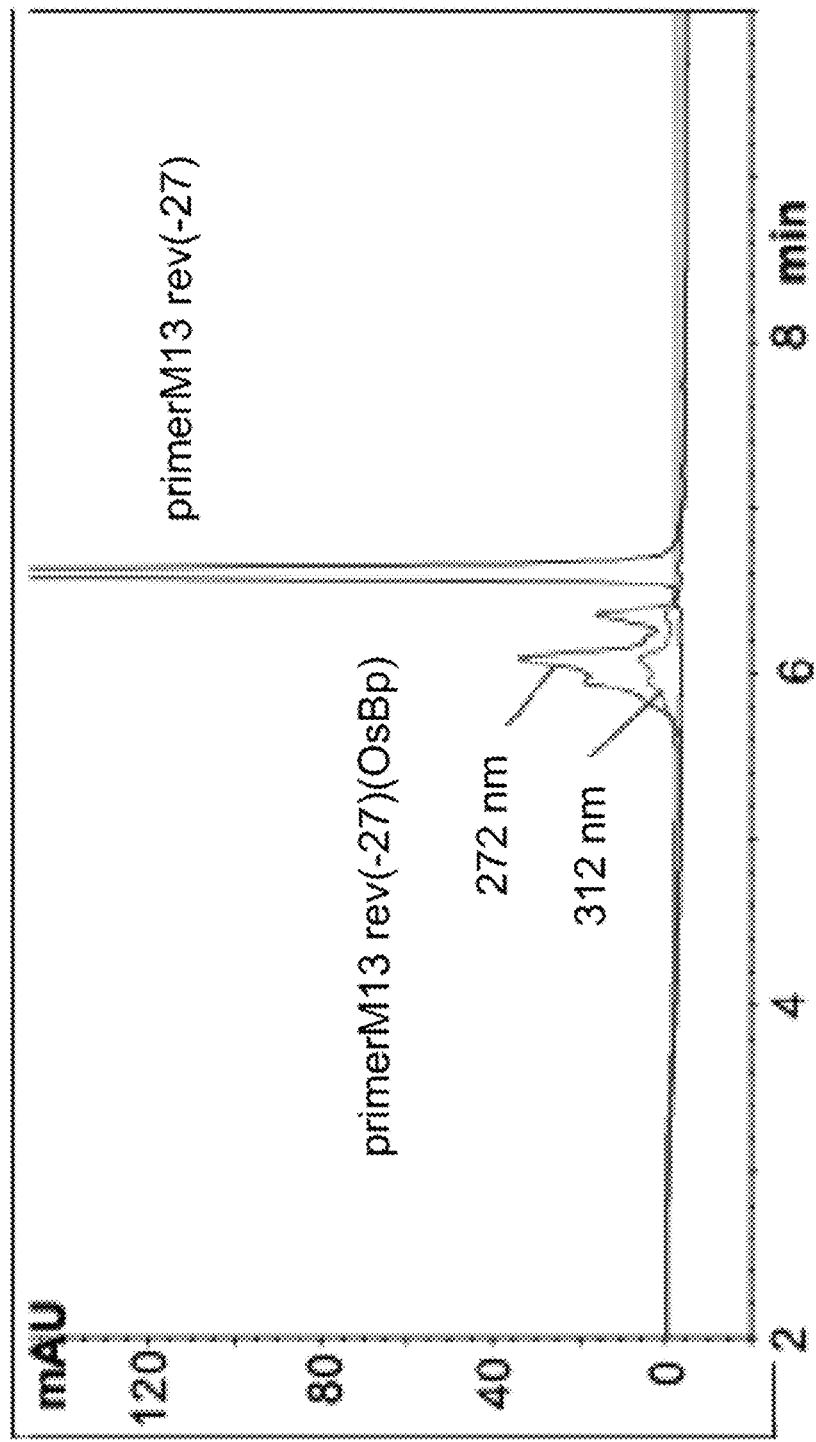
Figure 15D:
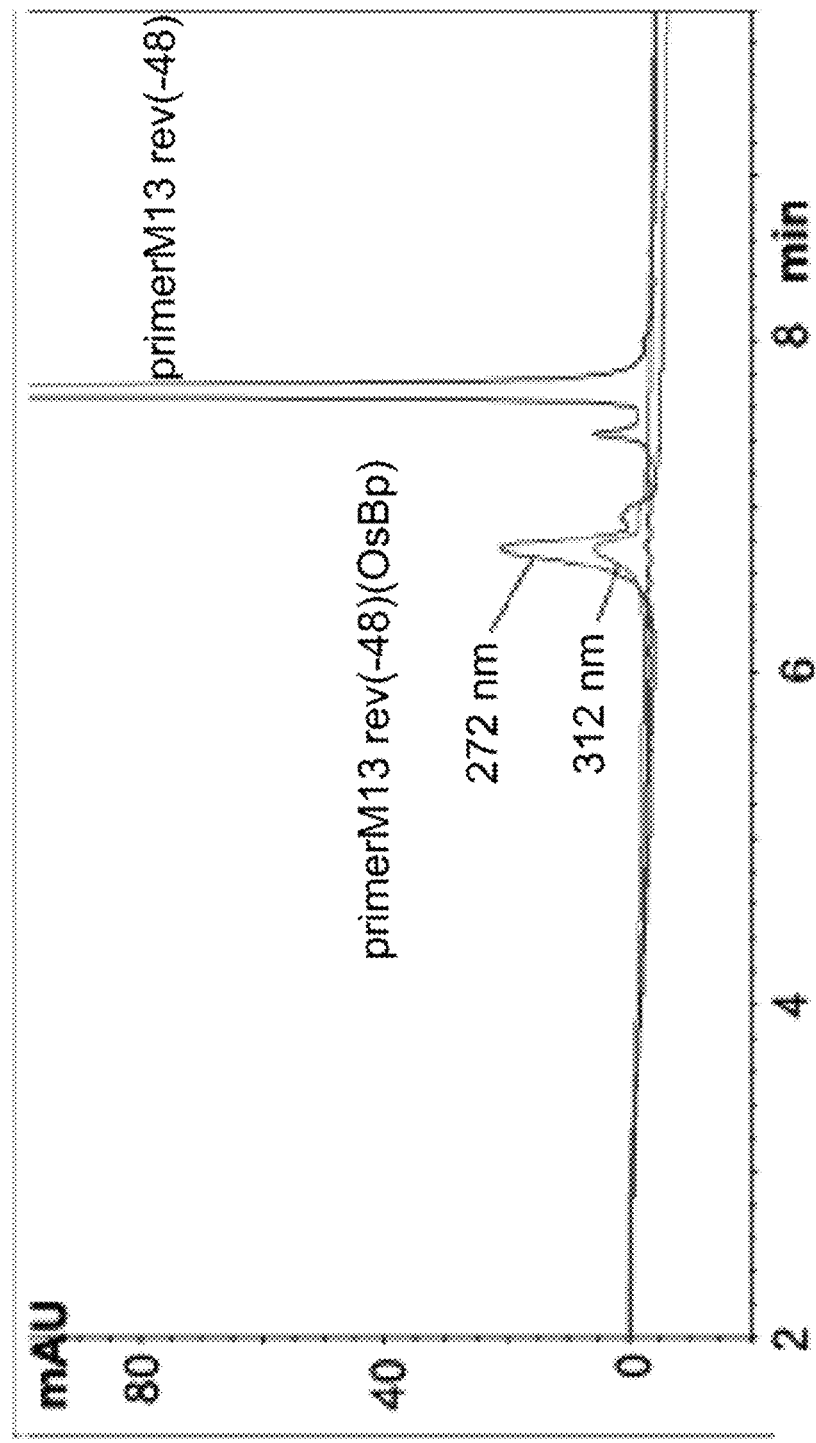
Figure 16A:
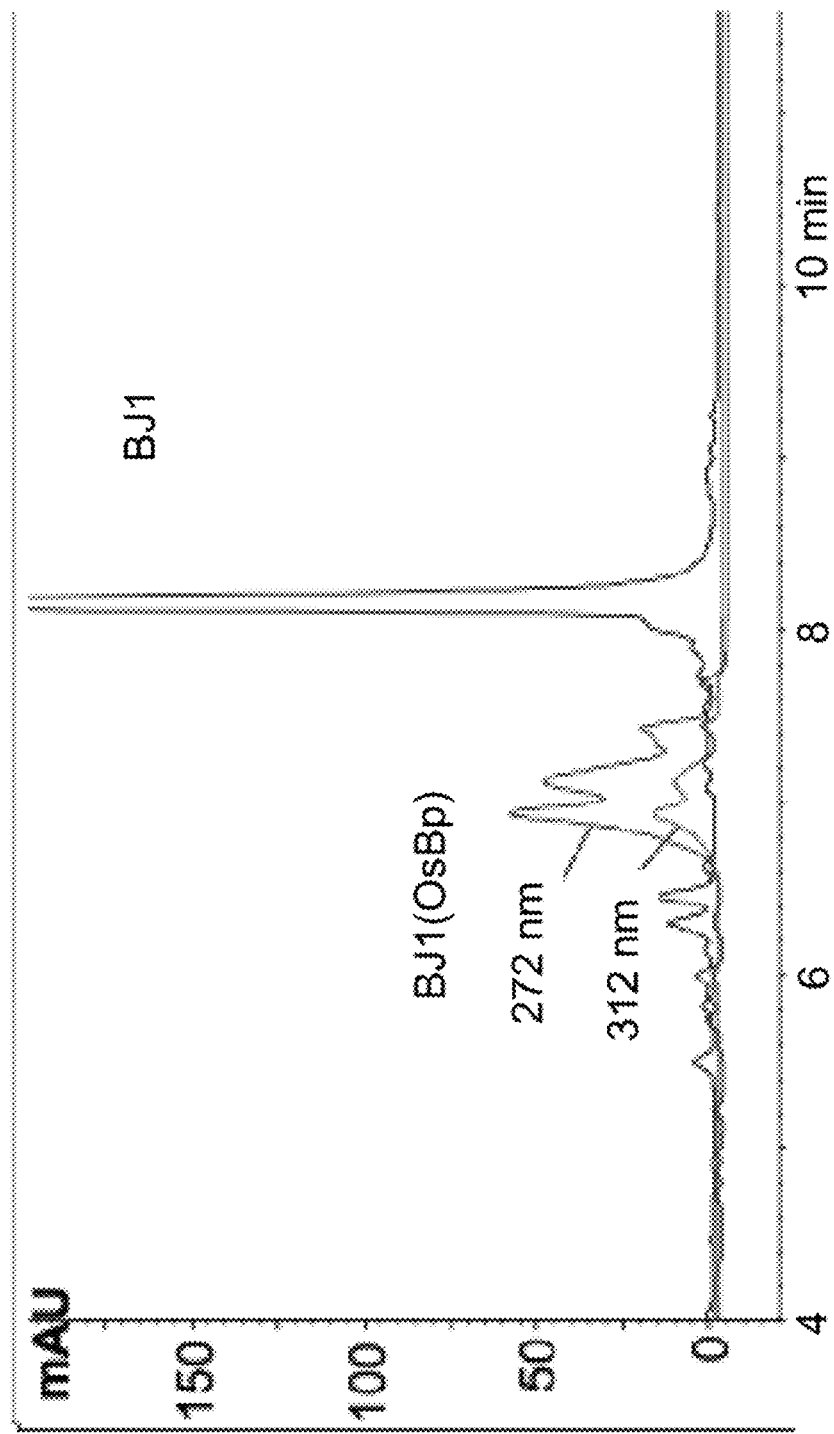

FIG. 14. A good linear correlation was obtained for the number of osmylated pyrimidines in an oligo, which is missing Ts, as a function of the number of U in a sequence. The correlation does not appear to depend heavily on whether or not the sequence is a DNA, RNA or carries 2'-OMe groups on all or on a portion of the bases (See Table 1). The linear correlation may be used to estimate the number of osmylated pyrimidines per protocol c for any given sequence. The linear correlation is attributed to the observation that deoxyuridine (dU) is osmylated 4.7-times faster compared to deoxycytidine (dC) (Ding, Y. & Kanavarioti, A. (2016)), and to the conditions of protocol c that yield only a small percentage of osmylated pyrimidines, and not a practically 100% osmylated oligo.

FIG. 15A-D. HPLC profiles of the four intact M13 primers and their corresponding T-osmylated derivatives, using HPLC method A (see Examples). Analysis of oligos in water as the sample solvent. T-osmylation of these oligos was conducted using protocol o (see Examples). The reason osmylated oligos appear as multiple peaks is because top or bottom addition of OsBp to the C5-C6 double bond leads to topoisomers, that this chromatography resolves.

FIG. 16A-D. HPLC profiles of the four intact BJ1-4 and their corresponding T-osmylated derivatives using HPLC method A. Analysis of oligos in water as the sample solvent. T-osmylation of these oligos was conducted using protocol o (see Examples).

Figure 17A:
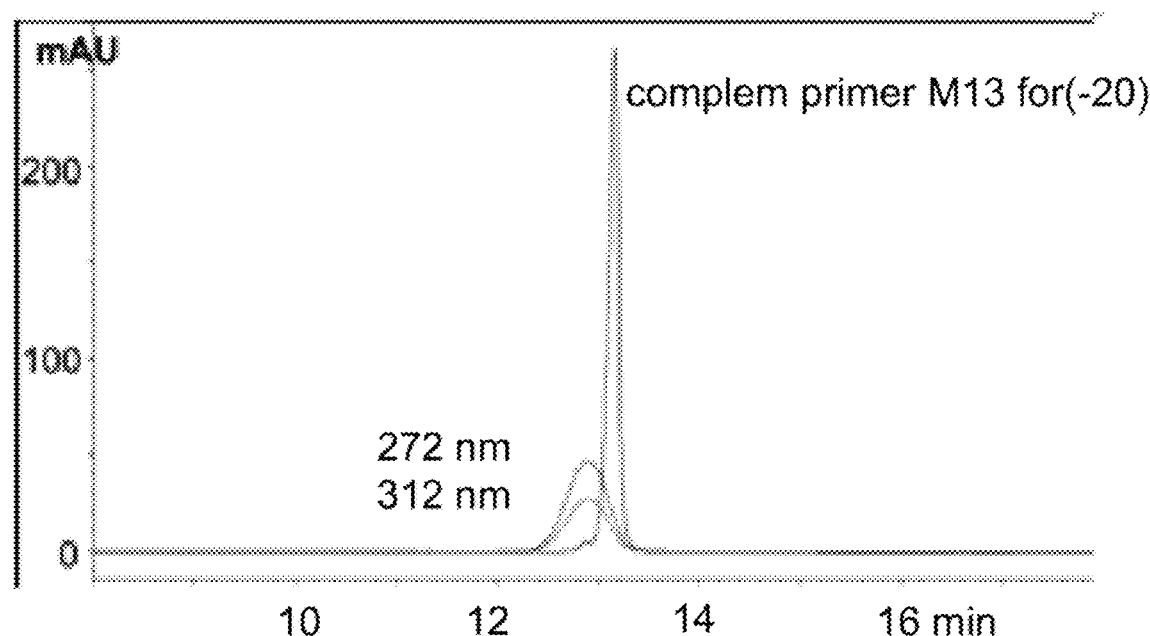
Figure 17B:
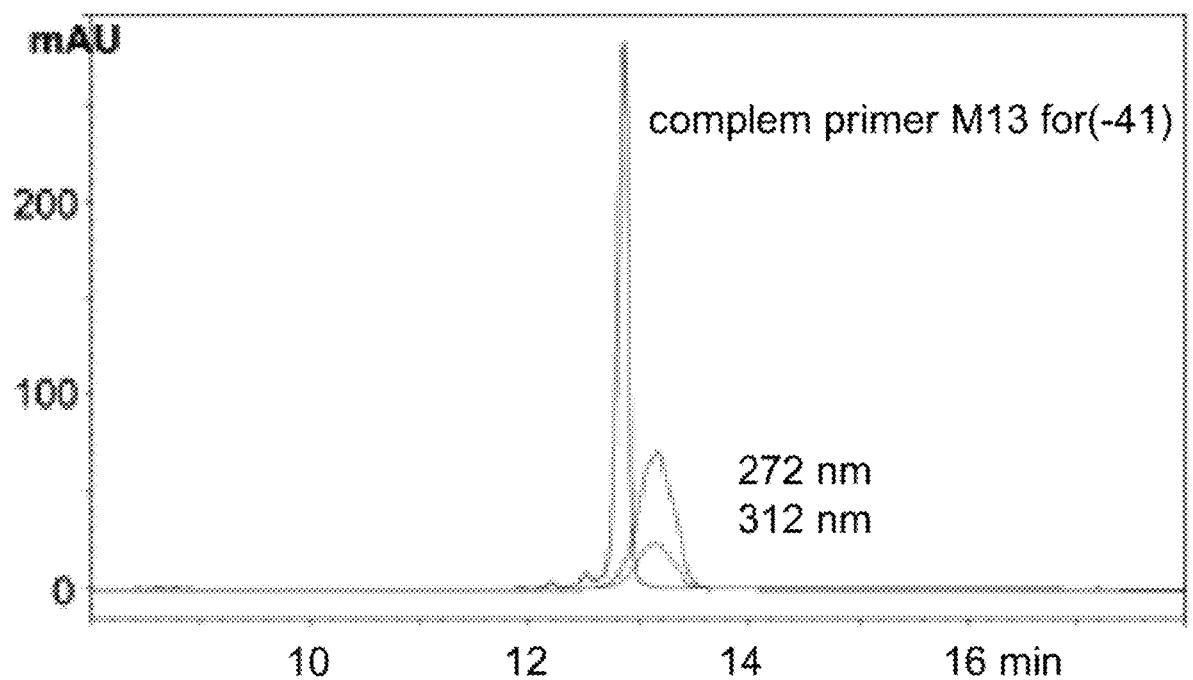
Figure 18A:
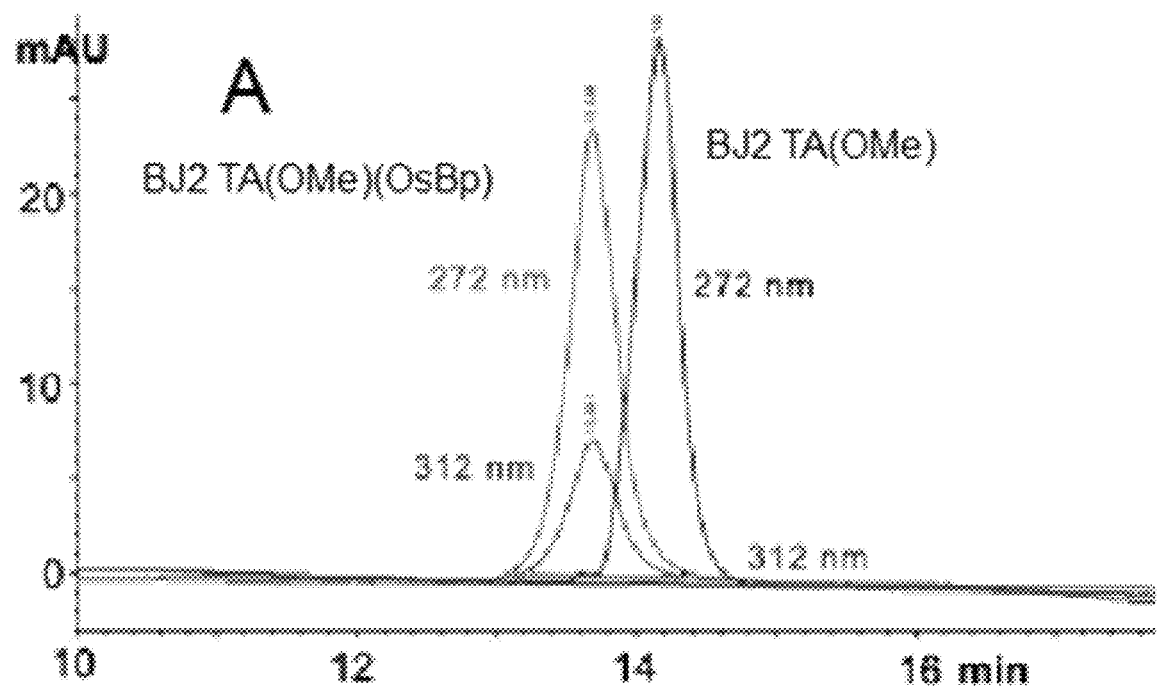
Figure 18B:
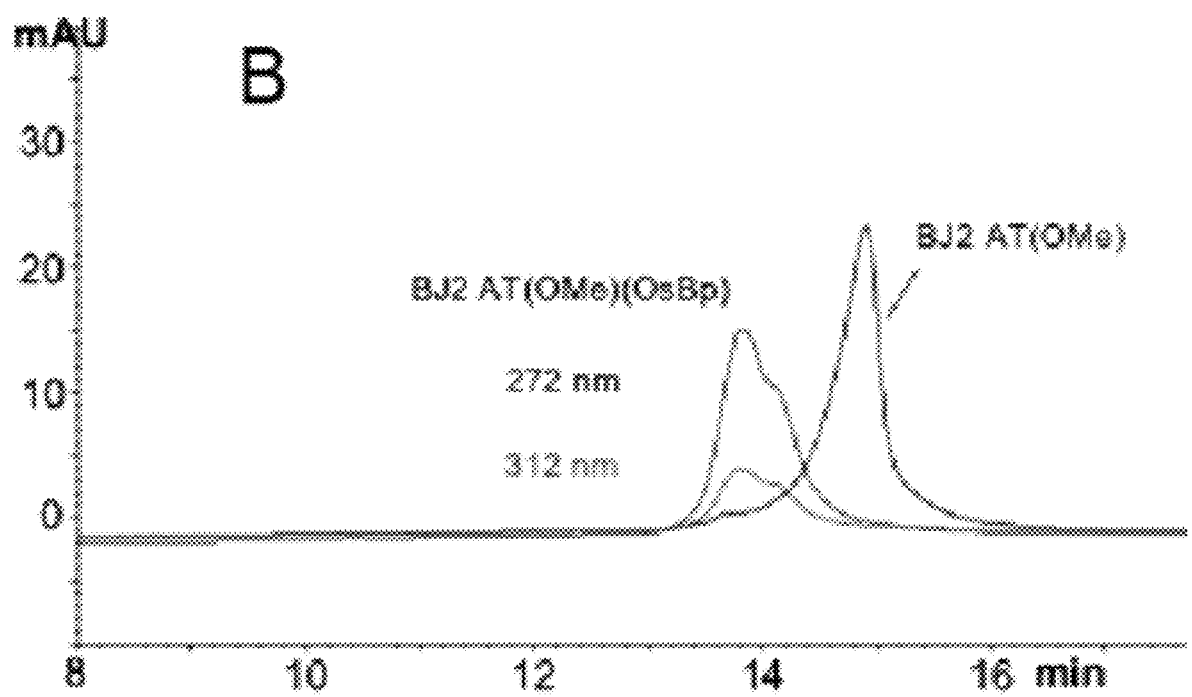
Figure 18C:
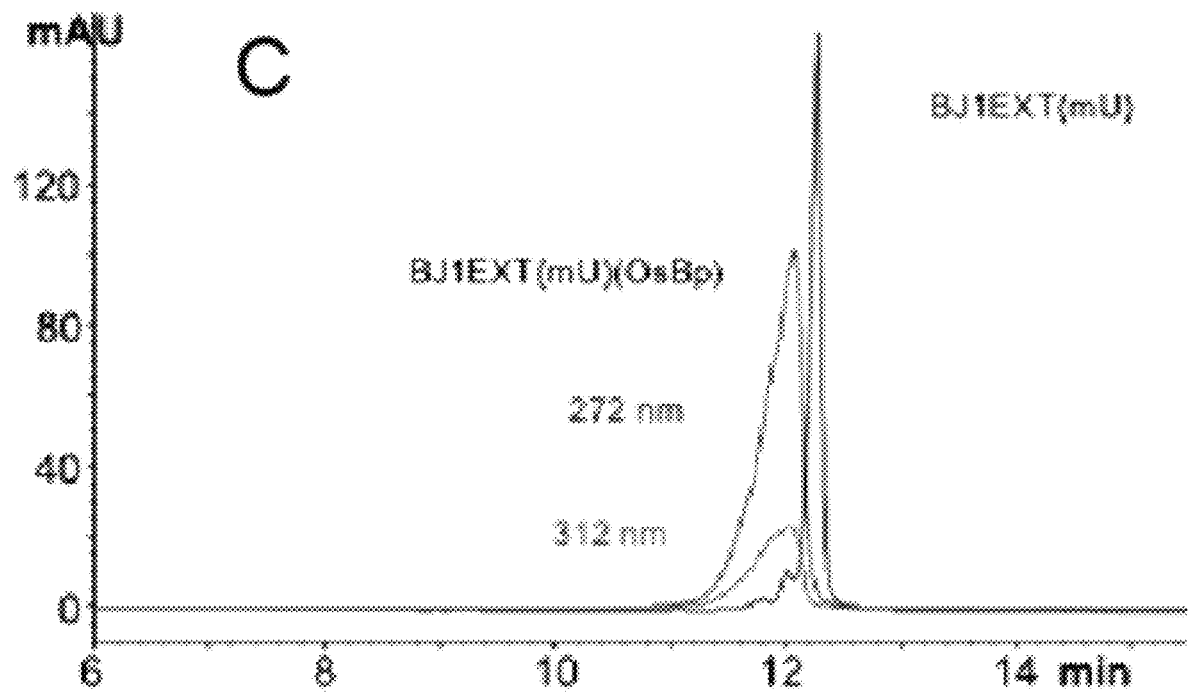
Figure 18D:
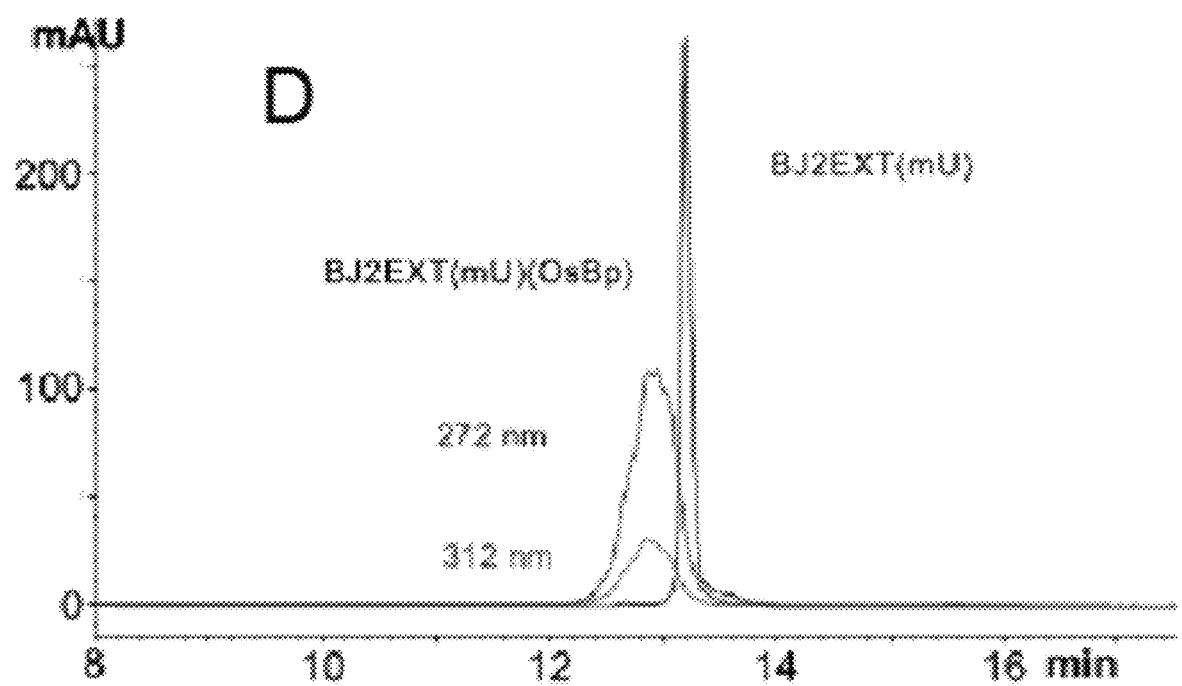
Figure 19A:
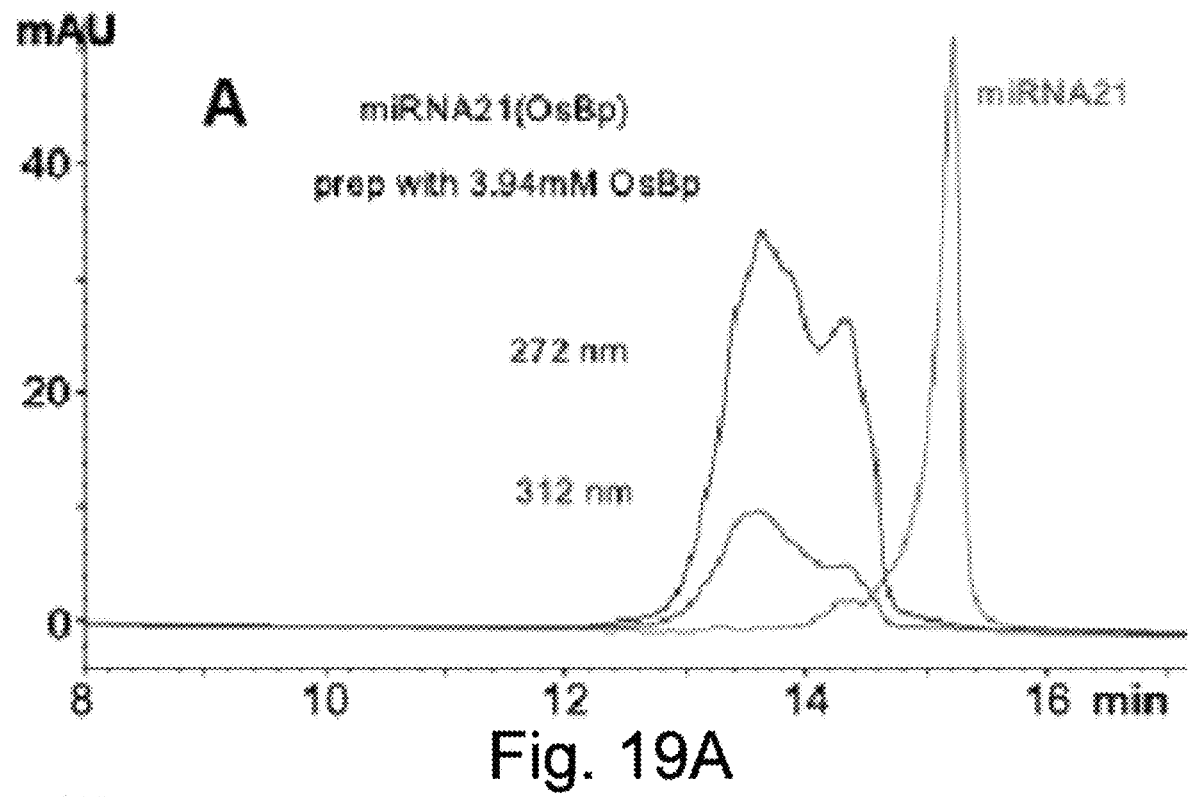
Figure 19B:
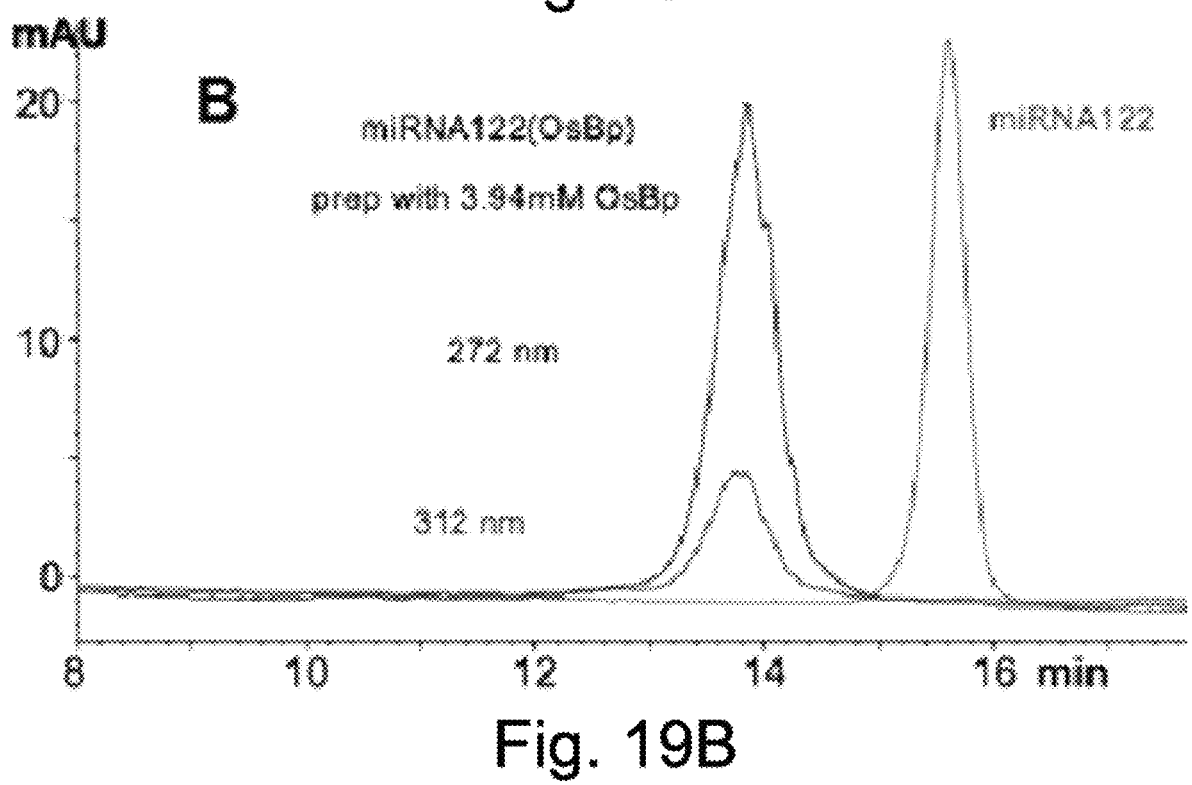
Figure 19C:
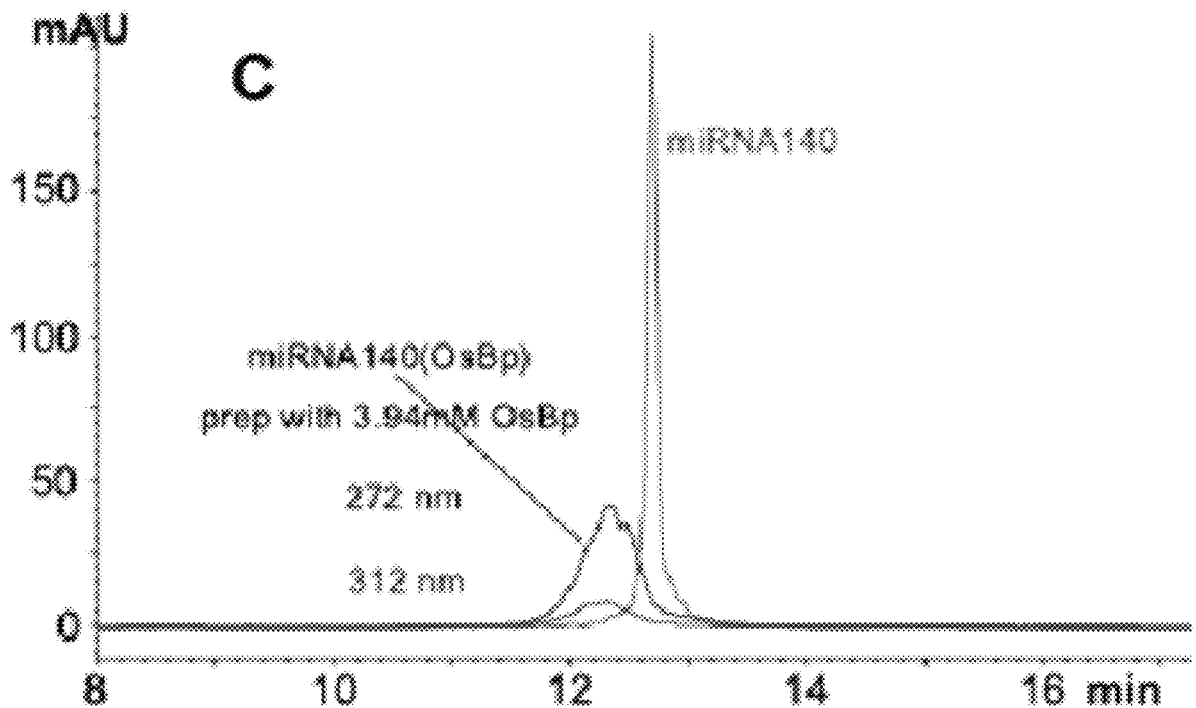
Figure 19D:
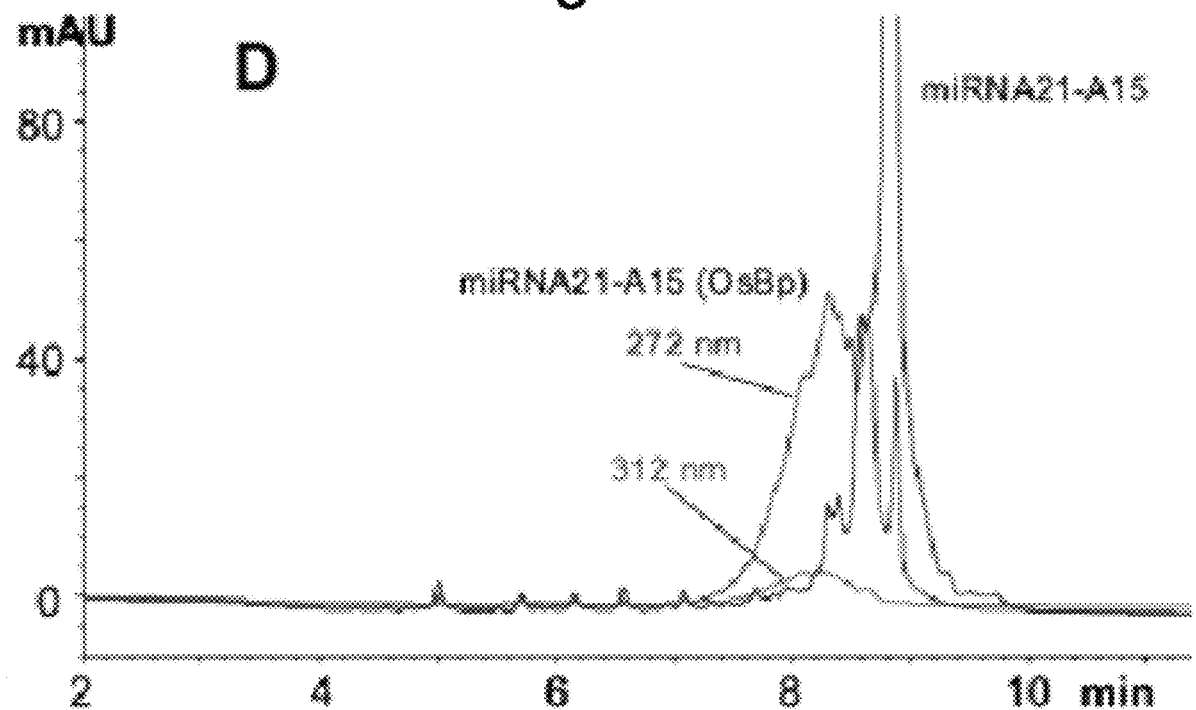

FIG. 17A,B. HPLC profiles of the 2 intact complements of primerM13for(−20) (FIG. 17A) and primerM13for(−41) (FIG. 17B) shown at 260 nm, and their corresponding T-osmylated derivatives shown at 272 nm and 312 nm using HPLC method B (see Examples). Analysis of oligos in water as the sample solvent. Briefly HPLC Method B is using the DNA PacPA200 HPLC column from ThermoFisher Scientific at the 2×250 mm configuration with 0.45 mL/min flow and 15° C. column compartment. Solvents are aqueous pH 8.0±0.2 mobile phases A (MPA) and mobile phase B (MPB) with 25 mM TRIS.HCL buffer; MPB is 1.5 M NaCl. Initial conditions are 90% MPA-10% MPB, and the gradient is from 10% to 50% MPB in 20 min. The total analysis time including column equilibration is 30 min. T-osmylation of these oligos was conducted using protocol o (see Experimental Section). Right profile shows an atypical, but confirmed result, namely an osmylated conjugate that elutes later compared to the parent intact nucleic acid.

Figure 4A:
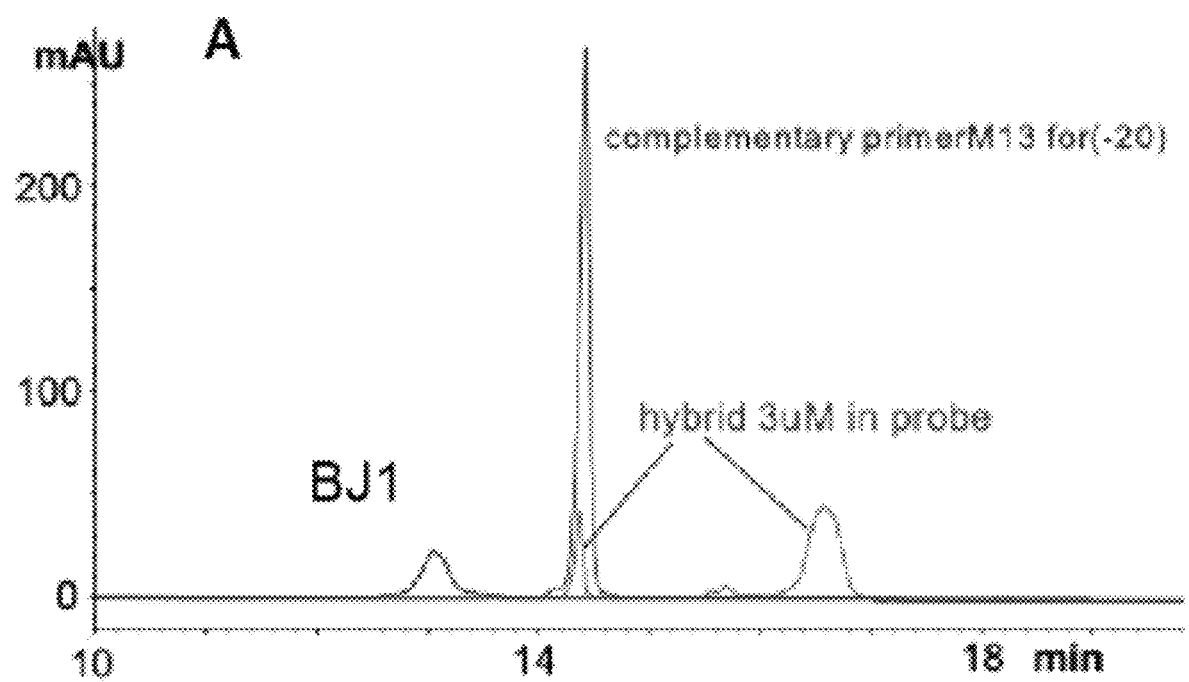

FIG. 18A-D. HPLC profiles of BJ2 TA(OMe) (FIG. 18A) and BJ2 AT(OMe) (FIG. 18B), as well as BJ1EXT(mU) (FIG. 18C) and BJ2EXT(mU) (FIG. 18D) shown at 260 nm and their corresponding T-osmylated derivatives shown at 272 nm and 312 nm (sequences in Table 1). HPLC profiles obtained with HPLC method B (see FIG. 17A,B and Examples). Materials in water as sample solvent. A nanopore experiment conducted with probe BJ2 TA(OMe) indicated excellent translocation properties with numerous counts at a relatively low probe load (FIG. 4D).

FIG. 19A-D. HPLC profiles of the intact miRNA21, miRNA122, miRNA140 and miRNA21-A15 (these are the −5p sequences) shown at 260 nm and their corresponding partially osmylated derivatives: different materials are analyzed at different sample load. Osmylation protocol o was used for miRNA21-A15 and protocol c for the other 3 miRNAs (see Table 1 and Examples). HPLC method A used for the analysis of miRNA21-A15 and HPLC method B for analysis of the other 3 miRNAs (see Examples). Materials in water as the sample solvent.

Figure 20A:
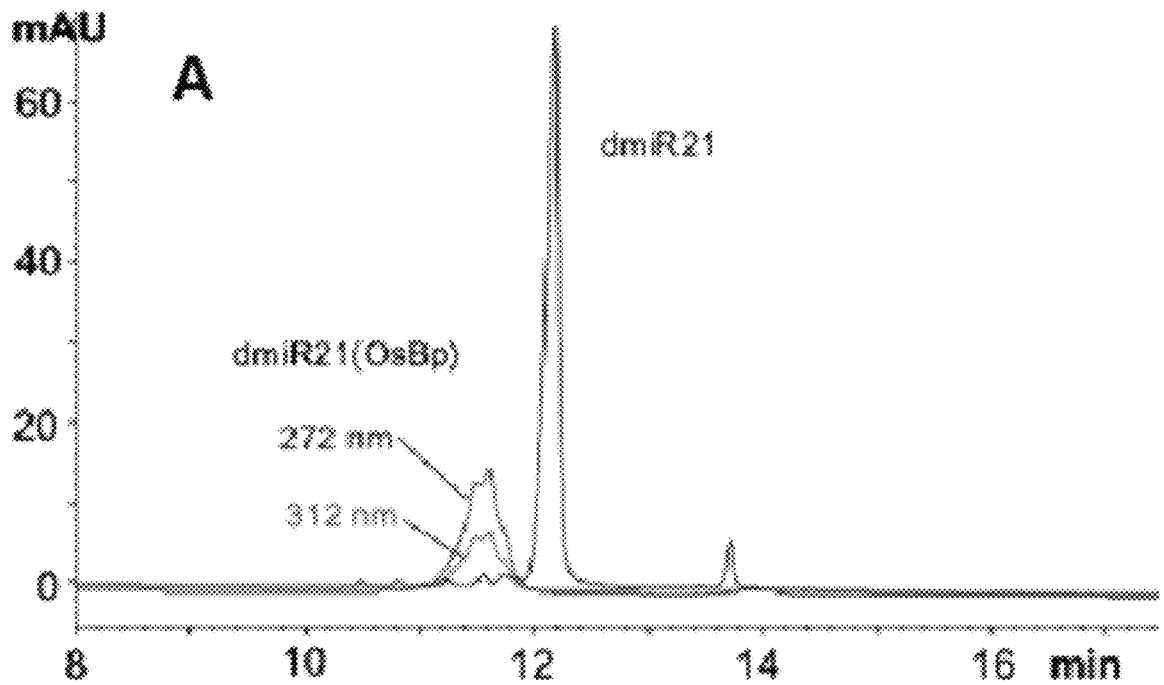
Figure 20B:
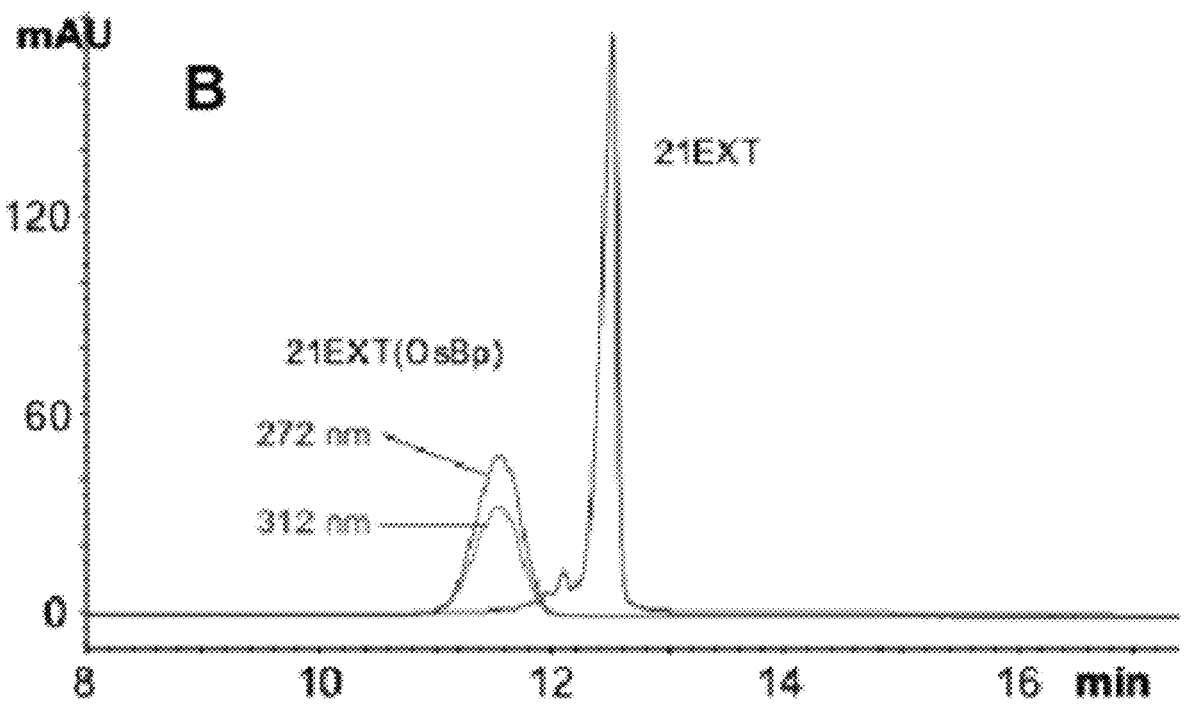

FIG. 20A,B. (FIG. 20A) HPLC profiles of intact dmiR21 at 260 nm and the T-osmylation product at 272 nm and 312 nm. (FIG. 20B) HPLC profiles of intact 21EXT and its T-osmylation product. Osmylation was carried out using protocol o 40 min with 2.63 mM OsBp, earlier process where bipy was dissolved after adding OsO4 (see Examples). Materials in water for analysis, and analysis was done using HPLC method B (see Examples).

Figure 6B:
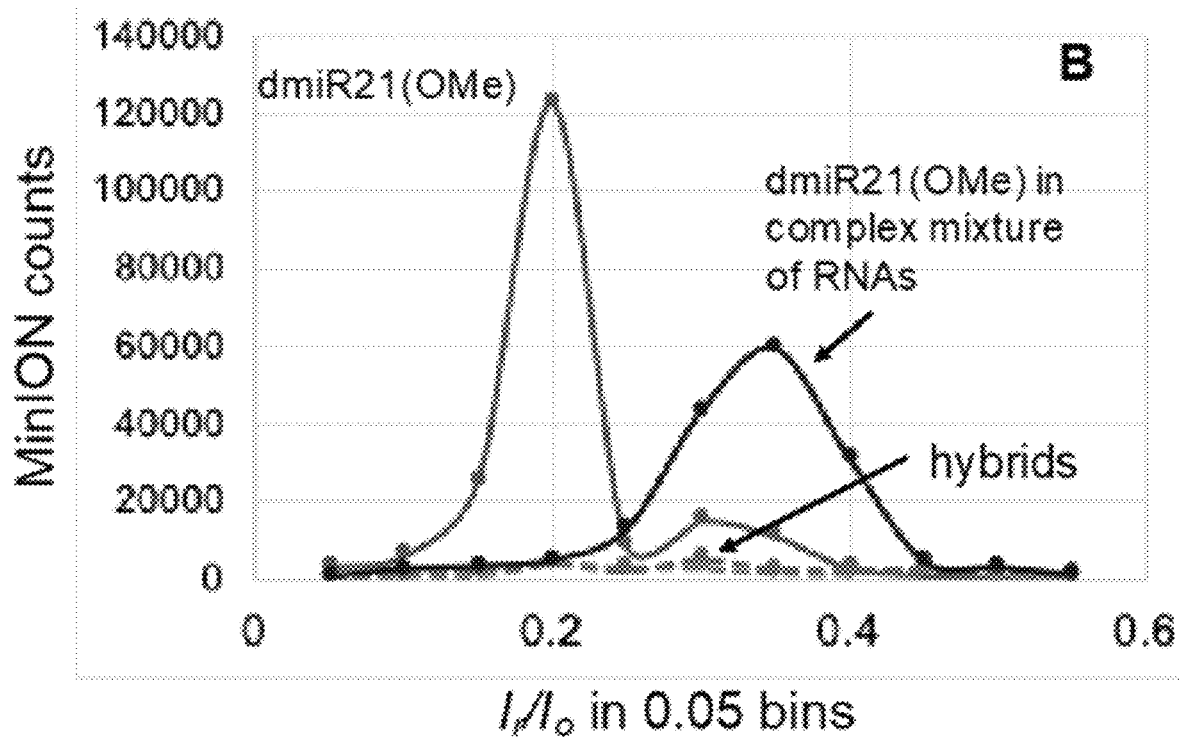
Figure 21A:
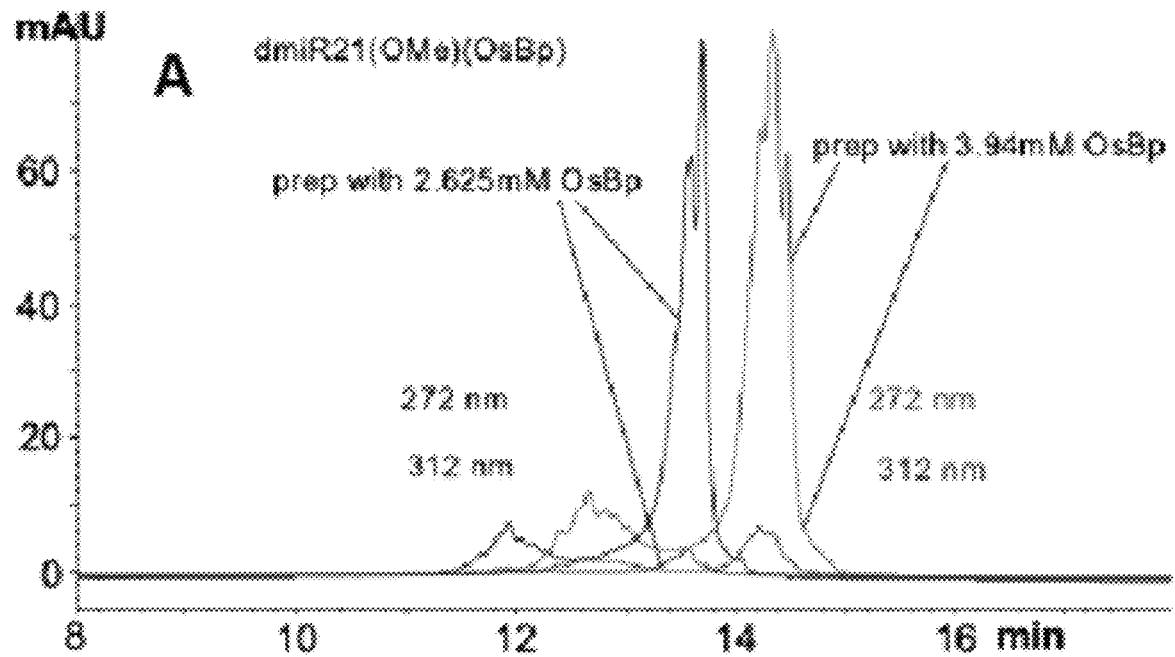
Figure 21B:
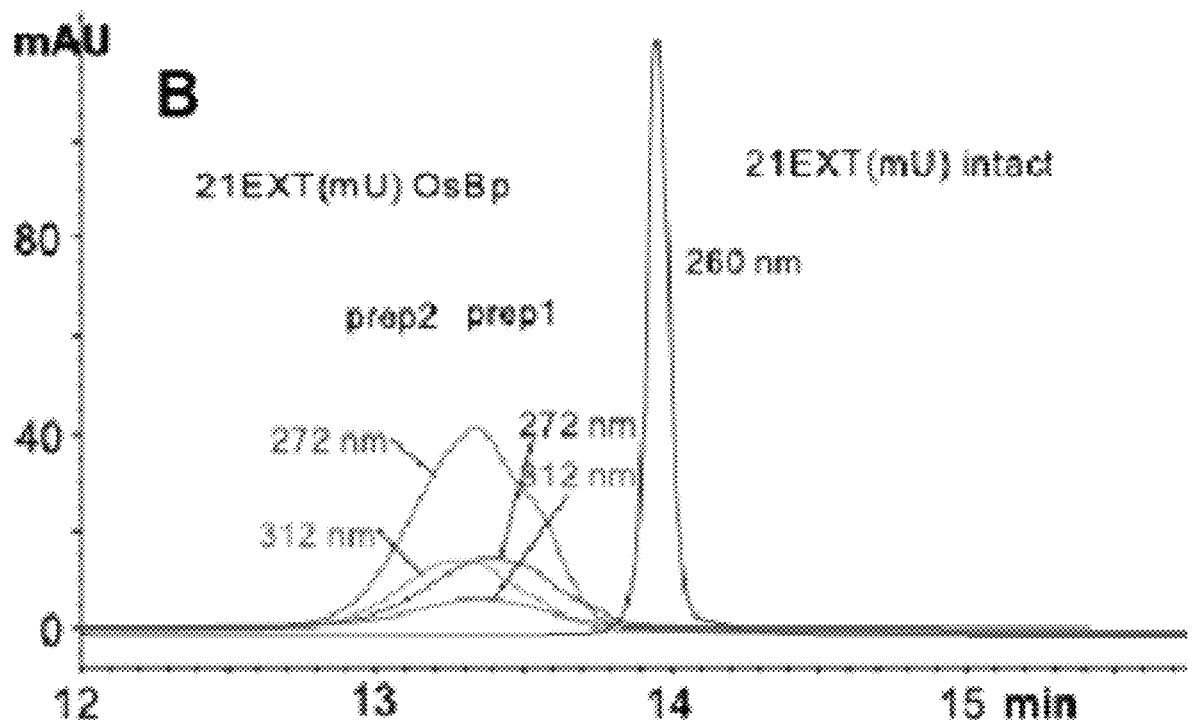
Figure 21C:
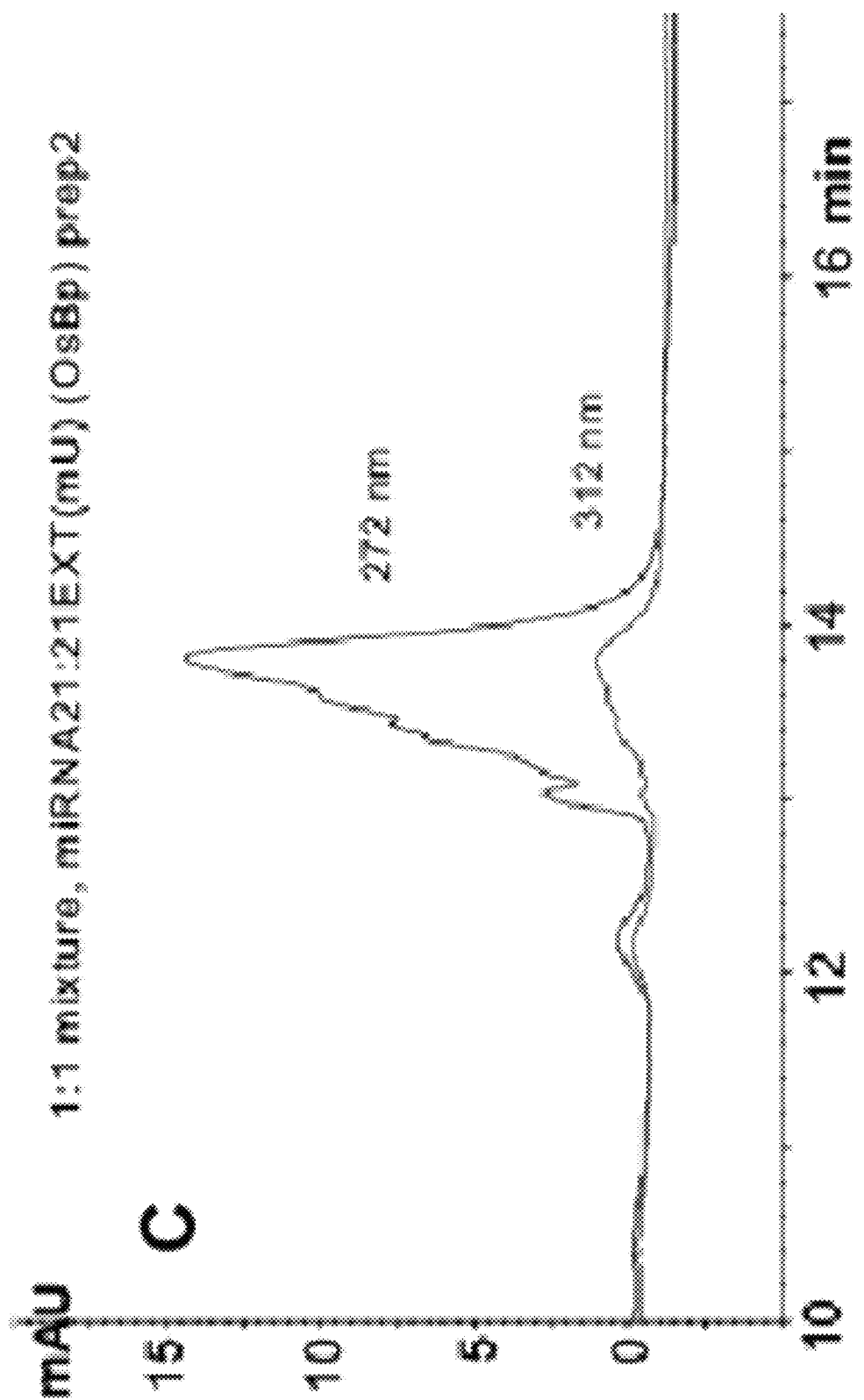
Figure 22A:
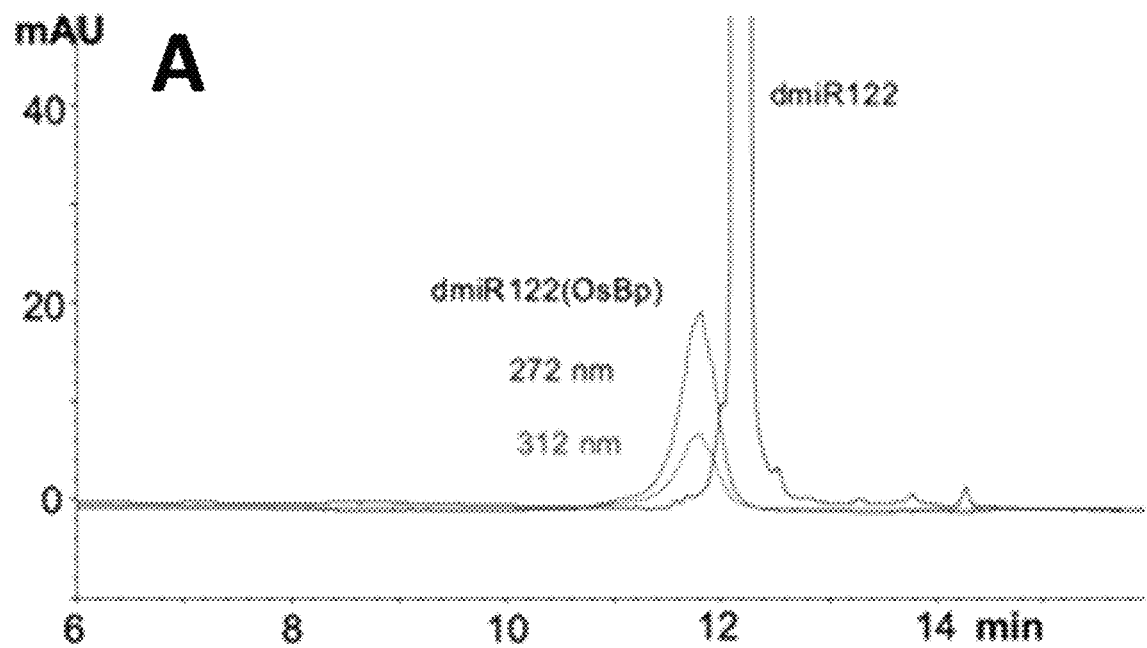
Figure 22B:
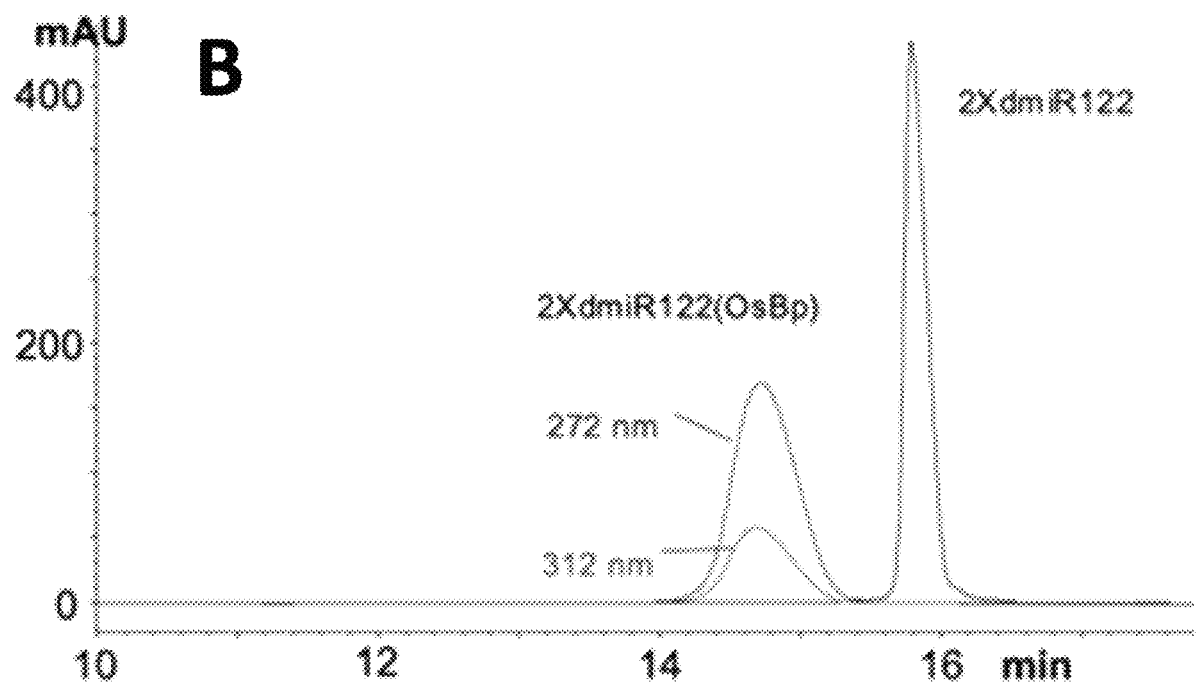
Figure 22C:
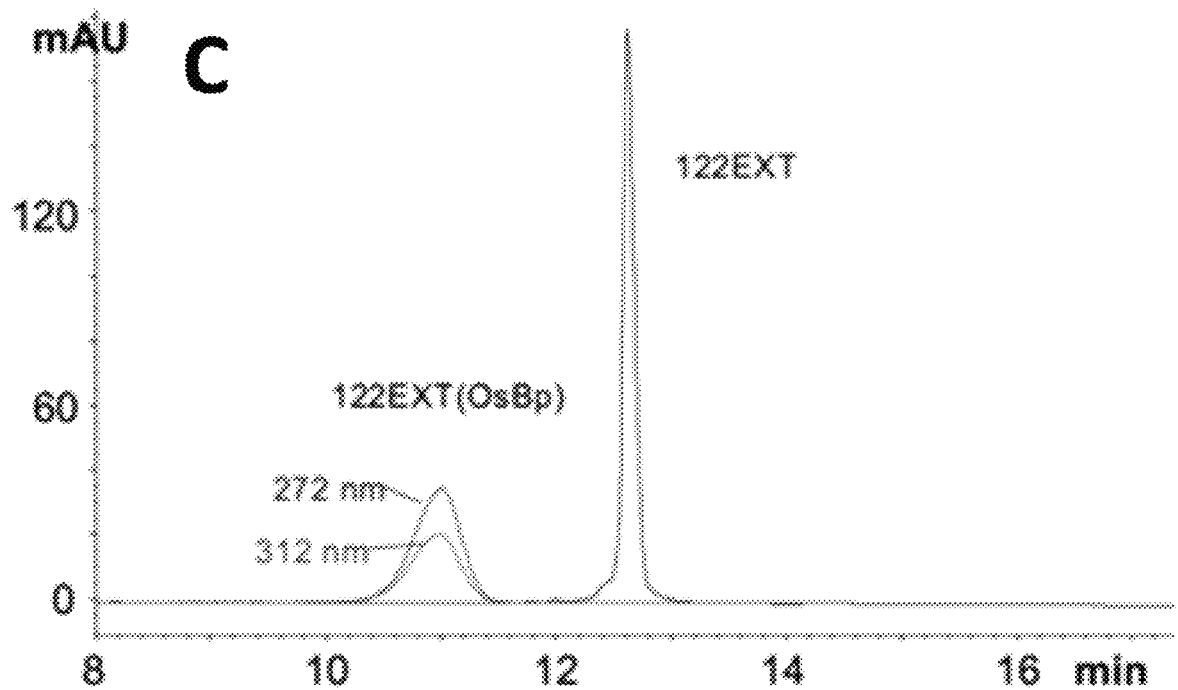
Figure 22D:
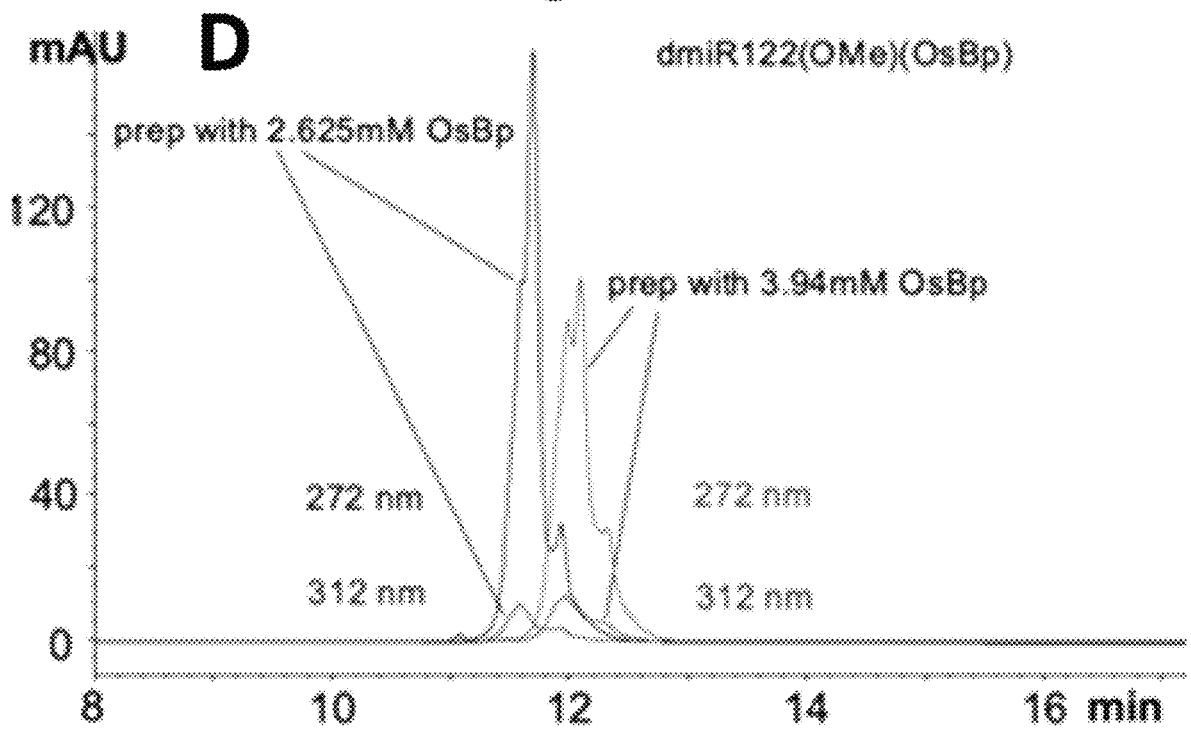

FIG. 21A-C. (FIG. 21A) HPLC profiles of the osmylation products of dmiR21(OMe) using protocol b 30 min with 2.63 mM OsBp and protocol c 30 min with 3.94 mM OsBp. A third protocol (d) with 30 min incubation using 5.25 mM OsBp was used to osmylate this probe for the nanopore experiment (FIG. 6B). This was necessary because dmiR21 (OMe) contains no Ts, and using protocols b and c results in very low levels of osmylation and diminished detectability. (FIG. 21B) probe 21EXT(mU) intact and its osmylation products with the two different protocols; prep1, using protocol a 45 min with 2.63 mM OsBp and prep2 protocol b 30 min with 2.63 mM OsBp. (FIG. 21C) repeat of FIG. 7C in order to compare the HPLC profile of the hybrid with the HPLC profile of the probe alone (B, above) and see that they are distinct. Analysis was done using HPLC method B (see Examples).

FIG. 22A-D. HPLC profiles of the intact miRNA122 probes shown at 260 nm and their corresponding T-osmylated derivatives (the actual probes) at 272 and 312 nm. Osmylation protocol o was used to osmylate dmiR122, 2XdmiR122 and 122EXT. dmiR122(OMe) does not have any T, and was osmylated using protocols b or c (see Table 1 for sequences and for protocols). Materials were in water for analysis and analysis was done using HPLC method B (see Examples).

Figure 23A:
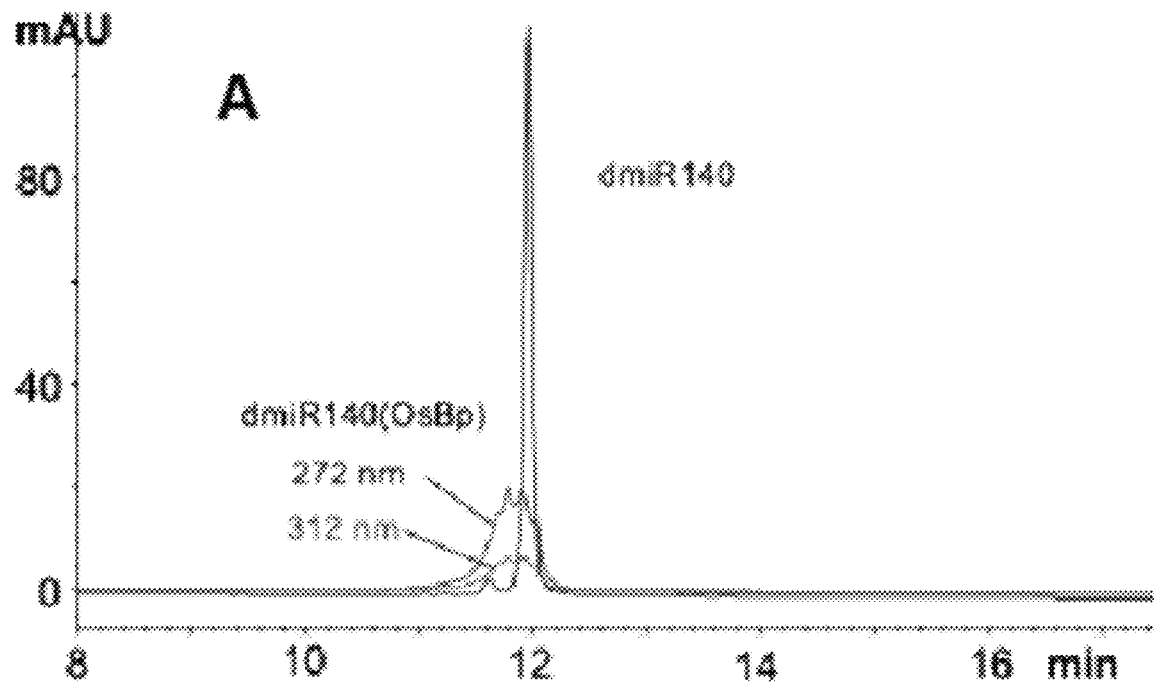
Figure 23B:
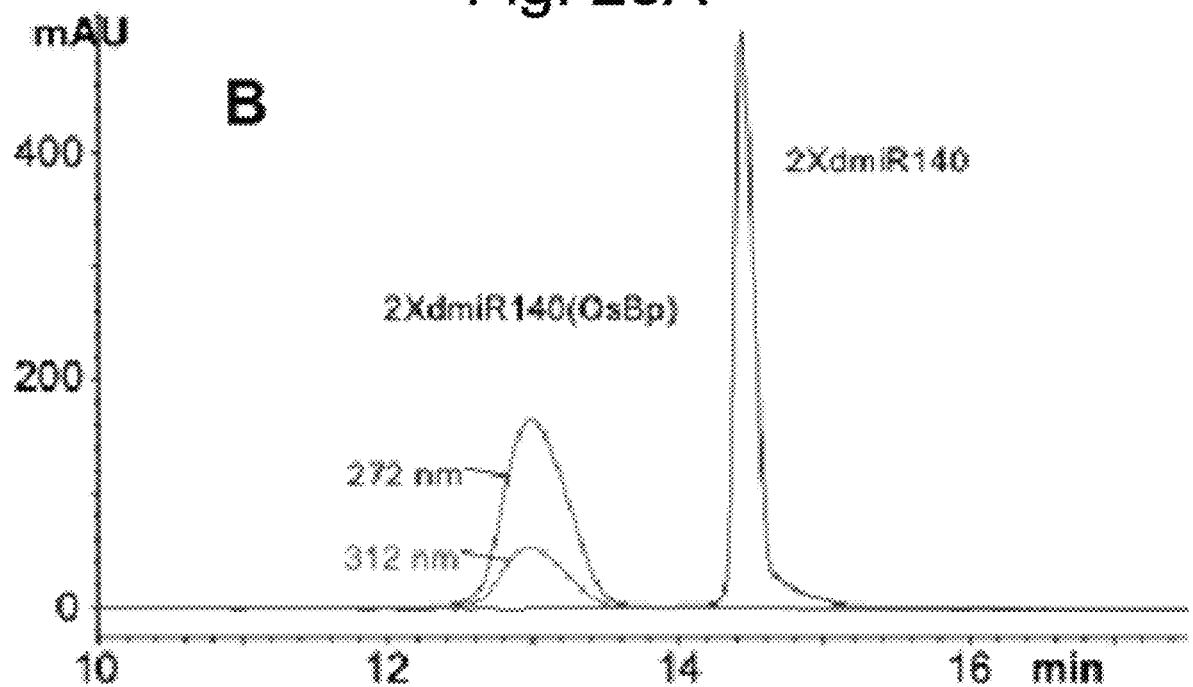
Figure 23C:
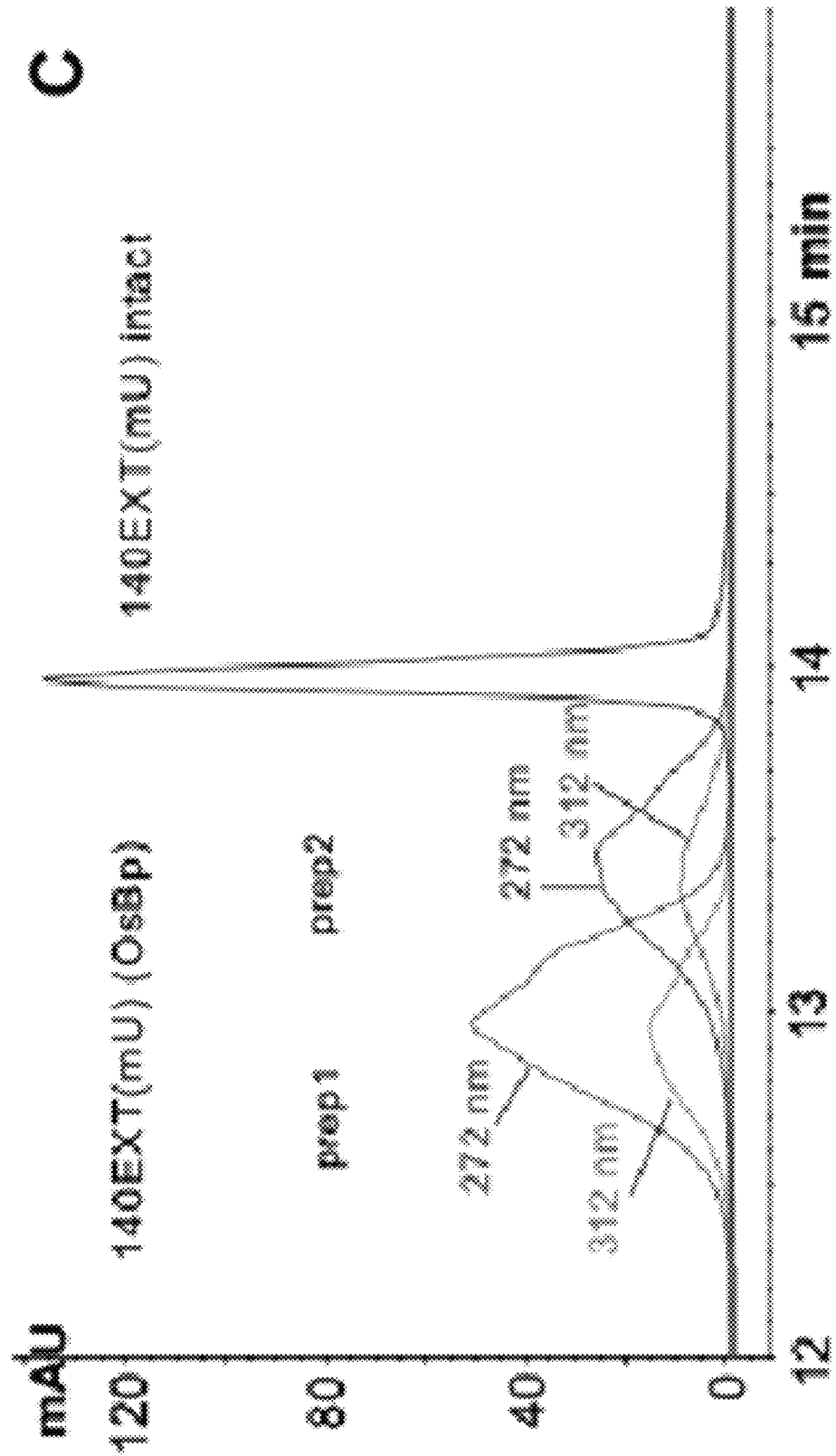

FIG. 23A-C. HPLC profiles of the intact miRNA140 probes shown at 260 nm and their corresponding osmylated derivatives (the actual probes) shown at 272 nm and 312 nm. HPLC profiles with dmiR140 (FIG. 23A) and 2XdmiR140 (FIG. 23B) using osmylation protocol o, 40 min with 2.63 mM OsBp (earlier process, bipy not dissolved prior to OsO4 addition. (FIG. 23C) Probe 140EXT(mU) intact and its osmylation products with the two different protocols; prep2, using protocol a, 45 min with 2.63 mM OsBp, and prep1 protocol b, 30 min with 2.63 mM OsBp. Materials in water for analysis, and analysis was done using HPLC method B (see Examples).

Figure 24A:
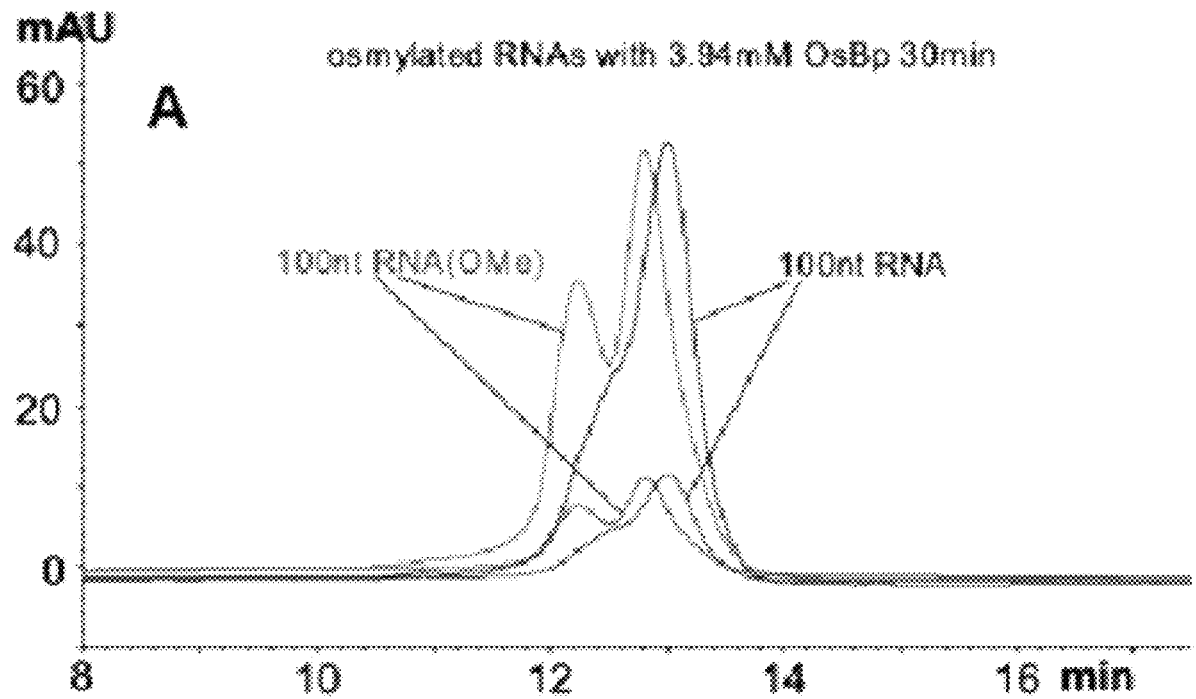
Figure 24B:
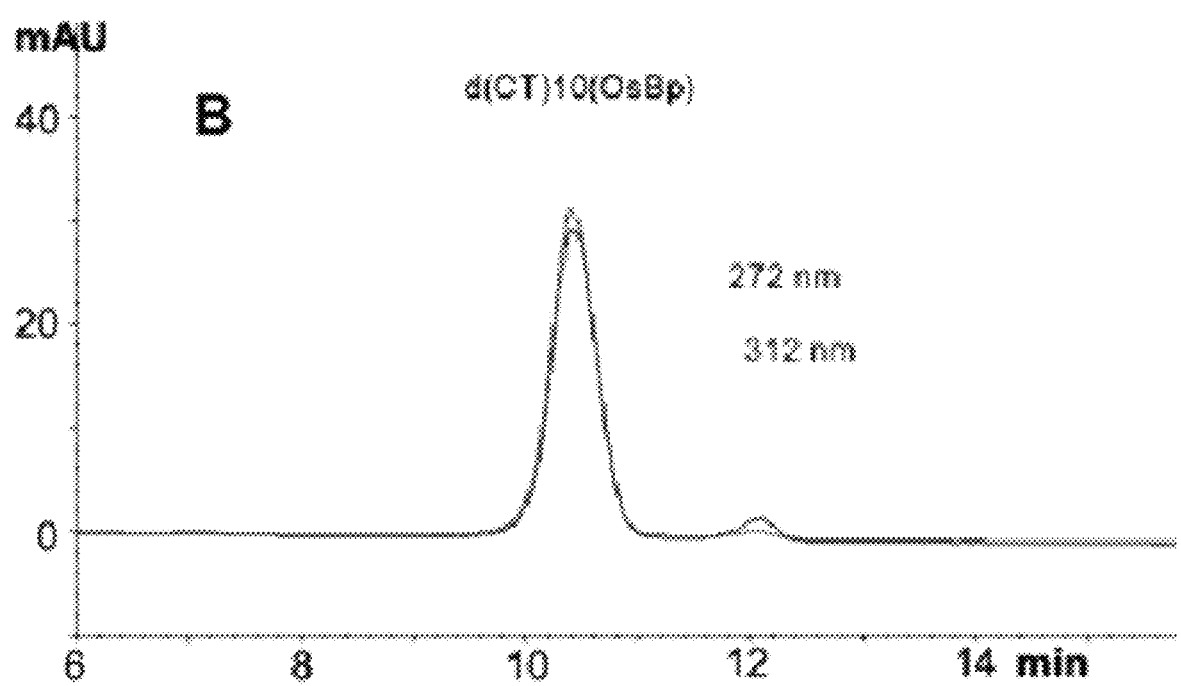

FIG. 24A,B. (FIG. 24A) HPLC profiles of partially osmylated 100 nt RNA and 100 nt RNA(OMe) using osmylation protocol c (see Table 1 and Examples). (FIG. 24B) HPLC profiles of T-osmylated d(CT)10 using protocol b. Materials in water as the sample solvent. HPLC method B was used for all the samples and HPLC profiles are shown at 272 nm and 312 nm. Osmylation protocols and HPLC method can be found in the Examples.

Figure 25A:
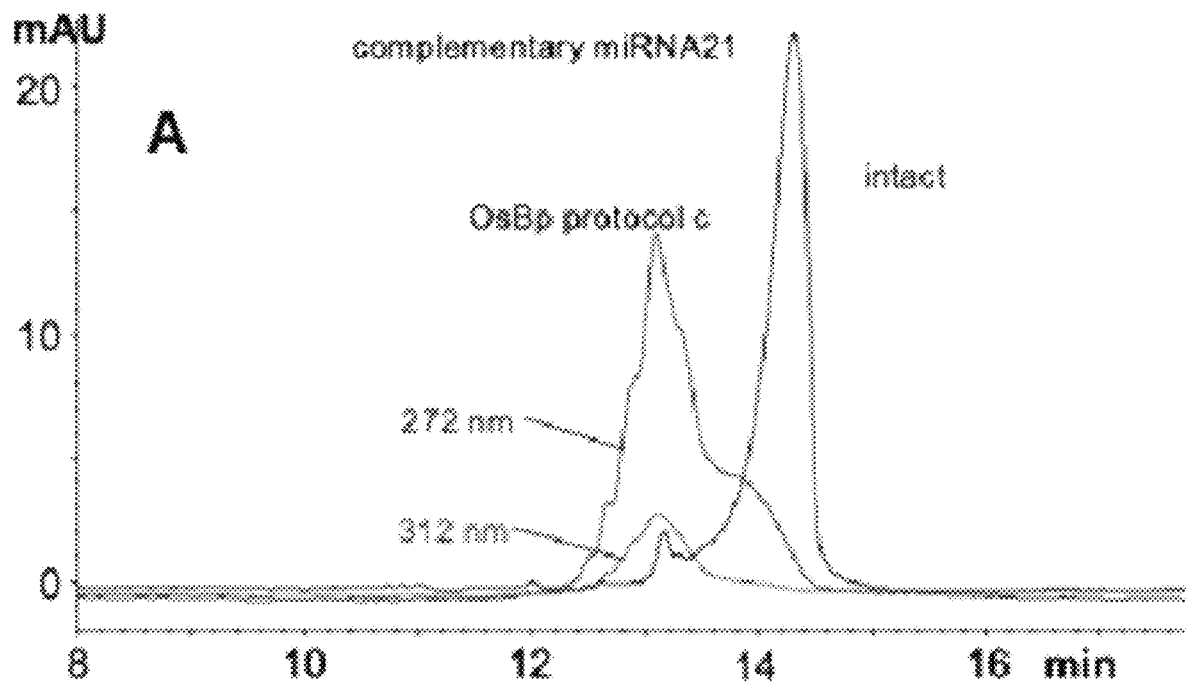
Figure 25B:
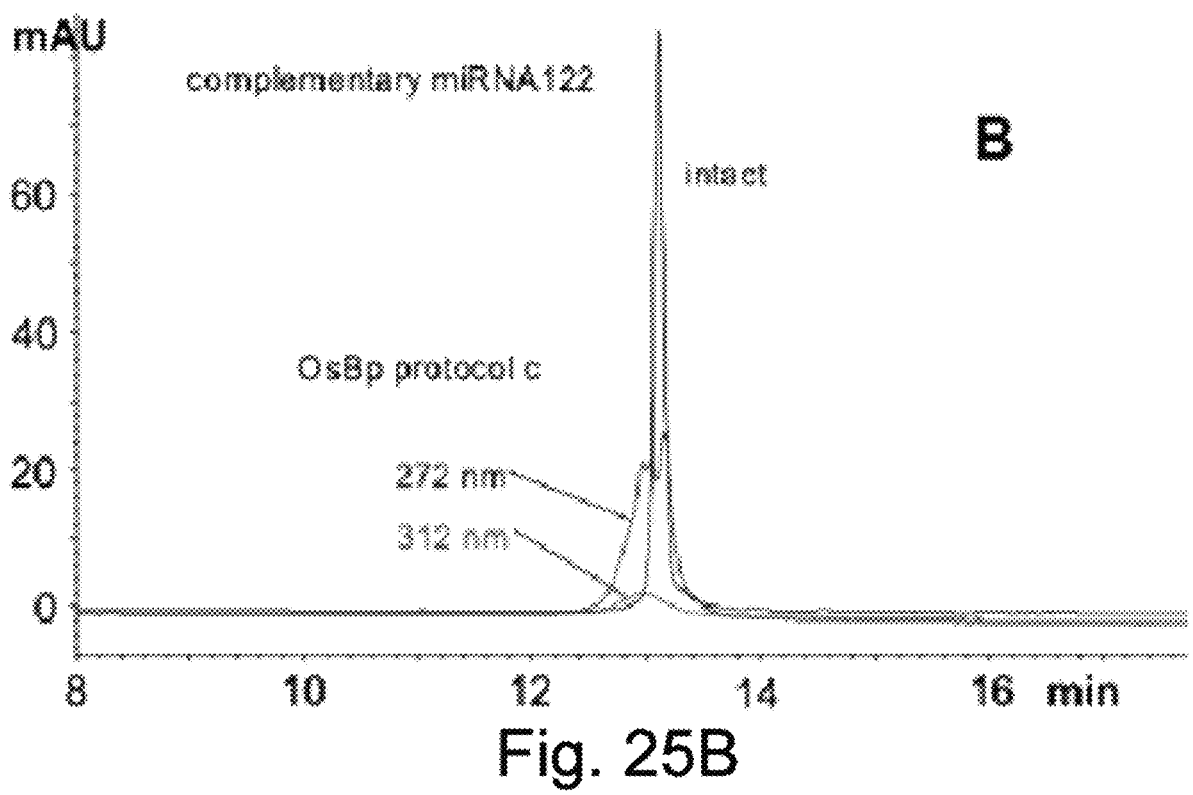

FIG. 25A,B. HPLC profiles of partially osmylated 22 nt RNAs. (FIG. 25A) complementary miRNA21 and (FIG. 25B), complementary miRNA122. Osmylation protocol c was used, 30 min with 3.94 mM OsBp.

Figure 26A:
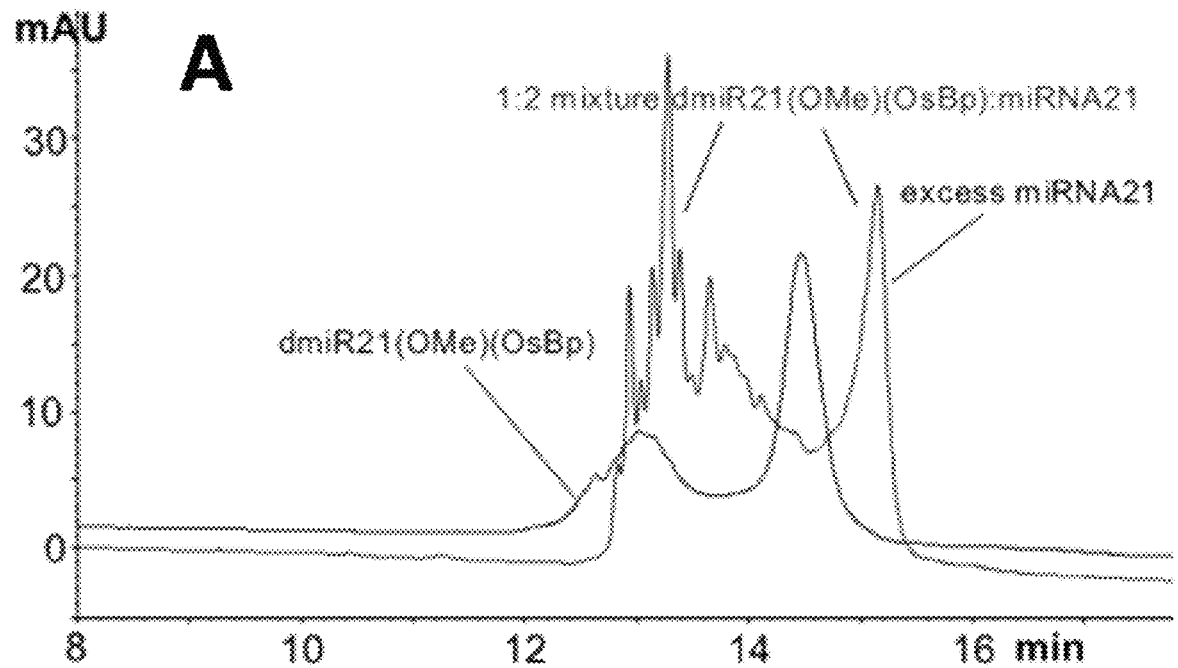
Figure 26B:
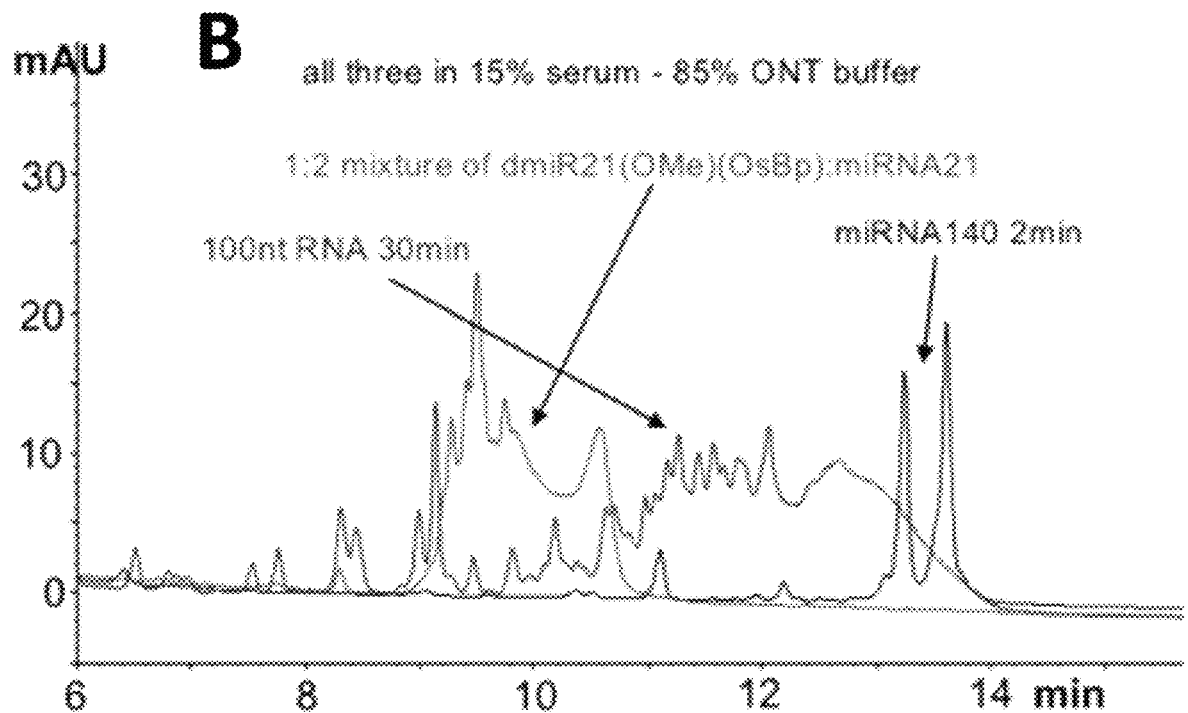

FIG. 26A,B. (FIG. 26A) Repeat of FIG. 6A in order to compare directly with HPLC profiles to the right. (FIG. 26B) HPLC profiles of three samples in 15% serum—85% ONT buffer, miRNA140 2 min incubation before analysis, 100 nt RNA 30 min incubation before analysis. The longer incubation is why the degradation of 100 nt RNA appears more severe compared to the degradation of miRNA140. Mixture of dmiR21(OMe)(OsBp): miRNA21=1:2 in about 5% water—95% ONT buffer (FIG. 26A) and the same mixture in 15% serum—85% ONT buffer (FIG. 26B). The HPLC profiles appear comparable suggesting that the hybrid suffers insignificant degradation in 15% serum—85% ONT buffer. HPLC method B used for these analyses (see Examples).

DETAILED DESCRIPTION

The terms defined immediately below are more fully defined by reference to the specification in its entirety. To the extent necessary to provide descriptive support, the subject matter and/or text of the appended claims is incorporated herein by reference in their entirety.

Definitions

It will be understood by all readers of this written description that the exemplary aspects and embodiments described and claimed herein can be suitably practiced in the absence of any recited feature, element or step that is, or is not, specifically disclosed herein.

The term "a" or "an" entity refers to one or more of that entity; for example, "a probe," is understood to represent one or more "probes." As such, the terms "a" (or "an"), "one or more," and "at least one" can be used interchangeably herein.

The term "and/or" where used herein is to be taken as specific disclosure of each of the specified features or components with or without the other. Thus, "and/or" as used in a phrase such as "A and/or B" herein is intended to include "A and B," "A or B," "A" (alone), and "B" (alone). Likewise, "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, technical and scientific terms used herein have the same meaning as commonly understood by one of ordinary skill in the art to which this disclosure is related. For example, unless otherwise specified, "complementary" base pairs refer to A/T, A/U, and G/C base pairing.

Numeric ranges are inclusive of the numbers defining the range. Even when not explicitly identified by "and any range in between," or the like, where a list of values is recited, i.e., 1, 2, 3, or 4, the disclosure specifically includes any range in between the values, i.e., 1 to 3, 1 to 4, 2 to 4, etc.

The headings provided herein are solely for ease of reference and are not limitations of the various aspects or aspects of the disclosure, which can be had by reference to the specification as a whole.

As used herein, the term "identity," i.e., "percent identity" to an amino acid sequence or to a nucleotide sequence disclosed herein refers to a relationship between two or more amino acid sequences or between two or more nucleotide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a nucleotide or amino acid sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using, i.e., the program "BLAST" which is available from the National Center for Biotechnology Information, and which program incorporates the programs BLASTN (for nucleotide sequence comparison) and BLASTP (for amino acid sequence comparison), which programs are based on the algorithm of Karlin and Altschul (Proc. Natl. Acad. Sci. USA 90(12):5873-5877, 1993).

As used herein, the term "complementary" when referring to nucleic acid molecules is given its standard definition for complementary Watson-Crick base pairing as understood in the art.

The term "nucleic acid" is a well-known term of art and is used herein to include DNA and RNA. Unless otherwise specified, a "nucleic acid" molecule and "polynucleotide" can be used interchangeably. A nucleic acid can comprise a conventional phosphodiester bond or a non-conventional bond (i.e., an amide bond, such as found in peptide nucleic acids (PNA)). By "isolated" nucleic acid it is intended a nucleic acid molecule that has been removed from its native environment, such as a sample of genomic DNA obtained from a subject. Isolated polynucleotides or nucleic acids further include such molecules produced synthetically.

As used herein, the terms "intact" or "native" when referring to an oligonucleotide means that the oligonucleotide is not osmylated.

As used herein, a "biological sample" is one derived from a subject such as a human, animal, plant, bacteria, virus, fungus, or other type of multi-cellular or single-cellular life form. In certain aspects, the biological sample can be obtained directly from the subject, such as by drawing blood, collecting a urine sample, or a tissue or liquid biopsy. In certain aspects, the biological sample can be obtained indirectly, such as from biological evidence collected at a crime scene. In certain aspects, the biological sample is a bodily fluid such as blood, plasma, lymph, saliva, urine, amniotic fluid, spinal fluid, etc. In certain aspects, a biological sample is a fluid sample with components derived from a tissue or cells suspended, dissolved, in solution, reconstituted in, or the like, in the fluid sample. A "complex mixture" means a sample that comprises various components such as nucleic acids, proteins, carbohydrates, etc. and/or varied nucleic acid molecules.

As used herein, an "event" or "count" is detected by applying a voltage across the two compartments of a nanopore device, leading to a constant flow of electrolyte ions (Io) via the pore, which is recorded as a function of time (i-t). The passage of a single molecule through the pore reduces Io to a lower level of residual ion current (Ir). This is recorded as an "event" with (Ir) and residence time (τ) (FIG. 1B).

It has been discovered that a portable nanopore device from Oxford Nanopore Technologies (ONT) can be repurposed to detect a DNA/RNA polynucleotide (target) in a complex mixture by conducting voltage-driven ion-channel measurements. The detection and quantitation of the target was enabled by the use of a unique complementary probe of the present disclosure. Using a validated labeling technology, probes are tagged with a bulky Osmium tag (Osmium tetroxide 2,2'-bipyridine), in a way that preserves strong hybridization between probe and target. Untagged oligos traverse the nanopore relatively quickly compared to the device's acquisition rate and exhibit count of events comparable to the baseline. Counts can be reported, for example, by a publicly available software, OsBp_detect (Kanavarioti, A., & Kang, A. See RNA(OsBp) event detection Python package in a public repository: hypertext transfer protocol secure github.com/kangaroo96/osbp_detect and for step-by-step installation instructions see here: hypertext transfer protocol secure github.com % kangaroo96/osbp_detect/blob/master % instructions.md). Due to the presence of the bulky Osmium tag, osmium-tagged probes traverse more slowly, producing multiple counts over the baseline, and can even be detected in the single digit attomole (amole) range. In the presence of the target, however, the probe is "silenced". Silencing is attributed to a double-stranded complex that for practical purposes of this disclosure are considered not to traverse the nanopore under the applied conditions. Thus, the disclosed ready-to-use platform can be tailored as a diagnostic test to meet the requirements, for example, of point-of-care circulating tumor DNA (ctDNA), cell free DNA (cfDNA) fragmented RNA, and microRNA (miRNA) detection and quantitation in body fluids.

Figure 1C:
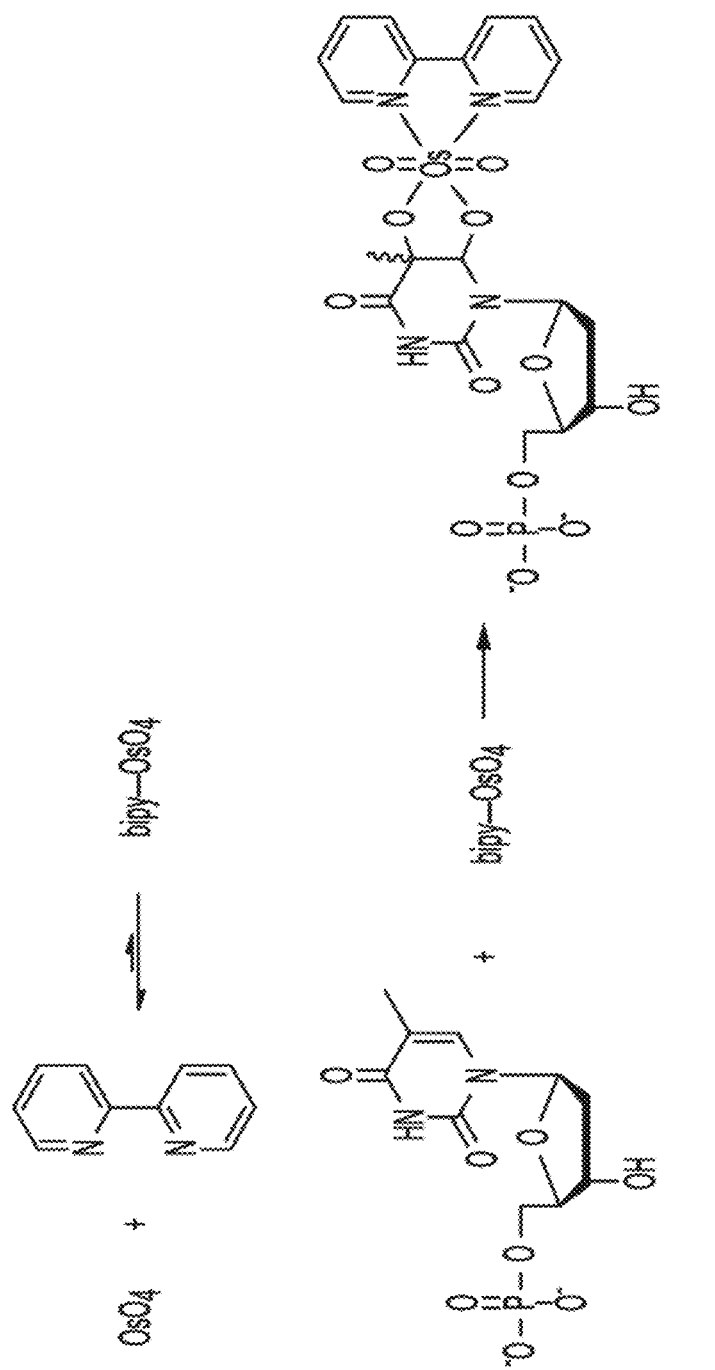

Aspects of the present disclosure exploit selective labeling (also referred to herein as tagging) of nucleic acids in an effort to enhance base-to-base discrimination (Ding, Y. & Kanavarioti, A. (2016); Sultan M., Kanavarioti, A. (2019); Kanavarioti, A. (2015)), utilizing Osmium tetroxide 2,2'-bipyridine (OsBp) as the label/tag. OsBp is not reactive towards purines and does not cleave the phosphodiester bond in DNA or RNA. OsBp adds to the C5-C6 double bond of the pyrimidines and forms two strong C—O bonds without cleaving the pyrimidine ring (FIG. 1C) (Chang, C. H., Beer, M. & Marzilli, L. G. (1977); Palecek E. (1992); Reske T., Surkus, A-E., Duwensee, H. & Flechsig G.-U. (2009); Kanavarioti, A. et al. (2012); Kanavarioti, A. (2016): Debnath, T. K. & Okamoto, A. (2018)). Reactivity of OsBp towards thymidine (T) is 28- and 7.5-times higher compared to the reactivity towards deoxycytidine (dC) and deoxyuridine (dU), respectively (Ding, Y. & Kanavarioti, A. (2016)). Labeling condition protocols have been developed to selectively label T in the presence of the other pyrimidines (Kanavarioti, A. et al. (2012)). Further, the inventor developed capillary electrophoresis (CE) and High-performance Liquid chromatography (HPLC) methods to measure the extent of labeling in short and long DNA and RNA (Kanavarioti, A. et al. (2012); Kanavarioti, A. (2016); see Examples). Voltage-driven ion-channel measurements were conducted using SiN solid-state nanopores (Henley, R. Y., Vazquez-Pagan, A. G., Johnson, M., Kanavarioti, A. & Wanunu, M. (2015)), the α-Hemolysin nanopore (Ding, Y. & Kanavarioti, A. (2016)), as well as the CsGg nanopore in the MinION (Sultan M., Kanavarioti, A. (2019)), and demonstrated that all three platforms allow the translocation of osmylated nucleic acids, and clearly discriminate them from native nucleic acids. The discrimination is manifested as an event with markedly lower Ir and longer z and can be increased, for example, by increasing the number and/or position of OsBp moieties labeling an oligonucleotide. These features were utilized in order to single-out, detect, and count OsBp-tagged oligos in a complex mixture of native DNA and RNA.

Figure 1D:
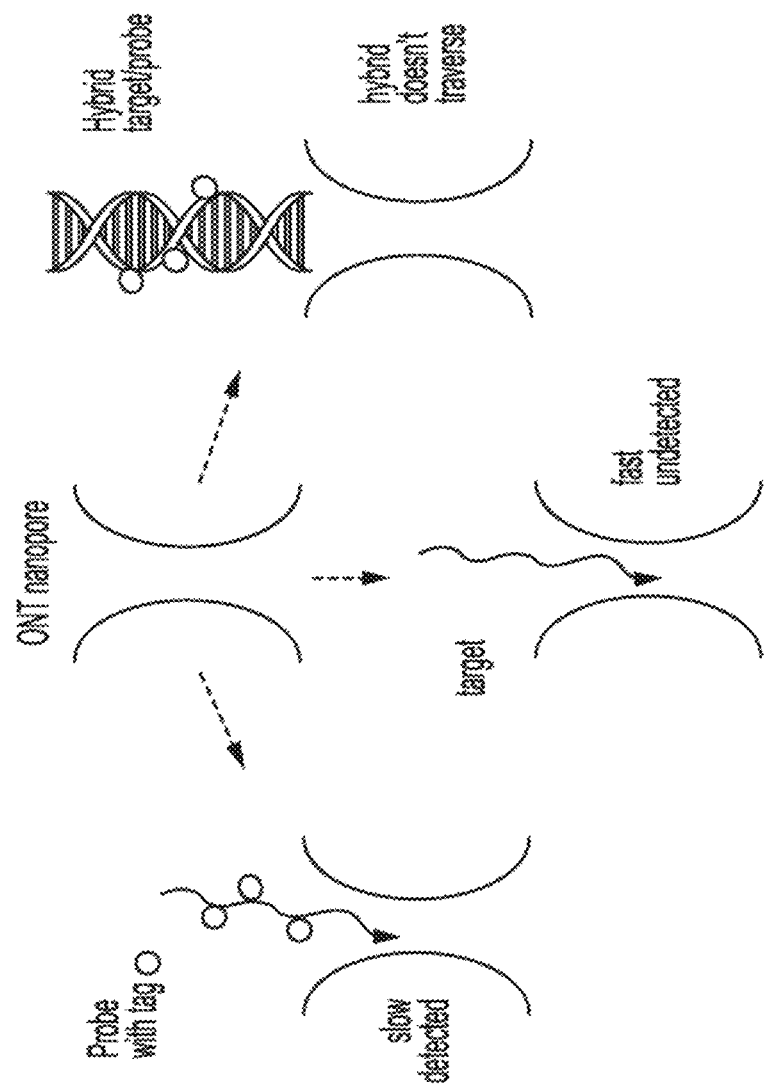

FIG. 1D illustrates the concept behind nanopore-based identification and quantification of a target oligo in a complex mixture. Certain aspects of this disclosure are enabled by a custom-designed OsBp-tagged oligo (probe) as described in detail elsewhere herein, that is at least partially complementary to a nucleic acid target molecule sufficient to create a hybridized double-stranded complex. The use of a complementary oligo as a probe has been validated in several experimental nanopore platforms (Wanunu M, Dadosh T, Ray V, Jin J, McReynolds L, Drndić M. (2010); Xi, D. et al. (2016); Zahid, O. K., Wang, F., Ruzicka, J. A., Taylor, E. W. & Hall, A. R. (2016): Tian, K., Shi, R., Gu, A., Pennella, M., & Gu, L. Q. (2017); Hao, W., Haoran T., Cheng Y., & Yongxin, L. (2019)). These platforms however are complicated by the fact that the probe is conjugated to a protein (Wanunu M, Dadosh T, Ray V, Jin J, McReynolds L, Drndić M. (2010)), a nanoparticle (Hao, W., Haoran T., Cheng Y., & Yongxin, L. (2019)), a homopolymer (Xi, D. et al. (2016)), or a polypeptide (Tian, K., Shi, R., Gu, A., Pennella, M., & Gu, L. Q. (2017)). The detection in these platforms relies on counting the long blockades produced by the double-stranded hybrid complex bumping at the nanopore entry and practically "getting stuck". None of these methods reached commercial availability which hinders their broader use. In contrast to earlier approaches based on detection of the hybrid (Wanunu M, Dadosh T, Ray V, Jin J, McReynolds L, Drndić M. (2010); Xi, D. et al. (2016); Zahid, O. K., Wang, F., Ruzicka, J. A., Taylor, E. W. & Hall, A. R. (2016); Tian, K., Shi, R., Gu, A., Pennella, M., & Gu, L. Q. (2017); Hao, W., Haoran T., Cheng Y., & Yongxin, L. (2019)), aspects of the present disclosure detect the translocation of an osmylated probe facilitated by a relatively slow acquisition rate (for example, but not limited by, MinION (3.012 kHz sampling rate, equivalent to reporting 3 data points per 1 ms)) (Oxford Nanopore Technologies website: nanoporetech.com, under Resources/Publications). While the slow sampling rate misses many, most, or all translocation events of native DNA/RNA oligonucleotides, the events corresponding to the translocation of the OsBp-tagged probes are detected. In the absence of the nucleic acid target molecule (e.g., complementary probe binding partner), the osmylated probe traverses the nanopore and produces a detectable event. In the presence of the nucleic acid target molecule, the probe forms a hybridized complex with the target (e.g., a 1:1 double-stranded hybrid). The hybridized molecule does not fit through and does not traverse the nanopore (FIG. 1D). Hence the hybridized OsBp-tagged probe is "silenced". In certain aspects, the hybridized complex, however, does not "clog" and prevent unhybridized single-stranded nucleic acids from going through the pore. This can be achieved, for example, by incorporating automatic reversal of voltage to free the nanopores from such unproductive, "clogging" occurrences. Therefore, to detect, test for, and/or determine the presence or absence of a nucleic acid target molecule in a sample, an osmylated-probe is added to a particular sample which can be run on a nanopore platform or device by conducting voltage-driven experiments. Absence of the nucleic acid target molecule in a sample can be, in certain aspects, construed from the detection of numerous events due to the tagged probe's translocation via the nanopore. The presence of the nucleic acid target molecule in a sample can be, in certain aspects, construed from the absence of events, due to hybrid formation between the tagged probe and the target. Quantification of the target can be based on the known concentration of the tagged probe and 1:1 hybrid formation.

The presence of T(OsBp) moieties in the middle of a sequence is not a feature shared by many potential ctDNA, miRNA, or other such targets. Therefore, in certain aspects of probes of this disclosure, one, some, or all Ts in the sequence are replaced with uridine (U), deoxyuridine (dU), or 2'-OMe-Uridine (mU). Further, in certain aspects, one, some, or all the bases are modified as 2'-OMe. In certain aspects, one or more adjacent T(OsBp) are added at the 3'-end or the 5'-end of the probe oligo. And, in some aspects, one or more additional dAs are added at the 3'-end or the 5-end of the probe oligo. Replacing Ts with U, dU, or mU reduces or eliminates the presence of OsBp within the complementary sequence which could hinder hybridization to the nucleic acid target molecule.

RNA/DNA hybrids are known to be more stable compared to DNA/DNA hybrids. Thus for example, in certain aspects, an RNA-based probe can target a DNA after addition of the probe to a biological sample to be tested. In certain aspects, the DNA (e.g., a dsDNA) is relatively short, e.g., less than 100, 90, 80, 70, 60, 50, 40, 30, 28, 25, 24, 23, 22, 21, 20, 19, or 18 nucleotides long. In certain aspects, the method includes a denaturation step before the RNA-based probe hybridizes to the nucleic acid target molecule, for example to denature a dsDNA target molecule and/or remove any secondary structure of the probe. RNA probes exhibit a different nanopore profile compared to DNA-based probes, as indicated by comparison of the (Ir/Io)max in FIG. 2A with the corresponding (Ir/Io)max in all the other figures representing probes. This feature can lead to probe multiplexing in order to test more than one target at a time. Similarly, probes like dmiR21(OMe) that are missing the 3 adjacent Ts were seen to translocate at −180 mV, while probes with 3 adjacent Ts require −220 mV. Such distinctions, e.g., differences in translocation between probes as a result of voltage, current, time, etc., and based on the quantity and/or location of osmylation of the probe, can be exploited in order to multiplex probes. Distinct nanopore profiles will reveal which one of the probes is silenced. With just one probe, the test can conclusively identify the presence/absence of the target by comparing the total count of events of the probe alone to the total count of events to the mixture of the probe with the unknown sample. With a multiplexed test, for example, counts can be plotted as histograms, in order to determine which probe is missing. Thus, certain aspects of this disclosure provide for multiplexing in order to test for more than one nucleic acid target molecule at a time, even within the same test sample.

Certain aspects of this disclosure provide for ion-channel single molecule experiments conducted using, for example, portable, commercially available nanopore devices. Tested targets were DNA and RNA oligos and in certain aspects, exhibited a 9 orders of magnitude range of detection. This sensitivity approaches single-digit attomole target sensitivity, for example from an 11 µL biological sample. These properties enable detection and quantification of highly dilute samples such as ctDNA and miRNAs found in bodily fluids.

Provided for herein is a method for detecting the presence of a nucleic acid target molecule in a biological sample. One of ordinary skill in the art will recognize that for any of the methods described below, an analogous method can also be used to detect/verify the absence of a nucleic acid target molecule in a biological sample if the criteria for detecting the nucleic acid target sample are not met. In certain aspects, the method comprises contacting a test sample that comprises (i) a biological sample comprising a nucleic acid target molecule and (ii) an osmylated single-stranded oligonucleotide probe comprising at least one pyrimidine residue covalently bonded to a substituted or unsubstituted Osmium tetroxide (OsO4)-2,2'-bypyridine group (OsBp group). In certain aspects, the substitution occurs on the 2,2'-bypyridine of the OsBp. In certain aspects, the test sample comprises a sample buffer in which the biological sample is diluted. The sample buffer composition can vary depending on the type of nanopore device/system, type of biological sample, etc., and can be determined for each circumstance. The biological sample is generally diluted so that at least about 50%, 60%, 70%, 75%, 80%, 85%, 90%, or 95% of the volume of the test sample is sample buffer with the remainder of the volume being the biological sample and/or the solution comprising the probe. One of ordinary skill in the art will recognize, however, that the smaller the volume of biological sample used, the smaller the amount of the nucleic acid target molecule that might be present, thus requiring higher sensitivity. The osmylated pyrimidine can be a thymidine (T), cytidine (C), deoxycytidine (dC), deoxyuridine (dU), uridine (U) or a derivative thereof. In certain aspects, at least one osmylated pyrimidine residue is a thymidine residue (T). In certain aspects, the sequence of the probe is at least partially complementary to the sequence of the nucleic acid target molecule, sufficient to allow the formation of a hybridized probe/target complex. In certain aspects, at least a portion of the sequence of the probe is fully complementary to at least a segment of the sequence of the nucleic acid target molecule. A nanopore device is used to detect in the test sample the number of events wherein unhybridized osmylated-probe traverses the nanopore. The number of events detected in the test sample can then be compared against some other value to determine or indirectly detect the presence, or in some aspect the absence, of the nucleic acid target molecule in the test sample. In certain aspects, wherein the only potential source of the nucleic acid target molecule in the test sample is that attributed to the biological sample, detection of the nucleic acid target molecule in test sample detects the nucleic acid target molecule in the biological sample. Unlike prior methods of detecting oligonucleotides on a nanopore system, the nanopore device/system of this disclosure does not require that the probe is conjugated to a protein, a nanoparticle, a homopolymer, or a polypeptide for detection of the probe. Thus, in certain aspects, the probe is not conjugated to a protein, a nanoparticle, a homopolymer, or a polypeptide. Further, unlike prior nanopore detection methods, detection is not achieved by counting long blockades produced by the hybridized probe/target complex blocking the nanopore or by melting of a hybridized probe/target complex in the nanopore.

(i) In certain aspect, the number of events detected in the test sample can be compared to a "number of corresponding probe sample events." The number of corresponding probe sample events are those that are detected in a probe sample or theoretically should be detected for a probe sample, wherein unhybridized osmylated-probe traverses the nanopore in the absence of the nucleic acid target. As explained in more detail and shown in representative Examples elsewhere herein, the presence of the nucleic acid target molecule in the target sample (such as coming from the biological sample or added as a control) leads to hybridization with the complementary osmylated-probe, thus "silencing" the probe (preventing it from traversing the nanopore and resulting in a detectable event). Thus, a reduction in the number of events detected in the test sample relative to the number of probe sample events is indicative of the formation of the hybridized probe/target complex and thus the presence of the nucleic acid target molecule in the test sample. Because unhybridized probe will traverse the nanopore and lead to detectable events, even in the presence of the nucleic acid target molecule if not all of the probe is hybridized, in certain aspects, the amount of probe should not greatly exceed or should not exceed the amount of nucleic acid target in the test sample. In certain aspects, the amount of probe should be about equal to or less than the amount of nucleic acid target in the test sample. In certain aspects, the strength of the hybridization between the target nucleic acid molecule and its complementary probe can also be taken into account. One of ordinary skill in the art can determine based on available information and routine experimentation an approximate amount of nucleic acid target molecule in a particular type of sample and can further refine the amount of probe to use for optimal results. In certain aspects the reduction in the number of events is by at least a factor of two, by at least a factor of three, or by at least a factor of four to confidently deduce that the observed reduction is due to the presence of the nucleic acid target molecule in the test sample and the formation of a probe/target hybrid. This confidence level can vary, for example, from probe/target to probe/target, test conditions to test conditions, and nanopore device to nanopore device and can be determined by routine experimentation of a given system. Thus, in certain aspects, a reduction in the number of events between those detected in a test sample and a number of corresponding probe sample events is a reduction of at least a factor of two, at least a factor of three, or at least a factor of four In certain aspects, the number of corresponding probe sample events is the number of events contemporaneously detected in one or more probe samples at the time of detection of the number of events in the test sample. Contemporaneously detected means in the same general period of time so that one of ordinary skill in the art would consider the detection of events in the test sample and the detection of events in the probe sample to be run as part of the same test or experiment, but not necessarily occur in parallel. In certain aspects, contemporaneous detection of events in the test sample and in the probe sample would use common reagents, such as from the same lot, to reduce variability. In certain aspects, the reagents used for the contemporaneous detection are provided together in a kit.

In certain aspects, the number of corresponding probe sample events is a predetermined value for a given amount of probe. A predetermined value of the number of probe sample events for a given amount of probe can be determined empirically by running tests on probe samples with a known amount of probe and detecting the number of events produced, for example, on certain types of nanopore devices and under certain conditions, e.g., current, voltage, time, buffer conditions, age and/or amount of use of a nanopore device, etc. This predetermined value can then be used for comparison purposes against the number of events detected in various test samples under similar conditions. This predetermined value can be used for comparison to test samples with the same or a similar amount of probe or the value can be extrapolated for different amounts of probe. A predetermined value of the number of corresponding probe sample events for a given amount of probe can also be determined theoretically. A theoretical determination can be, but not need be, informed by experimental observations.

In certain aspects, the number of osmylated probe sample events are detected by a nanopore device in a probe sample and then the osmylated probe in the probe sample is combined with a biological sample to create a test sample. The number of events in this test sample can then be detected by the nanopore device for comparison against the number of osmylated probe sample events that were detected.

(ii) In certain aspects, the number of events detected in the test sample can be compared to the "noise" of a corresponding baseline sample that does not contain any osmylated-probe. One of ordinary skill in the art would understand that even in the absence of osmylated-probe, and even for just the sample buffer itself in the absence of any biological sample, the nanopore system will indicate a certain number of events referred to herein as "noise." One of ordinary skill in the art would also understand that this noise can be accounted for in various ways (e.g., such as calibrating an instrument to zero out the noise) which are non-limiting on the present methods. As explained in more detail and shown in representative Examples elsewhere herein, the presence of the nucleic acid target molecule in the target or control sample (such as coming from the biological sample or added as a control) leads to hybridization with the complementary osmylated-probe, thus "silencing" the probe (preventing it from traversing the nanopore and resulting in a detectable event). Thus, an absence of an increase in the number of events detected in the test sample relative to the noise of the corresponding baseline sample is indicative of the formation of the hybridized probe/target complex and thus the presence of the nucleic acid molecule in the test sample. Because unhybridized probe will traverse the nanopore and lead to detectable events, even in the presence of the nucleic acid target molecule if not all of the probe is hybridized, in certain aspects, the amount of probe should not greatly exceed or should not exceed the amount of nucleic acid target in the test sample. In certain aspects, the amount of probe should be about equal to or less than the amount of nucleic acid target in the test sample. In certain aspects, the strength of the hybridization between the target nucleic acid molecule and its complementary probe can be taken into account. One of ordinary skill in the art can determine based on available information and routine experimentation an approximate amount of nucleic acid target molecule in a particular type of sample and can further refine the amount of probe to use for optimal results. In certain aspects, an absence of an increase in the number of events in the test sample relative to the number of events in the baseline sample means an increase of less than a factor of two, less than a factor of three, or less than a factor of four to confidently deduce that the observed reduction is due to the presence of the nucleic acid target molecule in the test sample and the formation of a probe/target hybrid. This confidence level can vary, for example, from probe/target to probe/target, test conditions to test conditions, and nanopore device to nanopore device and can be determined by routine experimentation of a given system. Thus, in certain aspects, an absence of an increase in the number of events in the test sample relative to the number of events in the baseline sample means an increase of less than a factor of two, less than a factor of three, or less than a factor of four.

In certain aspects, the noise of a corresponding baseline sample is contemporaneously determined in one or more baseline samples at the time of detection of the number of events in the test sample. Contemporaneously detected means in the same general period of time so that one of ordinary skill in the art would consider the detection of events in the test sample and the determination of noise in the baseline sample to occur as part of the same test or experiment, but not necessarily occur in parallel. In certain aspects, contemporaneous detection of events in the test sample and the determination of noise in the baseline sample would use common reagents, such as from the same lot, to reduce variability. In certain aspects, the reagents used for the contemporaneous detection are provided together in a kit.

In certain aspects, the noise of a corresponding baseline sample is a predetermined value. For example, in certain aspects, it may be predetermined for a certain composition of a sample (e.g., type of sample buffer, type of biological sample, concentration of biological sample in the test sample, etc.). A predetermined value of the noise in a baseline sample can be determined empirically by running tests on samples with known compositions and determining the amount of noise, for example, on certain types of nanopore devices and under certain conditions, e.g., current, voltage, time, buffer conditions, age of nanopore device, etc. This predetermined value can then be used for comparison purposes against the number of events detected in various test samples under similar conditions. This predetermined value can be used for comparison to test samples with the same or a similar composition or the value can be extrapolated for differing compositions, e.g., a higher or lower concentration of biological sample. A predetermined value of the noise of a corresponding baseline sample of a certain composition can also be determined theoretically. A theoretical determination can be, but not need be, informed by experimental observations.

In certain aspects, the noise of a corresponding baseline sample is determined for a nanopore device/system and then the osmylated probe is added to the baseline sample, such as one comprising a biological sample, to create a test sample. The number of events in this test sample can then be detected by the nanopore device for comparison against the amount of noise of the baseline sample.

(iii) In certain situations, it may be useful to use as a control a sample comprising the nucleic acid target molecule and the complementary osmylated probe, especially, for example, wherein the amount of nucleic acid target molecule in the control sample is known. Thus, in certain aspects, the number of events detected in the test sample can be compared to the number of corresponding control sample events wherein unhybridized osmylated-probe traverses the nanopore in the presence of a known amount of the nucleic acid target molecule and/or known amount of the osmylated probe. Consistent with the use of a probe sample and test sample described above, a reduction in the number of events detected in the test sample relative to the number of corresponding control sample events is indicative of the formation of the hybridized probe/target complex and the presence of a higher amount of the nucleic acid target molecule in the test sample over the control sample. Use of such a control sample can be used to explore the hybridization between a nucleic acid target molecule and its complementary probe and also to titrate and/or determine the optimum amount of probe to use for a given amount of nucleic acid target molecule, even in the absence of the biological sample. Such a use can be used to develop quantitative methods of detecting the amount of nucleic acid target molecule in a biological sample.

As noted above, the 2,2'-bipyridine in OsBp, which is attached to a pyrimidine in the oligonucleotide probe, can be substituted or unsubstituted. In certain aspects, it is substituted, for example, substituted with one or more methyl or ethyl groups.

In certain aspects, the nucleic acid target molecule can be a biomarker and/or indicative of health, age, or a genotype associated with a phenotype or of a particular disease or disease state. In certain aspects, the nucleic acid target is a circulating tumor DNA (ctDNA), cell-free DNA (cfDNA), miRNA, a fragmented coding RNA, or a non-coding RNA. In certain aspects, the non-coding RNA is less than about 300 bases long. In certain aspects, the nucleic acid target molecule is a single-stranded nucleic acid molecule. In certain aspects, the nucleic acid target molecule is found in the biological sample as a single-stranded nucleic acid molecule. In certain aspects, as found in the biological sample, the nucleic acid target molecule is a strand of a double-stranded nucleic acid molecule. Thus, in certain aspects, the method comprises denaturing double-stranded nucleic acids and/or nucleic acids with secondary structure in the test sample, including the probe, to form single-stranded nucleic acid strands so that a single-stranded oligonucleotide probe can hybridize to a single-stranded target molecule.

As explained in detail elsewhere herein, in certain aspects, the nanopore device allows the voltage-driven translocation of osmylated and non-osmylated single-stranded nucleic acids but prevents the translocation of double-stranded nucleic acids. While the methods disclosed herein can be performed using commercially available nanopore devices, they are not limited to the type of nanopore device. In certain aspects, the nanopore device utilizes a nanopore having a minimal pore diameter of about 1.3 nM to about 7.1 nM. In certain aspects, the nanopore device utilizes a Phi29, alpha-hemolysin, Aerolysin, MspA, CsGg, PA63, ClyA, FhuA, or SPP1 protein nanopore, or a bioengineered derivative thereof.

As explained elsewhere herein, the voltage will vary depending on factors such as the nanopore itself, the design of the osmylated probe, sample composition, age and/or amount of usage of the nanopore device, etc. Further, different voltages can be applied to specifically drive certain nucleic acids through the nanopore but not others, such as to drive non-osmylated single-stranded nucleic acids across the pore before applying the voltage needed to detect the osmylated probe or to differentiate between osmylated probes of different designs such as in a multiplex test. In certain aspects, a voltage of about at least or at least about −180 mV, −190 mV, −200 mV, −210 mV, −220 mV, −230 mV, −240 mV, or −250 mV is applied to determine the presence of the target. In certain aspects, a voltage of between any or any of about −180 mV, −190 mV, −200 mV, −210 mV, −220 mV, −230 mV, or −240 mV and any or any of about −190 mV, −200 mV, −210 mV, −220 mV, −230 mV, or −240 mV, or −250 mV is applied to determine the presence of the target. In certain aspects, a voltage of less than or less than about −200 mV, −190 mV, −180 mV, −170 mV, −160 mV, or −150 mV is applied before the voltage applied to determine the presence of the target. In certain aspects, a voltage of between any or between any of about −200 mV, −190 mV, −180 mV, −170 mV, or −160 mV and any or any of about 190 mV, −180 mV, −170 mV, or −160 mV, −150 mV is applied before the voltage applied to determine the presence of the target. It will be recognized by one of ordinary skill in the art that depending on the particular nanopore device and the characteristics of the incorporated nanopores, this voltage could be positive instead of negative, and it could be much higher in absolute terms.

Also, as explained in detail elsewhere herein, in certain aspects, the method comprises using an algorithm to count events produced by the passage of the probe, as reported by the time recording, to determine if the probe translocated freely via the nanopore. In certain aspects, the nanopore device allows for the distinction between different osmylated probes and multiplex detection of multiple different nucleic acid targets in a test sample.

Using the methods and probes disclosed herein, in certain aspects, the method can detect an amount of less than or less than about 1 pM, 100 fM, 10 fM, 1 fM, 100 aM, 10 aM, 1 aM, or 0.1 aM of the nucleic acid target in the test sample. In certain aspects, the method can detect an amount of at least or at least about 0.1 aM, 1 aM, 10 aM, 100 aM, 1 fM, 10 fM, 100 fM, or 1 pM of the nucleic acid target in the test sample. And, in certain aspects, the method can detect an amount of between any or any of about 0.1 aM, 1 aM, 10 aM, 100 aM, 1 fM, 10 fM, or 100 fM and any or any of about 1 aM, 10 aM, 100 aM, 1 fM, 10 fM, 100 fM, of 1 pM of the nucleic acid target in the test sample.

In certain aspects, the method is quantitative for the amount of the nucleic acid target molecule in the test sample and/or biological sample.

Certain aspects of this disclosure are drawn to the design of probes for use in detecting a nucleic acid target molecule in any of the methods described herein.

In certain aspects, the probe is DNA. In certain aspects, the DNA backbone is modified. For example, in certain aspects, at least one of the sugars in the nucleic acid backbone are 2'-OMe-deoxyribose. For example 1, 2, 3, 4, 5 or more or 5%, 10%, 25%, 500%, 75%, 90%, 95% or more or 100% of the sugars in the nucleic acid backbone are 2'-OMe-deoxyribose.

In certain aspects, the probe is RNA. In certain aspects, the RNA backbone is modified. For example, in certain aspects, at least one of the sugars in the nucleic acid backbone are 2'-OMe-ribose. For example 1, 2, 3, 4, 5 or more or 5%, 10%, 25%, 50%, 75%, 90%, 95% or more or 100% of the sugars in the nucleic acid backbone are 2'-OMe-ribose.

The length of the osmylated probe can be tailored to the length of the nucleic acid target molecule as well as for considerations such as case and cost of synthesis, the amount of osmylation that would occur, and hybridization (e.g., a longer probe can have greater specificity and more complementary base-pairing to a target than, e.g., a very short probe). In certain aspects, the osmylated probe has a length of about any of 9, 10, 11, 12, 13, 14, 15, 16, 17, 18, 19, 20, 21, 22, 23, 24, 30, 35, 40, 50, 60, or 75 to any of about 10, 11, 12, 13, 14, 15, 16, 17, 18, 19, 20, 21, 22, 23, 24, 30, 35, 40, 50, 60, 75, or 100. In certain aspects, the osmylated probe has a length of about 12 to 50 nucleotides. Because detection of the target nucleic acid molecule is achieved by forming a hybrid probe/target complex with the osmylated probe and because translocation of the probe through the nanopore is in its single-stranded form, in certain aspects it is preferable that the probe not self-hybridize to itself, especially in the region of complementarity with the target. Thus, in certain aspects, the portion of the probe that is at least partially complementary to the sequence of the nucleic acid target molecule lacks contiguous self-complementary sequences of more than 2 nucleotides. In certain aspects, the portion of the probe that is at least partially complementary to the sequence of the nucleic acid target molecule is unstructured. And in certain aspects, the portion of the probe that is at least partially complementary to the sequence of the nucleic acid target molecule does not self-hybridize.

In certain aspects, an osmylated single-stranded oligonucleotide probe molecule comprises at least one pyrimidine residue covalently bonded to a substituted or unsubstituted Osmium tetroxide (OsO4)-2,2'-bypyridine group (OsBp group). In certain aspects, at least one osmylated pyrimidine residue is a thymidine residue (T). It has been discovered that the amount of osmylation (the number of osmylated pyrimidines) influences how the probe transverses the nanopore and thus how it can be detected as an event and how it can be distinguished from a non-osmylated single-stranded nucleic acid traversing the nanopore. In certain embodiments, the osmylated probe comprises at least two, three, four, five, or six osmylated pyrimidine residues. In certain embodiments, the osmylated probe comprises two, three, four, five, or six osmylated pyrimidine residues. As described elsewhere herein, certain methods preferably osmylate thymidine residues (T) over other pyrimidines, thus allowing an even more nuanced approach to osmylating the oligonucleotide probe. In certain aspects, the osmylated probe comprises at least two, three, four, five, or six osmylated thymidine residues (T). In certain aspects, the osmylated probe comprises two, three, four, five, or six osmylated thymidine residues (T). In addition to the amount/number of osmylated residues on the probe, the position of the osmylated residues in relation to each other can also influence how the probe traverses the nanopore. The OsBp group on one residue can hinder the degrees of freedom of movement of an OsBp group on an adjacent residue, and thus how easily the probe can traverse the nanopore with the OsBp groups attached. Three adjacent residues further restrict movement of the middle residue. Thus, in certain aspects, the osmylated probe comprises at least two, three, or four adjacent osmylated pyrimidine residues. In certain aspects, the osmylated probe comprises two, three, or four adjacent osmylated pyrimidine residues. In certain aspects, the osmylated probe comprises at least two, three, or four adjacent osmylated thymidine residues (T). In certain aspects, the osmylated probe comprises two, three, or four adjacent osmylated thymidine residues (T). Further, the addition of deoxyadenosine (dA) or adenosine (A) residues to the end of the oligonucleotide probe may aid in traversal of the nanopore. In certain aspects, the osmylated probe comprises or comprise at least one, two, three, four, five, or six adenosine residues (dA or A) at the 5'-end or 3'-end of the probe. In certain aspects, the osmylated probe comprises or comprises at least one, two, three, four, five, or six adenosine residues (dA or A) at the 3'-end of the probe. In certain aspects, the osmylated probe comprises or comprises at least one, two, three, four, five, or six adenosine residues (dA or A) at the 5'-end of the probe. In certain aspects, one or more of said 5'-end or 3'-end adenosine residues (dA or A) do not hybridize to the nucleic acid target molecule.

Osmylation of residues, especially within the portion of the probe that is complementary or at least partially complementary to the nucleic acid target molecule can hinder hybridization with the nucleic acid target molecule. To avoid this and/or enhance hybridization, it may be useful to locate osmylated pyrimidines, such as osmylated thymidine residues, in noncomplementary regions of the oligonucleotide probe sequence, such as at the 5'-end or 3'-end and/or replacing thymidine residues in the regions of the probe complementary to the nucleic acid target with other pyrimidines and taking advantage of the fact that under certain reaction conditions, thymidine residues can be preferentially osmylated over other pyrimidines.

In certain aspects, the osmylated probe does not comprise two or more adjacent osmylated pyrimidine residues that are not located at the 5'-end or 3'-end of the probe. And, in certain aspects, the osmylated probe does not comprise two or more adjacent osmylated thymidine residues (T) that are not located at the 5'-end or 3'-end of the probe. In certain aspects, an osmylated probe comprises at least two, three, or four adjacent osmylated pyrimidine residues located at the 5'- or 3'-end of the probe. In certain aspects, an osmylated probe comprises two, three, or four adjacent osmylated pyrimidine residues located at the 5'- or 3'-end of the probe. In certain aspects, the osmylated probe comprises at least two, three, or four adjacent osmylated thymidine residues (T) located at the 5'-end or 3'-end of the probe. In certain aspects, the osmylated probe comprises two, three, or four adjacent osmylated thymidine residues (T) located at the 5'-end or 3'-end of the probe. In certain aspects, one or more of said 5'-end or 3'-end adjacent pyrimidine residues does not hybridize to the nucleic acid target molecule. In certain aspects, none of said 5'-end or 3'-end adjacent pyrimidine residues hybridizes to the nucleic acid target molecule. In certain of the forgoing aspects, the adjacent osmylated pyrimidine/thymidine residues are located at the 5'-end of the probe. In certain of the forgoing aspects, the adjacent osmylated pyrimidine/thymidine residues are located at the 3'-end of the probe.

As disclosed herein, in certain aspects thymidine residues (T) can be preferentially osmylated over other pyrimidines. Thus, in certain aspects, at least about 95%, 96%, 97%, 98%, 99%, or 100% of the thymidine residues (T) in the oligonucleotide probe molecule are osmylated and in certain aspects at least about 80%, 85%, 90%, 95%, 96%, 97%, 98%, 99%, or 100% of pyrimidines present in the probe, other than thymidine (T), are not osmylated. The DNA residue thymidine (T) and the RNA residue uridine (U) both are complementary to adenosine (A). In certain aspects, the probe is DNA but at least one thymidine residue (T) in the probe sequence, other than adjacent thymidine residues (T) located at the 5'-end or 3'-end, is replaced by a uridine (U) or a deoxyuridine (dU) or a 2'-OMe-uridine (mU) residue. In certain aspects, at least about 80%, 85%, 90%, 95%, 96%, 97%, 98%, 99%, or 100% of the thymidine (T) residues in the probe sequence, other than adjacent thymidine residues (T) located at the 5'-end or 3'-end, are replaced by uridine residues (U, dU, or mU). The result is an oligonucleotide probe that through the substitution of uridine (U) for thymidine (T), contains fewer or does not contain any osmylated thymidine residues (T) in the region of the probe that hybridizes to the complementary nucleic acid target molecule but does contain adjacent osmylated thymidines at the 3'-end or 5'-end of the probe.

There are numerous combinations of features that can be incorporated into the design of an osmylated oligonucleotide probe for use in the methods of this disclosure. In one representative design, the osmylated probe comprises or comprises at least two, three, or four adjacent osmylated thymidine residues (f) located at the 5'-end of the probe, the probe is DNA but the thymidine residues (T) in the probe sequence, other than the adjacent thymidine residues (T) located at the 5'-end, are replaced by a uridine residue (U, dU, or mU); and at least about 80%, 85%, 90%, 95%, 96%, 97%, 98%, 99%, or 100% of pyrimidines present in the probe, other than thymidine (T), are not osmylated. Further, in certain aspects, at least one of the sugars in the nucleic acid backbone are 2'-OMe-deoxyribose. In another representative design, the osmylated probe comprises three adjacent osmylated thymidine residues (T) located at the 5'-end of the probe, the probe is DNA but the thymidine residues (T) in the probe sequence, other than the three adjacent thymidine residues (T) located at the 5'-end, are replaced by a uridine residue (U, dU, or mU); and all of the pyrimidines present in the probe, other than thymidine (T), are not osmylated. Further, in certain aspects, some or all of the sugars in the nucleic acid backbone are 2'-OMe-deoxyribose.

As described in more detail elsewhere herein, in certain aspects, the osmylated probe can be prepared by reacting an aqueous solution comprising a substituted or unsubstituted 2,2'-bipyridine and an OsO4 (osmylating reagent) with an oligonucleotide to form the 2,2'-bipyridine-OsO4-conjugated probe. In certain aspects, the conjugated probe is purified from excess osmylating reagent. In certain aspects, the 2,2'-bipyridine/OsO4 ratio in the solution is equimolar or near equimolar. For example, in certain aspects, the 2,2'-bipyridine/OsO4 ratio in the solution is about 0.80.11.0, 0.85/1.0, 0.90/1.0, 0.95/1.0, 0.97/1.0, 0.98/1.0, 0.99/1.0, 1.0/1.0, 1.0/0.99, 1.0/0.98, 1.0/0.97, 1.0/0.95, 1.0/0.90, 1.010.85, or 1.010.80. Alternative methods of preparing the osmylated probe exist and are contemplated. For example, in certain aspects, the osmylated probe is prepared by ligation of a (dT(OsBp))n oligo to the 5'-end or 3'-end of the probe, wherein n is 2, 3, or 4.

Provided for herein are kits comprising reagents for performing the methods of this disclosure. In certain aspects, a kit comprises an osmylated probe of this disclosure and a control nucleic acid target molecule that can hybridize to the probe. In certain aspects, the control nucleic acid target comprises a nucleic acid sequence of a ctDNA, cDNA, miRNA, a fragmented coding RNA, or a non-coding RNA. In certain aspects, the non-coding RNA is less than about 300 bases long.

Also provided for herein is the use of a probe of this disclosure for the detection of a nucleic acid target molecule with a nanopore device, wherein the nucleic acid target molecule is optionally a ctDNA, cfDNA, miRNA, a fragmented coding RNA, or a non-coding RNA. In certain aspects, the non-coding RNA is less than about 300 bases long.

EXAMPLES

Materials and Methods

Oligos and other Reagents

Custom-made RNA oligos were purchased from Dharmacon (Horizon Discovery Group). Custom-made deoxyoligos were purchased from Integrated DNA Technologies (IDT). Sequences and UV/Vis properties of their osmylated derivatives are listed in Table 1. The purity of oligos was tested by HPLC and typically found to be >85%. Oligos were diluted with Ambion Nuclease-free water, not DEPC treated, from Thermo Fisher Scientific typically to 100 or 200 µM stock solutions and stored at −20° C. HPLC profiles from the analyses of both the intact and the osmylated oligo are included elsewhere herein. Buffer DNase-free and RNAse-free TRIS.HCl 1.0 M pH 8.0 Ultrapure was purchased from Invitrogen and used to prepare the HPLC mobile phase. NaCl crystalline ACS min 99.0% was obtained from Alfa Aesar. Distilled water from Alhambra was used for preparation of HPLC mobile phase. A 4% aqueous osmium tetroxide solution (0.1575 M OsO4 in ampules at 2 mL each) was purchased from Electron Microscopy Sciences. 2,2'-Bipyridine 99+% (bipy) was purchased from Acros Organics. Human Serum from human male AB plasma and NaOH 1N Bioreagent were purchased from Sigma. ss M13mp18, primer M13(fwd6097), NEBuffer 2.1, and Klenow Fragment of DNA Polymerase 1 (3'-5 exo)(M0212) were kindly provided by New England Biolabs, Ipswich, MA, USA.

While not limiting on the probes of this disclosure, expense and product quality considerations led to selection of DNA over RNA oligos as probes for most example experiments. These experiments revolved around optimizing the probe's design to make it of general applicability, and aptly detectable by available nanopore systems (e.g., the ONT/CsGg nanopore). In certain aspects, a probe that successfully identified miRNA targets at the single-digit attomole level has sequence complementary or at least partially complementary to the nucleic acid target molecule, 2'-OMeU (mU) replacing T within the sequence, 3 additional adjacent T residues at the 5'-end, and 3 added dA residues at the 3'-end. The oligo is osmylated to add 4 to 5 OsBp tags per molecule, 3 of which occupy the 5'-end, and the other 1 or 2 are randomly allocated within the sequence. Due to the heavy crowding at the one end of the probe, applied voltage in the range of −210±10 mV was required for translocation and detection of this illustrative probe. This feature was advantageous, as it allows for depletion of non-target material at −180 mV prior to performing the diagnostic experiment at −210 mV. Probes may also be multiplexed when using probe designs that exhibit distinct nanopore profiles. Preliminary experiments in 15% human serum suggest that probes and the resulting hybrids are stable in such medium, and show the feasibility for identifying short DNA and RNA from body fluid samples using the OsBp with a nanopore platform.

Example 1

(Pyrimidine)OsBp is a Chromophore

Selective labeling of a nucleic acid requires an assay for quality control. Addition of OsBp to the C5-C6 Py double bond and formation of Py(OsBp) creates a new chromophore in the wavelength range of 300 to 320 nm (Kanavarioti, A. et al. (2012)), where nucleic acids exhibit negligible absorbance. This observation was exploited using a deoxyoligo training set to show that extent of osmylation can be measured using the equation: $R(312/272)=2\times$(No of osmylated pyrimidines/total nt of nucleotides) (Kanavarioti, A. et al. (2012)). Value $R(312/272)$ is the ratio of the observed peak absorbance at 312 nm over the observed peak absorbance at 272 nm (the peak shape could be sharp or broad or multiple peaks) (Kanavarioti, A. (2016)). The wavelengths 312 nm and 272 nm were chosen in order to maximize the effect and to equalize contributions by different pyrimidines (Kanavarioti, A. (2016)). Absorbance at 272 nm is about 75% of the absorbance at 260 nm practically for either intact or osmylated nucleic acids. Using the ratio R instead of the absorbance at 312 nm normalizes the measurement, and minimizes instrument sampling variation.

As deduced by experimenting with an oligo training set, when observed value $R(312/272)=2\times$(# of pyrimidines-total # of nucleotides), osmylation is practically 100% complete and all the pyrimidines carry one OsBp moiety (Kanavarioti, A. et al. (2012); Kanavarioti, A. (2016)). When observed $R(312/272)<2\times$(# of pyrimidines/total # of nucleotides), osmylation is partial and the number of osmylated pyrimidines or OsBp moieties can be calculated based on the same equation (see Table 1). With partial osmylation the number obtained from the equation refers to OsBp moieties, on average. Molecules carry an integer number of OsBp moieties and therefore some molecules will have fewer, and some molecules will have more than the calculated value distributed in a statistically unbiased manner. It has been shown that osmylation occurs randomly, but depends on the relative reactivity of OsBp for the pyrimidines. Relative reactivity towards osmylation, determined by kinetic measurements at 26° C. in water using deoxyribooligos T/dC=28, dU/dC=3.75 and therefore T/dU=7.5 (Ding, Y. & Kanavarioti, (2016)), and using ribooligos U/C=4.7 and 5-MeU/C=44; hence 5-MeU/U=9.3, with 5-MeU carrying the identical nucleobase as T, (Kanavarioti. A. (2016)). Because of the markedly higher reactivity of OsBp towards T, compared to dU or U and dC or C, conditions can be found to osmylate practically 100% all Ts, while some dU and very few dC become osmylated (Kanavarioti, A. et al. (2012)). This dramatically higher reactivity was exploited by adding 3 Ts at the 5'-end of a probe, replacing the Ts in the sequence with dU or mU, and optimizing the manufacturing process as detailed below.

Example 2

Manufacturing of OsBp-Nucleic Acids

OsBp reagent was prepared by weighing the equivalent of 15.7 mM of bipy (49.2 mg) in a 20 mL scintillation vial, adding 18 mL of water and stirring at room temperature until bipy dissolved, followed by transferring the full content of a 2 mL 4% $OsO_4$ solution supplied in an ampule. Dissolving bipy in water before the addition of $OsO_4$ (protocols a, b, c, and d) results in a more consistent and potent preparation compared to dissolving bipy after the addition of $OsO_4$ (protocol o). The transfer was done using a glass pipette inside a safety hood (MSDS and Information is obtained from the following link to UCLA Chemistry Department on the world wide web at chemistry.ucla.edu/sites/default/files/safety/sop/SOP_Osmium_Tetroxide.pdf). The resulting solution is an aqueous 20 mL 15.75 mM OsBp (0.4%) stock solution, equimolar in $OsO_4$ and bipy. The concentration of the OsBp stock solution is limited by the solubility of bipy in water and adding $OsO_4$ does not increase it, as the complex has a low association constant. OsBp complex represents an approximate 5% of the total, as measured by CE (Kanavarioti, A. et al. (2012)). Care should be taken that this preparation, as well as any other work using OsBp is conducted in stoppered glass vials in a well-ventilated area. Leftover solutions of $OsO_4$ and/or OsBp may be mixed with corn oil to neutralize unreacted $OsO_4$ and properly discarded based on specific local regulations (MSDS and Information is obtained from the following link to UCLA Chemistry Department on the world wide web at chemistry.ucia.edu/sites/default/files/safety/sop/SOP_Osmium_Tetroxide.pdf). The freshly prepared OsBp stock solution was dispensed in HPLC vials and kept at −20° C. Each vial can be stored at 4° C. and used for a month without loss of potency; typical pipette tips can be used for manufacturing of OsBp-labeled nucleic acids. OsBp stock solutions should be validated before first use by running a known reaction. For osmylation reactions a 20-fold excess of OsBp over the reactive pyrimidine in monomer equivalents was used to ensure pseudo-first order kinetics, and to assure successful use of protocols. Manufacturing conditions, i.e., OsBp concentration and labeling duration varies significantly depending on the presence of T, and the desired result of osmylating all pyrimidines, T only, or just a fraction of dC and dU in DNA and a fraction of C and U in RNA. For the purpose of this study, when T-osmylation is required, protocol b is recommended, and when partial osmylation of U and C is required, protocol c or protocol d are recommended. These choices were facilitated by testing additional protocols (o and a), as identified in Table 1. Quenching of the osmylation reaction occurs upon purification. Purification from excess OsBp was done with spin columns (TC-100 FC from TrimGen Corporation) according to the manufacturer's instructions. Briefly, spin columns are filled with the manufacturer's proprietary solution and centrifuged at 4,000 rpm for 4 min; the resulting solution and the microcentrifuge tube are discarded. Then 40 to 120 µL of an osmylation reaction mixture is transferred to the spin column and centrifuged at 4,000 rpm for 4 min using a clean microcentrifuge tube. The centrifuged solution is the purified osmylated oligo. This purification method retains the volume/concentration of the sample, and close to 100% recovery of oligo is achieved.

Recommended protocol b for thymidine (T)-osmylation is 30±2 min incubation with 2.6 mM OsBp in water at room temperature (see Table 1 under b). Recommended protocol for partial U- and C-osmylation of probes that do not carry dTs is 30±2 min with 3.9 mM OsBp in water at room temperature (see Table 1 under c) or 30±2 min with 5.2 mM OsBp protocol (see Table 1 under d). There were two additional protocols tested, but these were found to be less optimal: Protocol where bipy was not dissolved in water prior to the $OsO_4$ addition and used 40 min incubation with 2.6 mM OsBp (see Table 1 under o) and the protocol using 45 min incubation with 2.6 mM OsBp (see Table 1 under a). The presence of 2'-OMe groups does not affect markedly the extent of osmylation, as seen by comparable osmylation extent for 100 nt RNA and 100 nt RNA(2'-OMe) that carries about 50% 2'-OMe bases. The extent of osmylation can be affected by the number of U in the oligo as seen in FIG. 14. This is because the reactivity of OsBp towards dU is 3.75 times higher compared to the reactivity towards dC and the reactivity of OsBp towards U is 4.7 times higher compared to the reactivity towards C. Because the osmylation protocols do not go to completion dU(OsBp) or mU(OsBp) are kinetically preferred over dC(OsBp) and U(OsBp) preferred over C(OsBp). With protocol b, osmylation of other pyrimidines is negligible compared to T-osmylation, but with protocol c, the extent of osmylation towards U, dU, mU and dC is measurable. FIG. 14 suggests a linear correlation between the number of OsBp moieties and the number of U present in an oligo spanning from 22 nt to 100 nt oligos. One may use the slope=0.43 of the graph to estimate extent of osmylation with protocol c for any oligo based on the number of Us in the sequence.

2 mL HPLC vials fitted with 120µL glass inserts were used to carry the manufacturing reactions. Removing the reaction product from these inserts and transferring it onto the purification spin column requires a long and narrow 20 µL pipette tip. Osmylated nucleic acids are as stable as the corresponding nucleic acid, and the OsBp label is unreactive. They can be stored in the 1.5 mL microcentrifuge tubes, at −20° C. for years. The concentrations of 2.6, 3.9 and 5.2 mM correspond to 1/6, 1/4 and 1/3 dilutions of the 15.75 mM OsBp stock solution, respectively. Deviations from these two protocols are included in the table, identified as protocols o and a. The additional protocol (d) was used in order to achieve higher extent of osmylation with probes that do not contain any T, such as dmiR21(OMe), and make it a detectable probe (see Brief Description of FIG. 21A).

Example 3

Enzymatic Elongation Reactions

The ability of DNA polymerase to extend an osmylated primer was examined in vitro using ssM13mp18 annealed to unmodified and osmylated oligonucleotides. ssM13mp18 at a concentration of 42 nM was mixed with 0.42 µM primer in NEBuffer 2.1 (New England Biolabs). Samples were heated to 90° C. for 30 seconds and cooled to 25° C. at 0.1° C./sec. Polymerization reactions contained these annealed complexes (8.4 nM ssM13mp18), 1.25×NEBuffer 2.1, 0.25 mM each of dGTP, dATP, and dTTP, 0.025 mM α-[$^{32}$P] dCTP, and 7.7 U/nil Klenow Fragment of DNA Polymerase I (3'-5' exo-) (NEB, M0212). Reactions were incubated at 37° C. and incorporation of labeled dCMP was monitored by an acid precipitation assay. Time points were taken at 5, 10, and 20 minutes.

Figure 3A:
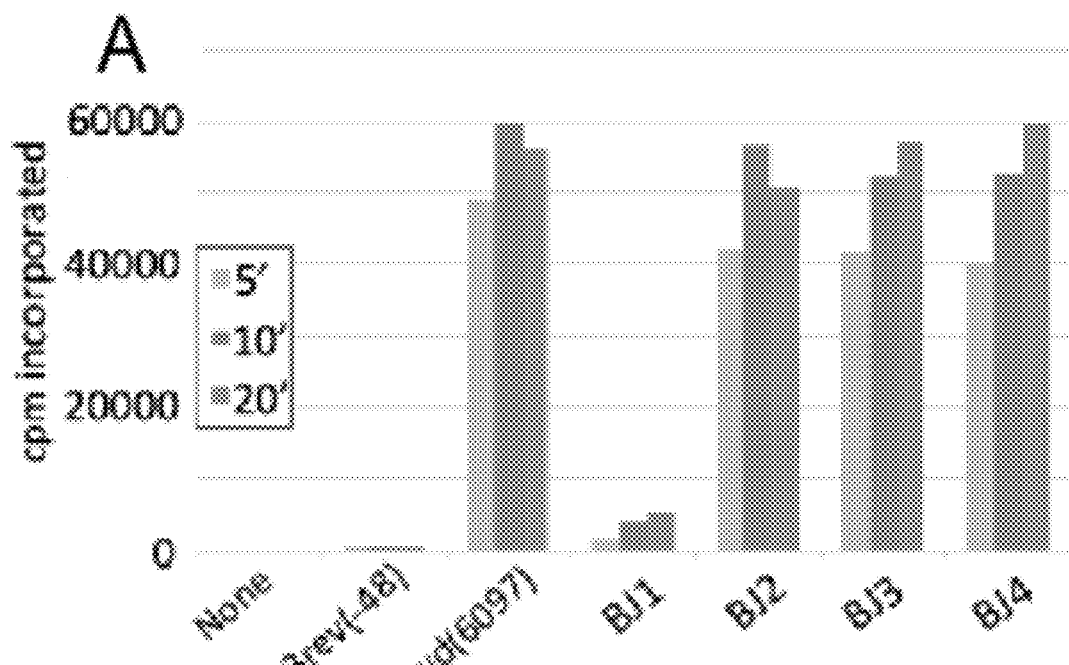

As seen in FIG. 3A, no incorporation was noted when no oligonucleotide was added, or if the oligonucleotide, primerM13rev(−48), was not complementary to the ssM13mp18. In contrast, most oligonucleotides predicted to anneal to the DNA template gave robust incorporation, even when osmylated, with maximal incorporation corresponding to roughly one round of replication on the M13mp18 DNA template. Incorporation noted for M13(fwd6097), BJ2, BJ3, and BJ4 were equivalent despite interior single base mismatches within BJ3 and BJ4 (see sequences in Table 1). Despite overall equivalent osmylation levels for BJ2, BJ3 and BJ4, markedly lower levels of incorporation were noted for BJ1, most likely due to presence of OsBp at the terminal 3'-T(OsBp) residue. Control experiments mixing BJ1 with M13(fwd6097) displayed full incorporation, discounting soluble inhibitors as the cause of low incorporation with BJ1 (data not shown).

Example 4

HPLC Methods

An HPLC method to assess oligo purity was developed and used here to assess purity of the oligos listed in the Table 1. This method was optimized and used to assess hybridization between two oligos in a mixture; validation of this method was conducted using a 1:1 mixture of intact oligos known to hybridize (see FIG. 3B and FIG. 10A). Analyses were conducted automatically using a thermostated autosampler. HPLC peaks were detected and identified using a diode array detector (DAD) in the UV-vis region 200-450 nm. The chromatograms were recorded at 260, 272, and 312 nm and reported here selectively. Samples were prepared with RNAse free water, but buffers were not.

For HPLC analysis an Agilent 1100/1200 LC HPLC equipped with a binary pump was used, Diode Array Detector (DAD), a 1290 Infinity Autosampler/Thermostat, and Chemstation software Rev.B.04.01 SPI for data acquisition and processing. For sample analyses IEX HPLC column DNAPac PA200 from ThermoFisher Scientific (Dionex) was used in a 2×250 mm configuration. The performance of the instrument and the column was qualified using standards every time ahead as well as after analysis of research samples. The HPLC method was developed to assess hybridization in a sample approximately 90% in aqueous ONT buffer at pH 8 and column thermostat at 35° C. This HPLC method (identified as HPLC method B) uses the DNAPac PA200 column with a 0.45 mL/min flow, mobile phase A (MPA) aqueous 25 mM TRIS.HCl pH 8 buffer, mobile phase B (MPB) aqueous 1.5M NaCl in a 25 mM TRIS.HCl pH 8 buffer, a gradient from 10% MPB to 50% MPB in 20 min and an additional 10 min for wash and equilibration to initial conditions, i.e. 90% MPA. Column temperature was set at 35° C. to mimic the flow cell temperature. To include the 100 nt RNA the chromatography was modified to HPLC Method C. Specifically the gradient was made steeper, 10% MPB to 75% MPB in 20 min, and everything else remained as is. Because of the approximately neutral pH the long 100 nt RNA elutes as a broad peak resembling a mixture. This is because aqueous pH 8 does not denature the various conformations of a long RNA, as reported earlier (Kanavarioti, A. (2019)). ONT buffer has a UV-Vis component that in this chromatography elutes in the void volume and does not interfere with the analysis of the samples. Sample injection volume was typically at 5 µL, and not higher than 10 µL. The hybridization test can be used in conjunction with samples in ONT buffer or any other medium that favors complexation. Some of the oligos and their osmylated derivatives were analyzed using a method identified as HPLC method A, which is recommended for oligo purity analysis (Kanavarioti, A. (2019)), but not suitable to test hybridization. HPLC method A uses the DNAPac PA200 column with a 0.45 mL/min flow, and column temperature at 30° C. Mobile phase A (MPA) aqueous pH 12.0±0.2 with 0.01 N NaOH, mobile phase B (MPB) aqueous 1.5M NaCl in pH 12.0±0.2 with 0.01 N NaOH, a gradient from 20% MPB to 95% MPB in 12 min and an additional 8 min for wash and equilibration to initial conditions, i.e. 80% MPA.

Example 5

Single Molecule Ion-Channel Conductance Experiments with the CsGg Nanopore in a MinION or a Flongle (ONT Platform)

ONT instructions were followed in order to remove air bubbles from the flow cell, flush the storage solution with ONT Flush buffer, add sample, or store the flow cell, as needed. Instructions for MinION (75 µL sample) and Flongle (30 µL sample) are obtained from the protocols found on the ONT website. Flongle flow cells require an adaptor but work on the same device as the MinION flow cells. The software MINKNOW to run the nanopore experiments was downloaded on a MacBook Pro laptop used for these experiments. All the functions necessary to test the flow cell and run the experiments are done via the MINKNOW software tool. Raw data files were acquired in fast-5 format, which were then analyzed by the OsBp_detect software. Size of fast-5 files for the experiments depend on the flow cell and experiment duration and vary between 1.5 and 6 GB. Fast-5 files can be directly visualized in MatLab (from Mathworks) 2D format, once the experiment is completed. MINKNOW allows for monitoring in real time any chosen channel, up to 10 channels, so one doesn't need to wait for the experiment to be done to see the i-t recordings.

Added samples were either untagged oligos, osmylated oligos, or mixtures thereof. Concentrations were typically at or below 10 µM oligo in no less than 80% of ONT buffer. No library was prepared, and no processing enzyme was added, such that all the translocations reported here are unassisted and voltage-driven. Experiments lasted no longer than 1.5 h, but the same experiment could be extended by stopping it, and restarting it later, or next day without adding a new sample. Running the same flow cell for more than 4 hours per day was avoided, and flow cells were stored temporarily in ONT buffer. Cleaning with buffer the flow cell before running a new sample was done right before the next experiment. In most cases the first experiment was a "buffer test" to assess the low cell's baseline. Duration of the buffer test was kept as short as possible, because the nanopores of a flow cell did not last for more than 15 hours under our experimental conditions. Per ONT protocol, applied voltage was raised by about 10 mV for every 5 working hours, in an attempt to keep the open pore ionic current ($I_o$) constant. This is why experiments compared to one another are done at seemingly different applied voltage. The MinION flow cell has over 2000 nanopores, but only 512 are monitored simultaneously. During the first few experiments on a flow cell, nanopores become inactive, but they are replaced with new working ones. Therefore, the first 4 to 5 experiments are practically done with the same number of pores. After that the number of working nanopores decreases by 5 to 10% per hour. It is worth noting that while most of the working nanopores exhibited comparable number of events within a factor of 5 from lowest to highest, a small percentage deviated and recorded markedly higher count of events. These pores were called "outliers" and it was estimated approximately 2.5% of nanopores to be outliers. The analysis of the data presented here includes all channels. Additional analysis of all the experiments was performed by excluding the outliers, and even though the actual counts were different, the trends and conclusions are identical to the ones presented here.

Example 6

Event Detection Algorithm—OsBp_Detect

Let y be an ordered sequence of real values representing a typical time-series obtained from a single Nanopore. We categorize regions of y into one of two states: current from an open channel, $I_o$, where the Nanopore is unoccupied, and the residual current when some translocation event is taking place, $I_r$. For the high-throughput characterization of a single translocation event corresponding to an OsBp-tagged oligonucleotide, we propose a segmentation algorithm that can determine the start and end positions in y for all events of interest based on user-defined thresholds. The analysis pipeline is divided into three steps:

1. Baseline current estimation
2. Identification of potential candidate events
3. Event filtering based on event features First, the baseline $I_o$, $b_o$, is established by taking a median of the signal values between estimated lower and upper bounds, $\{o_{low}, o_{up}\}$, of the open current: $b_o=\text{med}(\{i:i\in y, o_{low}<i<o_{up}\})$.

While the signal noise is dependent on the nanopore platform used, the sharp transitions between the $I_o$ and $I_r$ states from osmium-tagged oligos permit the use of a single threshold-based parser for event detection pipeline. With this approach, events are identified if they pass a set threshold away from the local baseline level. The threshold is defined by parameter $b_{all}$ which should be low enough to capture as many translocation events as possible. By default, $b_{all}=b_o\cdot(1-(10\cdot\sigma_o/b_o))$ where au represents the signal noise of the open current. The noise constant, a., is determined by splitting y into small segments (segment size used, n=100, 000) and calculating the global standard deviation of the open current signal values, $\sigma(\{i:i\in y, o_{low}<i<o_{up}\})$. The as value additionally provides a useful quality control metric to detect pores with unstable baselines and large events rates or pores that have been blocked.

Finally, for the qualification of valid translocation events, two filtering conditions were applied to the identified events. The filters correspond to the minimum and maximum event length defined by parameters, $\{t_{min},t_{max}\}$, and the range of lowest residual current, $\{b_{min},b_{max}\}$, expressed as a ratio with respect to $b_o$. The event length thresholds, $\{t_{min},t_{max}\}$, can be adjusted to monitor the speed of translocation whereas $\{b_{min},b_{max}\}$ enables the separation of OsBp-tagged and untagged oligo species. Let $\tau_1$ and $\tau_2$ represent the starting and ending indices for any given event in y. For $y_{\tau_1:\tau_2}$ to be classified as a potential OsBp translocation event, both of the following conditions must hold:

$$\gg t_{min} < \tau_2 - \tau_1 < t_{max}$$

$$\gg b_{min} < \frac{\min(y_{\tau_1:\tau_2})}{b_o} < b_{max} \quad 5$$

The event detection pipeline is available as a Python library, 'osbp_detect'. A cross-platform graphical user interface has been included, to enable direct reporting of translocation events from ONT bulk fast5 tiles (hypertext transfer protocol secure github.com/kangaroo96/osbp_detect).

TABLE 1

List of tested DNA or RNA oligos. The 3 miRNAs tested here have the sequence of the corresponding miRNA-5p. Oligo ID, sequence, number of thymidines over total nucleotides (T/total nt), number of pyrimidines over total nucleotides (Py/nt), theoretical R(312/272) for T(OsBp) (see footnotes and Examples), Observed R(312/272) is the ratio of the observed areas under the HPLC peak at 312 nm over the area at 272 nm; HPLC analytical profiles for each oligo and its osmylated conjugate are included elsewhere herein. The number of Py(OsBp) or OsBp moieties, on average, depends on the protocol used for osmylation and is calculated as described in footnote 3 below.

| ID, DNA unless identified as RNA | Sequence; sequences are all deoxyribose, with the exception of the three miRNAs, T8 and 100 nt RNA; (mU is 2'-OMeU) | T/total nt | Theoretical R(312/272)[1] T(OsBp) only | Observed R(312/272)[2] | Py/total nt | No of OsBp[3] on average | SEQ ID NO: |
|---|---|---|---|---|---|---|---|
| PrimerM13for(-20) | GTA AAA CGA CGG CCA GT | 2/17 | 0.235 | 0.230$^o$ | 6/17 | 1.955$^o$ | 1 |
| PrimerM13for(-41) | CGC CAG GGT TTT CCC AGT CAC GAC | 5/24 | 0.417 | 0.416$^o$ | 14/24 | 4.992$^o$ | 2 |
| PrimerM13rev(-27) | CAG GAA ACA GCT ATG AC | 2/17 | 0.235 | 0.236$^o$ | 6/17 | 2.006$^o$ | 3 |
| PrimerM13rev(-48) | AGC GGA TAA CAA TTT CAC ACA GG | 4/23 | 0.348 | 0.326$^o$ | 9/23 | 3.749$^o$ | 4 |
| Complement primerM13for(-20) | TTG GCA CTG GCC GTC GTT TTA CAA CGT GAC TG | 11/35 | 0.629 | 0.578$^o$ | 20/35 | 10.1150$^o$ | 5 |
| BJ1 | CAG TCA CGA CGT TGT AAA ACG GCC AGT | 5/30 | 0.333 | 0.295$^o$ 0.327$^b$ | 13/30 | 4.425$^o$ 4.905$^b$ | 6 |
| BJ1EXT(mU) | TTT GmUA AAA CGA CGG CCA GmUA AA | 3/23 | 0.261 | 0.273$^b$ | 9/30 | 3.1400 | 7 |
| Complement primerM13for(-41) | ACA ACG TCG TGA CTG GGA AAA CCC TGG CGT TAC CC | 6/35 | 0.333 | 0.344$^o$ | 17/35 | 6.020$^o$ | 8 |
| BJ2 | GGG TAA CGC CAG GGT TTT CCC AGT CAC GAC | 6/30 | 0.400 | 0.401$^o$ 0.401$^b$ | 15/30 | 6.015$^o$ 6.015$^b$ | 9 |
| BJ3 | GGG TAA CGC CAG GGT TTC CCC AGT CAC GAC | 5/30 | 0.333 | 0.347$^o$ 0.353$^b$ | 15/30 | 5.205$^o$ 5.295$^b$ | 10 |
| BJ4 | GGG TAA CGC CAG GGT TTT TCC AGT CAC GAC | 7/30 | 0.467 | 0.452$^o$, 0.445$^b$ | 15/30 | 6.780$^o$ 6.675$^o$ | 11 |
| BJ2 TA(OMe) | TTT CGC CAG GGU UUU CCC AGU CAC GAC AAA (all 2'-OMe with the exception of Ts) | 3/30 | 0.200 | 0.324$^a$ | 17/30 | 4.860$^a$ | 12 |
| BJ2 AT(OMe) | AAA CGC CAG GGU UUU CCC AGU CAC GAC TTT (all 2'-OMe with the exception of Ts) | 3/30 | 0.200 | 0.311$^a$ | 17/30 | 4.665$^a$ | 13 |
| BJ2EXT(mU) | TTT CGC CAG GGmU mUmUmU CCC AGmU CAC GAC AAA | 3/30 | 0.200 | 0.278$^b$ | 17/30 | 4.170$^b$ | 14 |
| miRNA21, RNA | UAG CUU AUC AGA CUG AUG UUG A | 0/22 | — | 0.268$^c$ | 11/22 | 2.950$^c$ | 15 |
| miRNA21-A$_{15}$, RNA | UAG CUU AUC AGA CUG AUG UUG A$_{16}$ | 0/37 | — | 0.099$^o$ | 11/37 | 1.832$^o$ | 16 |
| Complement miRNA-21, RNA | UCA ACA UCA GUC UGA UAA GCU A | 0/22 | — | 0.183$^c$ | 11/22 | 2.013$^c$ | 17 |
| dmiR21 | TCA ACA TCA GTC TGA TAA GCT A | 6/22 | 0.545 | 0.485$^o$ | 11/22 | 5.339$^o$ | 18 |
| 21EXT | TTT CAA CAT CAG TCT GAT AAG CTA | 8/24 | 0.667 | 0.665$^o$ | 13/24 | 8.000$^o$ | 19 |
| dmiR21(OMe) | UCA ACA UCA GUC UGA UAA GCU A (all 2'-OMe) | 0/22 | — | 0.082$^b$, 0.124$^c$ 0.26$^d$ | 11/22 | 0.902$^b$, 1.365$^c$ 2.85$^d$ | 20 |
| 21EXT(mU) | TTT CAA CAmU CAG mUCmU GAmU AAG CmU AAA | 3/27 | 0.231 | 0.433$^a$, 0.344$^b$ | 13/27 | 5.846$^a$ 4.644$^b$ | 21 |
| miRNA122, RNA | UGG AGU GUG ACA AUG GUG UUU G | 0/22 | — | 0.277$^o$ | 9/22 | 3.04$^c$ | 22 |

TABLE 1-continued

List of tested DNA or RNA oligos. The 3 miRNAs tested here have the sequence of the corresponding miRNA-5p.
Oligo ID, sequence, number of thymidines over total nucleotides (T/total nt), number of pyrimidines over total nucleotides
(Py/nt), theoretical R(312/272) for T(OsBp) (see footnotes and Examples), Observed R(312/272) is the ratio of the observed areas
under the HPLC peak at 312 nm over the area at 272 nm; HPLC analytical profiles for each oligo and its osmylated conjugate are
included elsewhere herein. The number of Py(OsBp) or OsBp moieties, on average, depends on the protocol used for osmylation
and is calculated as described in footnote 3 below.

| ID, DNA unless identified as RNA | Sequence; sequences are all deoxyribose, with the exception of the three miRNAs, T8 and 100 nt RNA; (mU is 2'-OMeU) | T/total nt | Theoretical R(312/272)[1] T(OsBp) only | Observed R(312/272)[2] | Py/total nt | No of OsBp[3] on average | SEQ ID NO: |
|---|---|---|---|---|---|---|---|
| Complement miRNA122, RNA | CAA ACA CCA UUG UCA CAC UCC A | 0/22 | — | 0.143$^c$ | 13/22 | 1.573$^c$ | 23 |
| dmiR 122 | CAA ACA CCA TTG TCA CAC TCC A | 4/22 | 0.364 | 0.404$^o$ | 13/22 | 4.444$^o$ | 24 |
| 2XdmiR122 | (CAA ACA CCA TTG TCA CAC TCC A)$_2$ | 8/44 | 0.364 | 0.380$^o$ | 26/44 | 8.36$^o$ | 25 |
| 122EXT | TTT CAA ACA CCA TTG TCA CAC TCC A | 7/25 | 0.560 | 0.602$^o$ | 16/25 | 7.525$^o$ | 26 |
| dmiR122(OMe) | C AAA CAC CAU UGU CAC ACU CCA (all 2'-OMe) | 0/22 | — | 0.088$^b$, 0.150$^c$ | 13/22 | 0.965$^b$, 1.654$^c$ | 27 |
| miRNA140, RNA | CAG UGG UUU UAC CCU AUG GUA G | 0/22 | — | 0.233$^c$ | 12/22 | 2.563$^c$ | 28 |
| dmiR140 | CTA CCA TAG GGT AAA ACC ACT G | 4/22 | 0.364 | 0.357$^o$ | 10/22 | 3.926$^o$ | 29 |
| 2XdmiR140 | (CTA CCA TAG GGT AAA ACC ACT G)$_2$ | 8/44 | 0.364 | 0.321$^o$ | 20/44 | 7.055$^o$ | 30 |
| 140EXT(mU) | TTT CmUA CCA mUAG GGmU AAA ACC ACmU GAA | 3/27 | 0.222 | 0.374$^a$, 0.314$^b$ | 13/27 | 5.049$^a$ 4.239$^b$ | 31 |
| d(CT)$_{10}$ | CTCTCTCTCTCTCTCTCTCT | 10/20 | 1.00 | 1.044$^b$ | 20/20 | 10.44$^b$ | 32 |
| T8, RNA | (AG)$_4$C$_2$(AG)$_4$C$_2$(AG)$_3$CCUUC A, foot note 4 | 0/32 | — | 0.50 | 9/32 | 8.0 | 33 |
| 100nt RNA | foot note 5 | 0/100 | — | 0.239$^c$ | | 11.96$^c$ | 34 |
| 100nt RNA(OMe) | foot note 6 | 0/100 | — | 0.224$^c$ | | 11.199$^c$ | 35 |

Underlined partial sequences correspond to M13primers with or without a mismatch.
[1]Theoretical R(312/272) for T only equals 2 × (No of T)/(total nt) (see Experimental Section).
[2]Observed R(312/272) is the observed Absorbance at 312 nm divided by the observed absorbance at 272 nm from HPLC. Observed R(312/272) =2 × (No of Py(OsBp)/(total nt) (see Experimental Section).
[3]No of OsBp, on average, is determined fromt the equation above, and it is equal to observed R(312/272) × (total nt)/2.
$^{o, a, b, c, d}$are different protocols for preparing osmylated oligos: $^o$batch of OsBp stock solution prepared without dissolving bipy ahead of OsO$_4$ addition, 40 min with 2.625 mM OsBp. $^{a, b,}$ $^c$batch of OsBp stock solution prepared by dissolving bipy before adding OsO$_4$; a45 min with 2.625 mM OsBp: $^b$30 min with 2.625 mM OsBp: $^c$30 min with 3.94 mM OsBp. $^d$Special protocol (30 min with 5.25 mM OsBp) to add about 3 OsBp per 22nt oligo in the absence of Ts.
[4]Practically 100% osmylated at all pyrimidines (Sultan M., Kanavarioti, A. (2019).).
[5]100nt RNA sequence: 5'-UUA CAG CCA CGU CUA CAG UUU UAG AGC UAG AAA UAG CAA GUU AAA AUA AGG CUA GUC CGU UAU CAA CUU GAA AAA GUG GCA CCG AGU CGG UGC UUU U-3' (SEQ ID NO: 34).
[6]100nt RNA(OMe) sequence: 5'-mUmUmA CAG CCA CGU CUA CAG UUU UAG AmGmC mUmAmG mAmAmA mUmAmG mCAA GUU AAA AUA AGG CUA GUC CGU UAU CAmA mCmUmU mGmAmA mAmAmA mGmUmG mGmCmA mCmCmG mAmGmU mCmGmG mUmGmC mUmUmU mU-3'; m stands for 2'-OMe (SEQ ID NO: 35).

RESULTS AND DISCUSSION

The materials used in this study were all synthetic oligos of the highest purity and are listed in Table 1. Osmylation protocols were developed by us. Intact and osmylated nucleic acids were further characterized in-house by validated HPLC methods (Kanavarioti, A. (2019)). Nanopore experiments were conducted using the ONT devices and the ONT supplied Flush buffer (ONT buffer or buffer), in addition to company's instructions of how to prime the flow cell, add the sample, select voltage, and acquire the raw i-t traces. No sample library was prepared and no enzyme-assistance was exploited. Samples were prepared in 90-95% ONT buffer, unless otherwise noted. The nanopore experiments reported here were conducted at the factory-preset, flow cell temperature in the range of 34-35° C. The raw i-t traces of all channels (a fast5 file) were captured and analyzed using OsBp_detect software (Kanavarioti, A., & Kang, A. See RNA(OsBp) event detection Python package in a public repository: hypertext transfer protocol secure github.com/kangaroo9%/osbp_detect and for step-by-step installation instructions see here: hypertext transfer protocol secure github.com/kangaroo96/osbp_detect/blob/master/instructions.md). The output, a tsv file, is read using Microsoft Excel. It lists $I_0$ value for each channel, as well as the selected events and their $I_r$ value from which $I_r/I_o$ is calculated. It also lists the times, in data time points, of the beginning and of the end of each event (FIG. 8). OsBp_detect permits manual setting of parameters, in order to select events of interest (Kanavarioti, A., & Kang, A. See RNA (OsBp) event detection Python package in a public repository: hypertext transfer protocol secure at github.com/kangaroo96/osbp_detect and for step-by-step installation instructions see here: hypertext transfer protocol secure at github.com-kangaroo96/osbp_detect/blob/master/instructions.md). Here we selected events with residence time $4<\tau<300$ data time points or the equivalent $1.3<\tau<100$ ms, and fractional residual ion current $I_r/I_o \leq 0.55$ (FIG. 1B). FIG. 2, FIG. 4, FIG. 5, FIG. 6, and FIG. 7 present histograms of count of events (abbreviated as counts or events) as a function of $I_r/I_o$ using a 0.05 bin.

Nanopore Experiments Using the Flongle Flow Cell

FIG. 2 illustrates results exploiting the Flongle flow cell. FIG. 2A was a first attempt to observe a hybrid. It was known from earlier work with the MinION flow cell that T8, a 32 nt RNA with 9 pyrimidines and a total of 8 OsBp tags (see sequence in Table 1), requires high voltage to traverse, exhibits multiple translocation events, and severely obstructs the ionic current exhibiting a maximum of counts at $(I_r/I_o)max \approx 0.1$. Repeating the experiment practically duplicated the earlier work on the MinION (Sultan M., Kanavarioti, A. (2019)). Even though not a perfect complement, $d(TC)_{10}$ was used to form the ds complex, as $d(CT)_{10}$ can base-pair 16 out of 20 nt, including 8 GC pairs, with T8. While the experiment with probe T8 exhibited, on average, 400 events per channel, the experiment using a 1:1 mixture of probe T8 and $d(CT)_{10}$, yielded less than 50 events per channel for some channels and zero events reported for the rest (FIG. 9A-D). FIG. 2B illustrates a test for identification of miRNA122 (Li. X-D. et al. (2017)). The probe used here is dmiR122, the exact deoxy complement of miRNA122, and carries 4 T(OsBp) (see Table 1). The sample with probe dmiR122 alone exhibited numerous counts, while the sample with an approximate equimolar mixture of this probe and miRNA122 exhibited markedly fewer counts. A third sample with a 4-times higher miRNA load, composed of miRNA21 (Thum, T. et al. (2008): Lai, J. Y. et al. (2017); Fulci, V. et al. (2007); Wang. Y. et al. (2020)) and miRNA140 (Li, X-D. et al. (2017)) also exhibited fewer counts compared to the probe sample. The latter suggests that identification of a target in a complex mixture of miRNAs is plausible. These as well as other experiments demonstrated the feasibility of the concept presented in FIG. 1D. They also reveal that both the target and the probe can be either RNA or DNA, the difference being that probes are osmylated oligos, while targets are not. Further focus was on probes that are DNA oligos, because of the lower cost and the higher synthetic product quality compared to RNA oligos.

Alternative Methods to Test Hybridization Between a Target and its Probe

Independent means were sought to test hybridization between osmylated nucleic acids and their DNA or RNA targets. Enzymatic DNA polymerase elongation of an unmodified primer using partially osmylated template ssM13mp18 was the first attempt to obtain support for hybridization, but elongation of primers was not detectable (data not shown). Unmodified ssM13mp18 was then tested, as the template, and used 30 nt long, complementary T(OsBp) primers, BJ1, BJ2, BJ3, and BJ4 (see Table 1 and FIG. 11 and FIG. 13). BJ1 carries the identical sequence of primerM13for(−20) at the 3'-end, and is extended by 13 nt at the 5'-end. BJ2 carries the identical sequence of primerM13for(−41) at the 3'-end, and is extended by 6 nt at the 5'-end. BJ3 and BJ4 have the identical sequence to BJ2 with the exception of one mismatch in the middle of the sequence. Even though BJ2, BJ3, and BJ4 carried 6, 5, and 7 T(OsBp) bases, respectively (see Table 1), they were all successfully elongated (FIG. 3A), suggesting that T(OsBp) did not prohibit 1:1 hybridization between intact ssM13mp18 and the probes. In contrast, BJ1, with 6 T(OsBp) did not elongate, presumably due to the presence of a T(OsBp) base at the 3'-end and the inability of the enzyme to add a nucleotide to it (FIG. 3A). Still absence of elongation with BJ1 does not necessarily imply absence of hybridization.

These elongation experiments were done at salt concentration presumed to be much lower than the one used for the nanopore experiments, they were limited to ssM13mp18 and to the use of probes with sequences identical to known primers. To extend hybridization tests to miRNAs and any DNA/RNA oligo we developed an HPLC method as described elsewhere herein. This HPLC method is based on the HPLC method used to test for oligo purity with the following modifications: it uses (i) ONT buffer as the sample solvent and (ii) HPLC column temperature at 35° C. to mimic the ONT working flow cell temperature. It should be noted that the HPLC column packing may interfere with hybridization, and therefore all the HPLC-based results are purely suggestive. Having said that, there was no instance observed where the HPLC results and the nanopore experiment contradicted each other. To confirm hybridization HPLC analyses of three separate samples are required. These three samples contain (i) the probe, (ii) the nucleic acid target molecule, and (iii) the sample with the 1:1 mixture of the two components that contains the presumed hybrid (see FIGS. 3B-3D). Absence of hybridization is consistent with an HPLC profile of the mixture sample that closely overlaps with the "sum" of the HPLC profiles of the two components (FIG. 3C). Evidence for hybridization is consistent with a hybrid peak that elutes well resolved from the peaks of the target and of the probe and typically 1 to 1.5 minutes later than either probe or target. In addition, the probe and hybrid peaks exhibit absorbance at 312 nm, due to the presence of the OsBp tag, but the target peak does not. 1:1 mixture samples were prepared intentionally with a small excess of the target to prevent the probe from being in excess. This is why in many of the HPLC chromatograms the analysis of the hybrid sample includes a smaller peak attributed to the target, in addition to the large peak attributed to the hybrid.

Figure 3B:
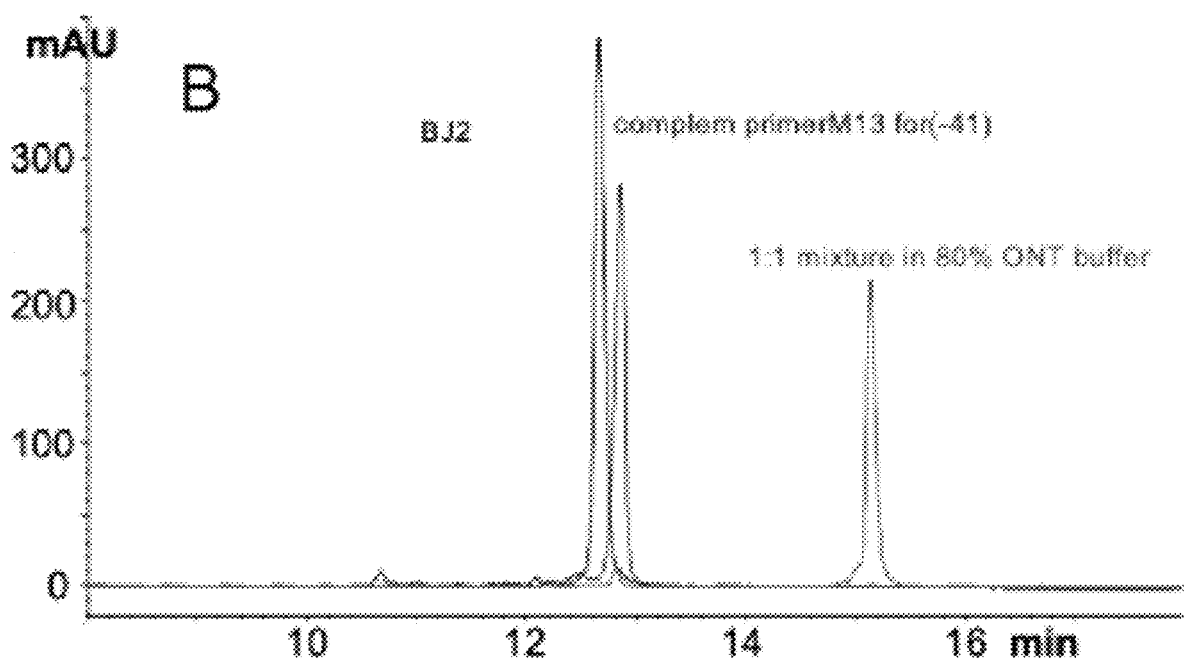
Figure 3C:
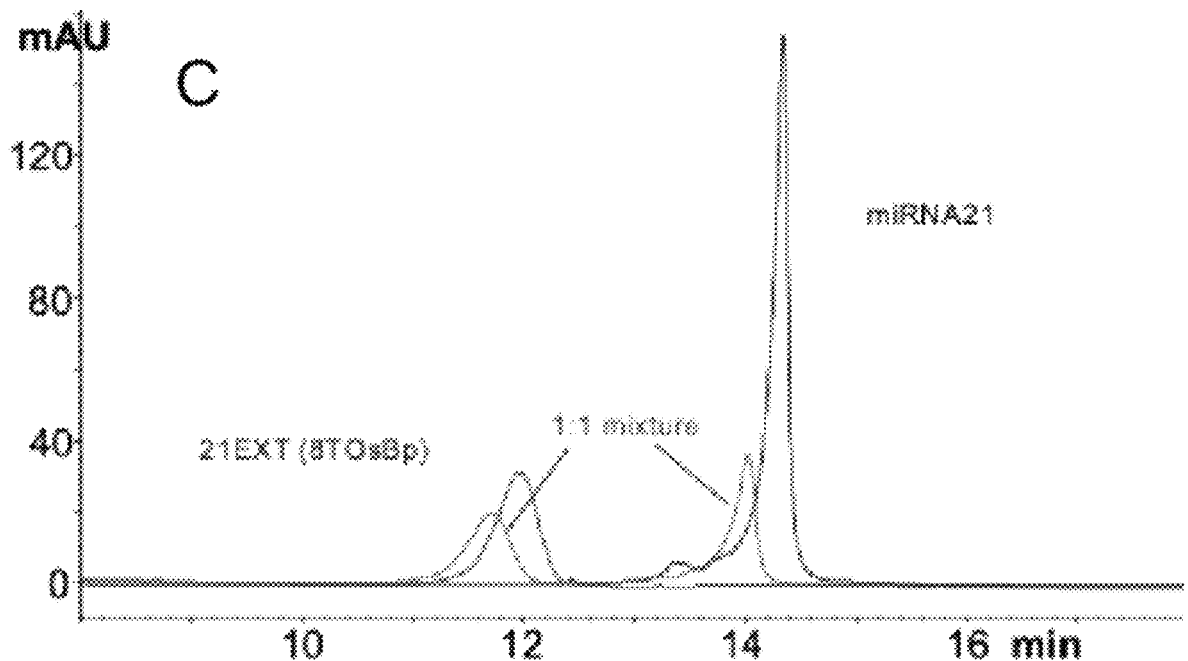
Figure 3D:
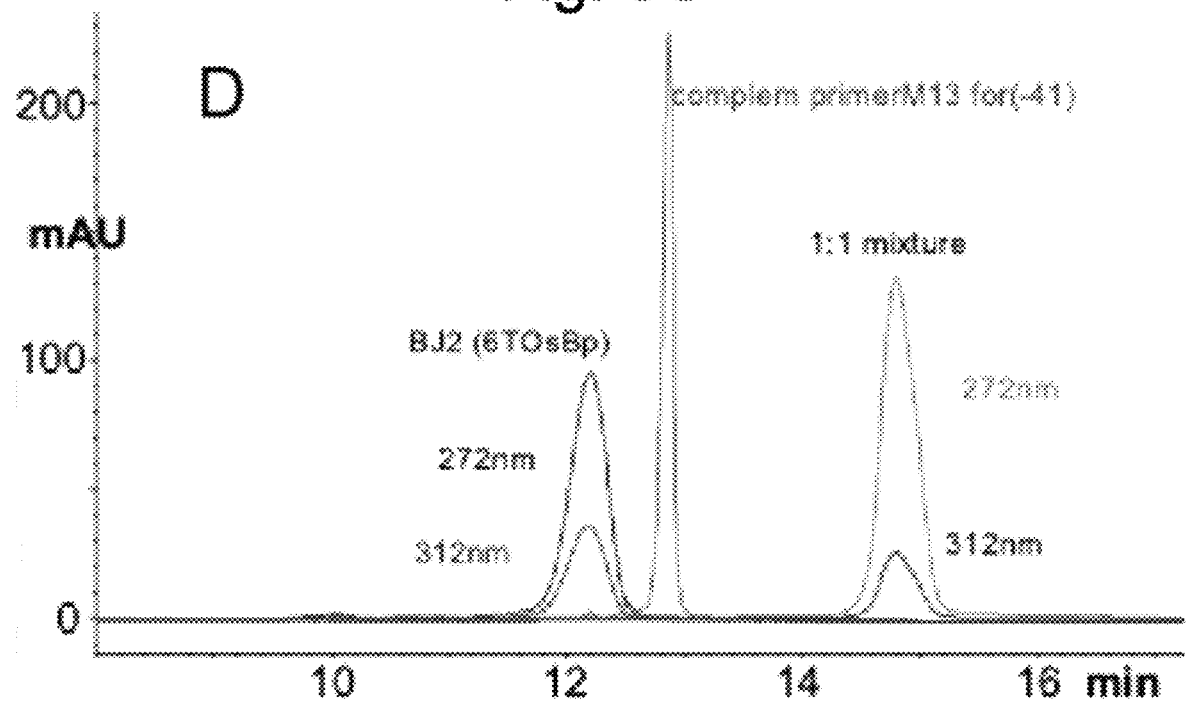

FIG. 3B shows the HPLC chromatograms of samples where both oligos are unmodified nucleic acids. Here the HPLC profile of the sample with the 1:1 mixture is consistent with strong hybridization, based on the features discussed above. FIG. 3D is a repeat of the HPLC analyses in FIG. 3B, only that BJ2 is now osmylated; it is a probe. The corresponding HPLC profile of the 1:1 mixture in FIG. 3D is also consistent with strong hybridization. The same HPLC method indicated that miRNA21 and probe 21EXT (see Table 1) do not hybridize (FIG. 3C). The absence of hybridization in FIG. 3C is attributed to the relatively large number of OsBp moieties present within the probe's sequence (total 8 dTs, with 5 dTs found within the 21 nt sequence). Additional hybridization tests confirmed the hypothesis that ds complex formation is prohibited in the presence of a large number of OsBp moieties on the probe (see FIG. 10). Besides the number of OsBp moieties in a molecule, the actual location matters as well. As seen with the BJ1-4 probes, hybridization remains strong, despite a relatively large number of T(OsBp). This is most likely because these tags occupy a small area of the sequence, leaving two rather long subsequences available for duplex formation with the target.

Hybridization Silences the Probe in the Presence of the DNA Oligo Target

Experiments in FIG. 2 were conducted using probe, target, and hybrid concentration in the 5 μM range. Since sample size of a MinION and that of a Flongle flow cell is 75 μL vs. 30 μL, the 5 μM concentration corresponds to approximately a 0.38 vs. a 0.15 nmole sample load, respectively. It is worth mentioning that sample load for a nanopore experiment is not the same as sample load for an HPLC analysis, as the HPLC injection volume is typically not the same as the flow cell sample size. FIG. 4A illustrates the HPLC hybridization test, described above, using probe BJ1 with 5 T(OsBp) and its target, complementary primer M13for(−20). The samples of probe and hybrid were used, as is, for the nanopore experiments, shown in FIG. 4B. We note that probe BJ1 was not enzymatically elongated using ssM13mp18, as the template, which we attributed to the presence of a T(OsBp) base at the 3'-end. In FIG. 4 hybridization is documented both by HPLC analysis and by nanopore experiments, as shown by the huge drop in the number of counts reported for the hybrid sample compared to the counts reported with the probe sample. The effect is dramatic for the $(I_r/I_o)_{max}$, and clearly detectable for the rest of the $I_r/I_o$ range.

Applied Voltage is a Critical Parameter

Figure 4B:
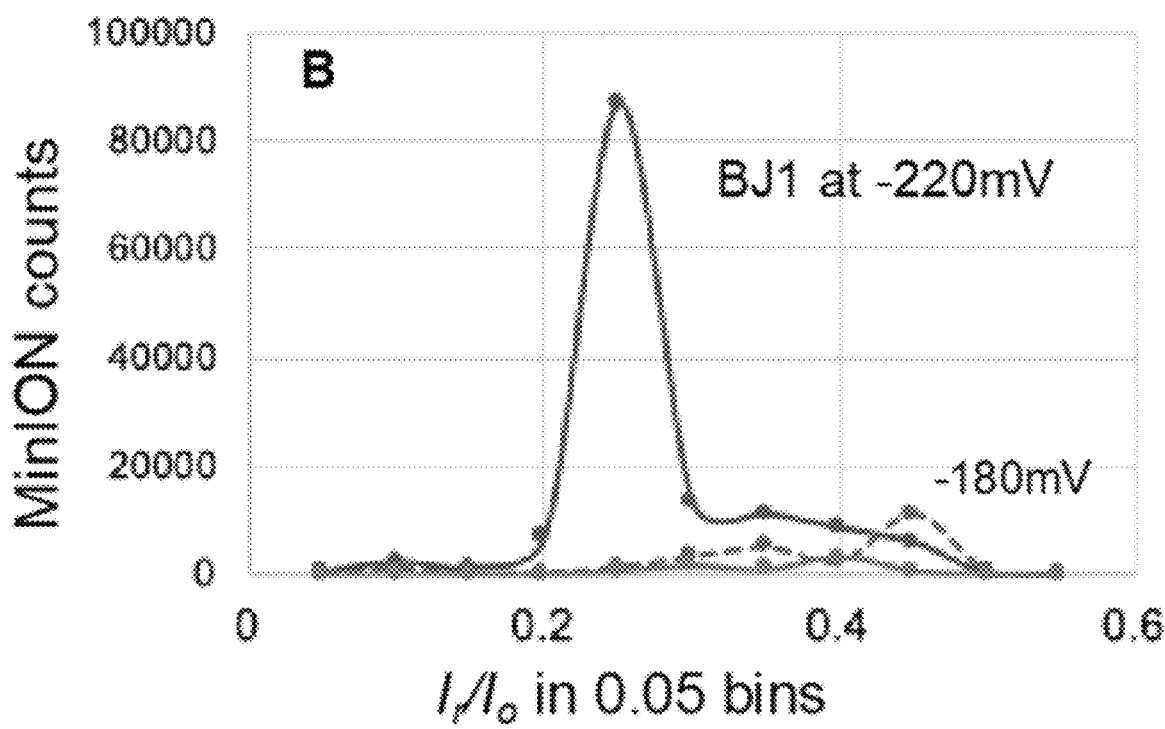

FIG. 4B illustrates that testing probe BJ1 with applied voltage at −180 mV exhibits very low counts suggesting that probe translocation is inefficient at −180 mV. Without addition of a new sample, raising the voltage to −220 mV yielded dramatically more counts compared to the counts obtained at −180 mV. FIG. 11 illustrates that probes BJ2 and BJ4 follow the same pattern as BJ1. This observation was attributed to the presence of adjacent dT(OsBp) in the probes, and the notion that dT(OsBp) exhibits the lowest observed $(I_r/I_o)_{max}$, among all tested pyrimidines, a strong indication of heavy crowding. Heavy crowding in adjacent OsBp moieties was concluded from earlier studies using RNAs and the MinION/CsGg (Sultan M., Kanavarioti, A. (2019)), as well as DNAs and the a-Hemolysin nanopores (Ding, Y. & Kanavarioti, A (2016)). Since the probes are deoxyoligos and include several T bases in the sequence, the steric hindrance is compounded. Labeled nucleic acids may approach the CsGg pore guided by the applied voltage drop, but to traverse the pore a certain minimum voltage is required. Multiple experiments suggested that the applied voltage for efficient translocation of most of our probes via the proprietary CsGg nanopore is in the range of −210±10 mV. In contrast to the observations with the probes, intact DNA oligos exhibit insignificant counts (Ding, Y. & Kanavarioti, A. (2016); Sultan M., Kanavarioti, A. (2019)) and target/unmodified miRNAs exhibit measurable counts with a slight decreasing trend as a function of increasing voltage (FIG. 13). This is consistent with the expectation that increased voltage results in faster translocation and faster translocation, in turn, results in missed events, as the acquisition rate of the device remains constant at 3 data points per ms. In order to make the counts with native RNAs detectable the total load was 4-times higher than the highest probe load. Experiments with voltage higher than −220 mV were not conducted, in order to protect the protein pores that, in our experience, did not last as long at −220 mV compared to −180 mV. The observation that our probes practically do not traverse the CsGg pore at −180 mV is an advantage for a diagnostic test. It provides the opportunity to deplete the sample from excess non-target nucleic acids at −180 mV, and then, without adding any a new sample, raise the voltage at −220 mV in order to detect, or not, the presence of the uncomplexed probe.

General Design for a Highly Detectable Probe

The presence of T(OsBp) moieties in the middle of a sequence is not a feature shared by many potential ctDNA or miRNA targets. Therefore, advanced probes were designed by replacing all dTs in the sequence with dU, modifying some or all the bases as 2'-OMe, added 3 adjacent dT(OsBp) at the 5'-end, and, in some cases adding 3 additional dAs at the 3'-end. Addition of dAs at the 3'-end is commonly used to facilitate pore entry (Kasianowicz, J. J., Brandin, E., Branton, D. & Deamer, D. W. (1996); Butler, T. Z., Gundlach, J. H. & Troll, M. (2007); Maglia, G., Heron, A. J., Stoddart, D., Japrung, D. & Bayley, H. (2010)). Replacing DNA bases with 2'-OMe bases has been reported to lead to stronger hybridization (Majlessi, M., Nelson N. C. & Becker, M. M. (1998)). Replacing all dTs with dUs assures that the presence of OsBp is minimal within the sequence. This results in the lowest possible number of OsBp moieties within the sequence and the most unhindered hybridization with the target. The addition of 3 adjacent dTs at the 5'-end makes the probe undetectable at applied voltage of −180 mV and highly detectable at applied voltage of −220 mV, as shown by the earlier experiments with the BJ1-4 probes. This probe design was then exploited in nanopore experiments with extra low target loads.

Figure 4C:
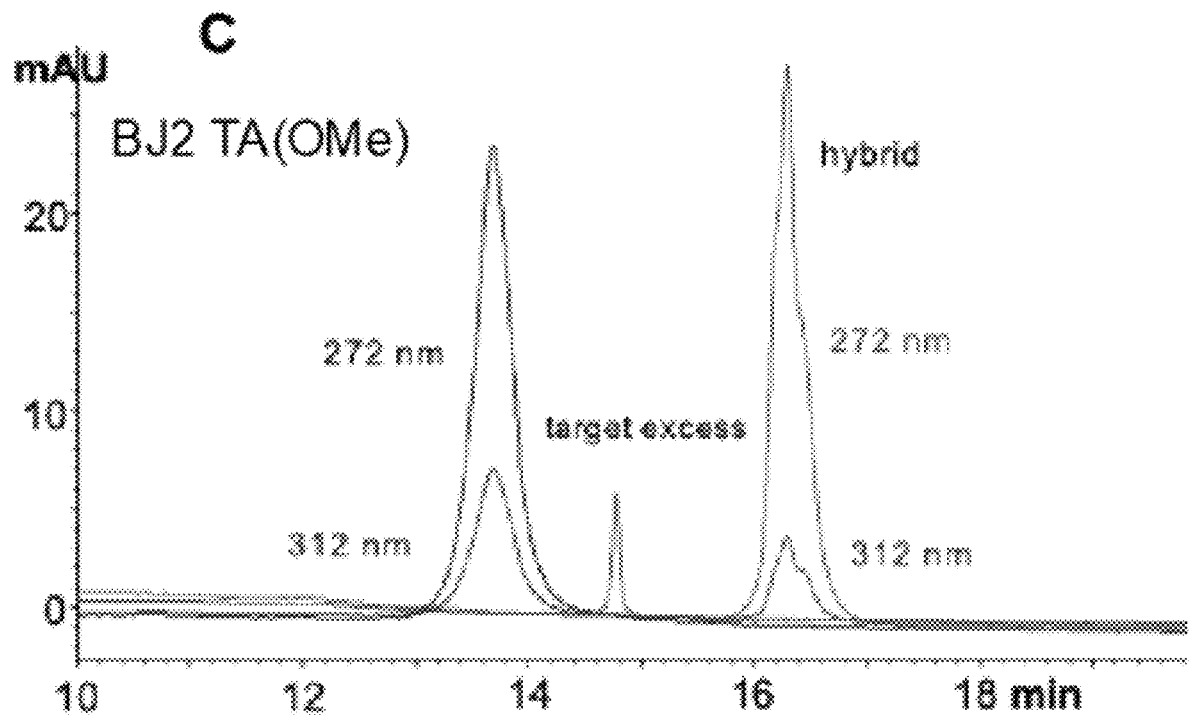
Figure 4D:
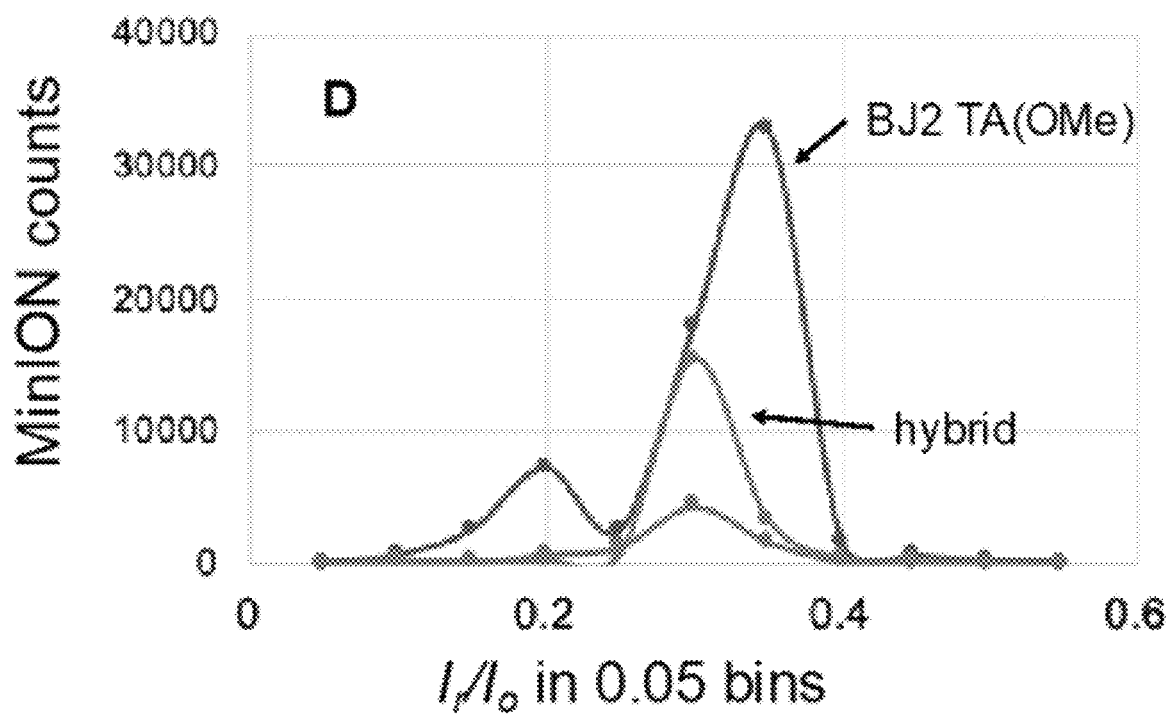

BJ2 TA(OMe) is a probe designed with the above features (sequence in Table 1). Hybridization between probe BJ2 TA(OMe) and the complementary primerM13for(−41) was tested by HPLC at the 5 μM concentration range (FIG. 4C). FIG. 4C presents the HPLC analyses of the probe and of the hybrid samples. The target peak in the hybrid sample is easily identified due to its about 10% excess over the probe. The HPLC profiles at both wavelengths, 272 nm and 312 nm, are shown. Close inspection of these profiles illustrates that the hybrid peak has about half the contribution at 312 nm, compared to the corresponding contribution in the probe. This is in agreement with the expectation that the hybrid is half probe and half unmodified target. The actual samples tested by HPLC were diluted with ONT buffer to produce the samples tested by nanopore. The protocol followed for this and all dilutions in this study was done by consecutive 1:10 dilutions with ONT buffer in 0.5 mL microcentrifuge tubes. The nanopore experiment with probe BJ2 TA(OMe) was done at a 1000-fold dilution compared to the HPLC sample. i.e., at a 0.38 pmole probe load. The corresponding experiment with the hybrid was conducted at 3.75 pmole, i.e., at a 10-times higher hybrid load. The high hybrid load was chosen to test the stability of the hybrid under the experimental parameters especially under the influence of the −220 mV applied voltage. Despite the hybrid sample being 10-times more concentrated than the probe, the counts obtained from the hybrid experiment were visibly fewer compared to the counts obtained from the probe experiment and suggest that hybrid dissociation is not significant under the tested conditions (FIG. 4D).

Figure 5A:
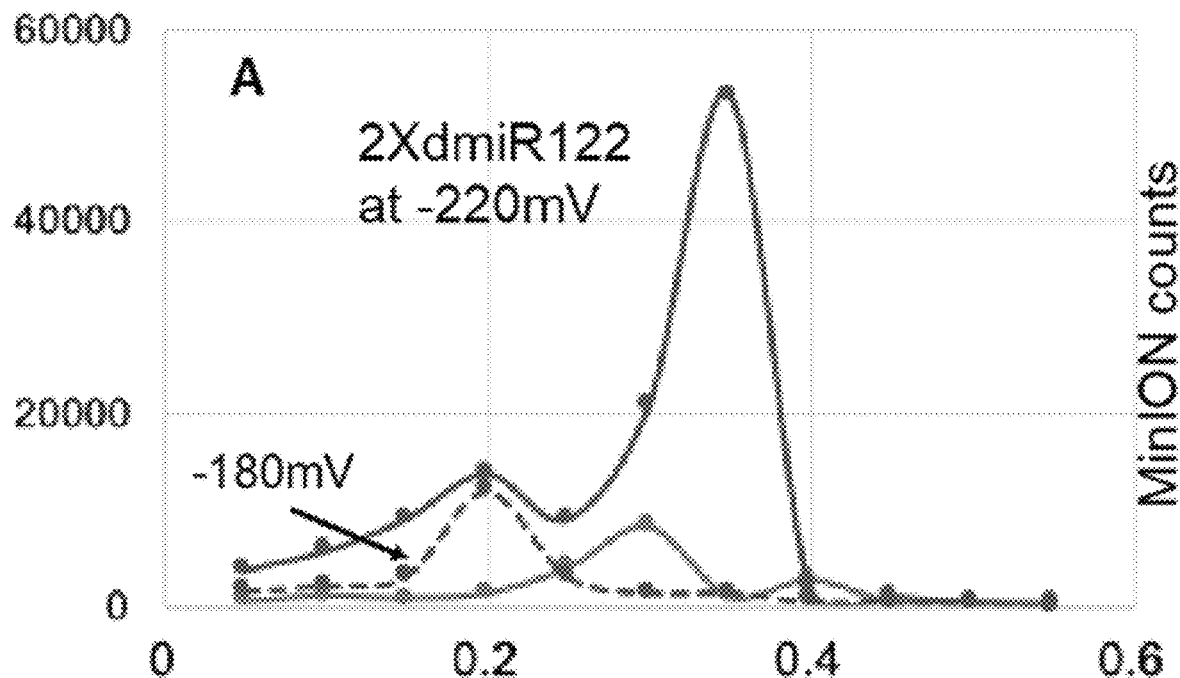

Hybridization silences the probe in the presence of an RNA oligo target. During the development work several probe designs were explored. Experiments with two of those designs are illustrated in FIG. 5. Probe 2XdmiR122 is a 44 nt oligo with 8T(OsBp) and consists of two fused dmiR122 (sequence in Table 1). Even though probe dmiR122 exhibited numerous counts at −190 mV (FIG. 2B), probe 2XdmiR122 required −220 mV (FIG. 5A). The higher voltage is most likely the consequence of heavy crowding within the pore, as 2XdmiR122 incorporates two 4 nt groups with 3 OsBp each within a subsequence of 26 nt. Efficient hybridization between miRNA122 and 2XdmiR122 was shown by HPLC (FIG. 5C) and confirmed by nanopore, as seen by the huge drop of counts for the hybrid sample compared to the probe sample (FIG. SD). The advantage of such fused sequence design lies in exploiting cases where the identical sequence of bases is present in a longer RNA in addition to a miRNA target. Using a probe with a design like the fused 2XdmiR122 may favor hybridization with the miRNA target over the long RNA target, as 2XdmiR122 can form a 44 nt ds complex with miRNA122, but only a 22 nt ds complex with the longer RNA.

Figure 5B:
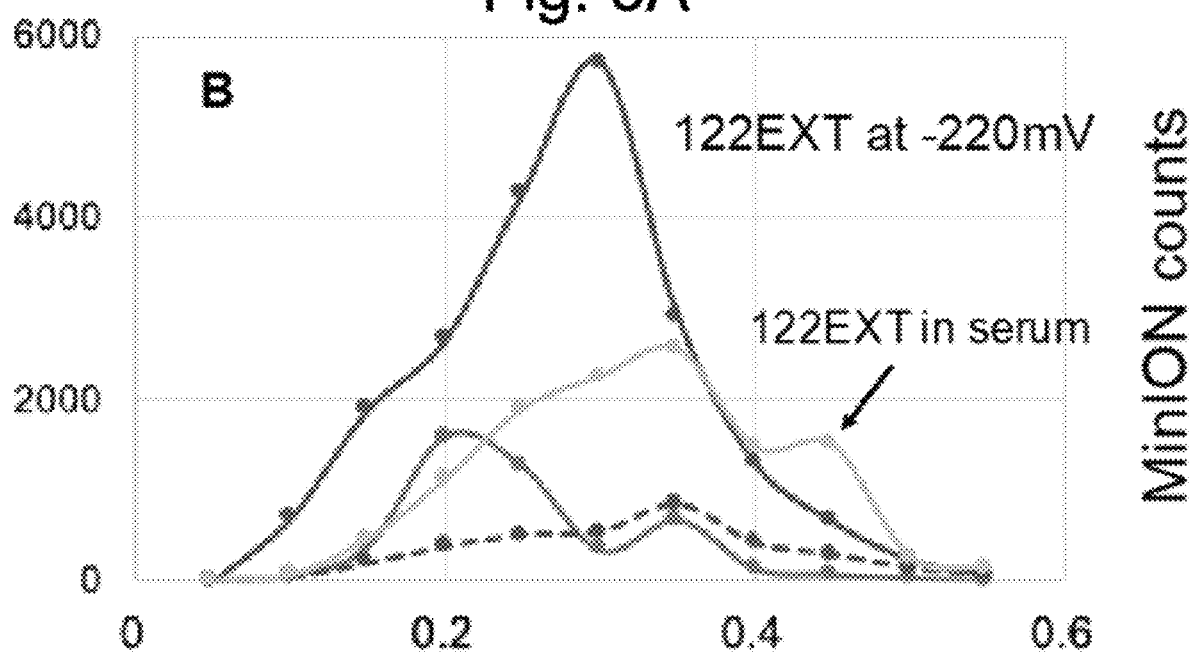
Figure 5C:
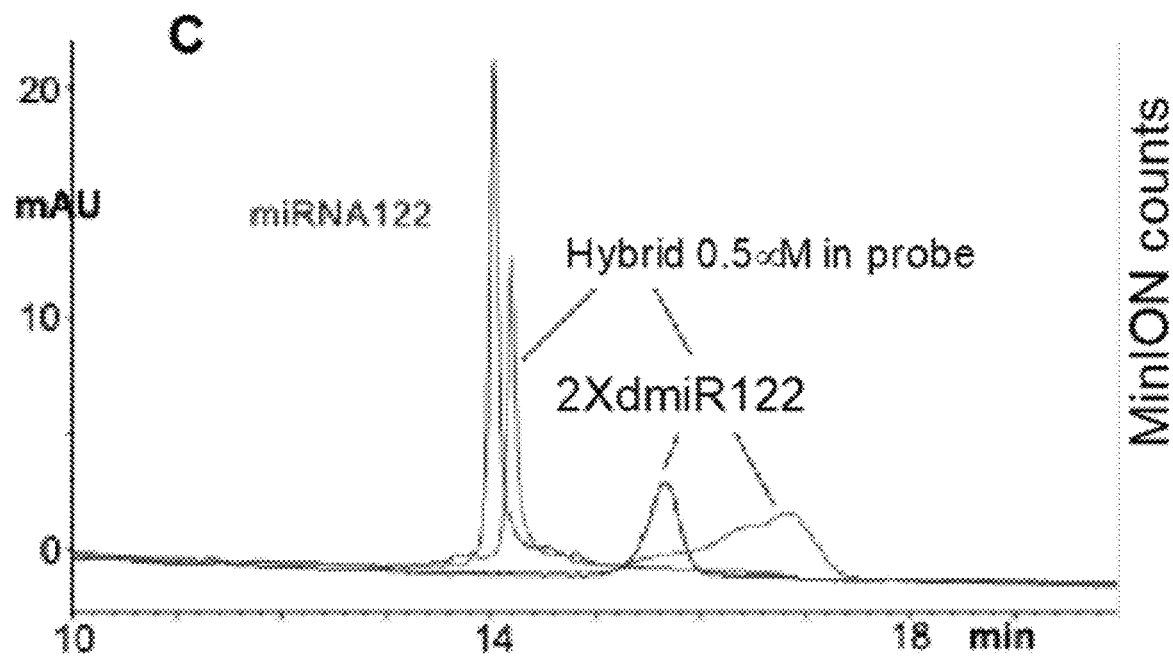
Figure 5D:
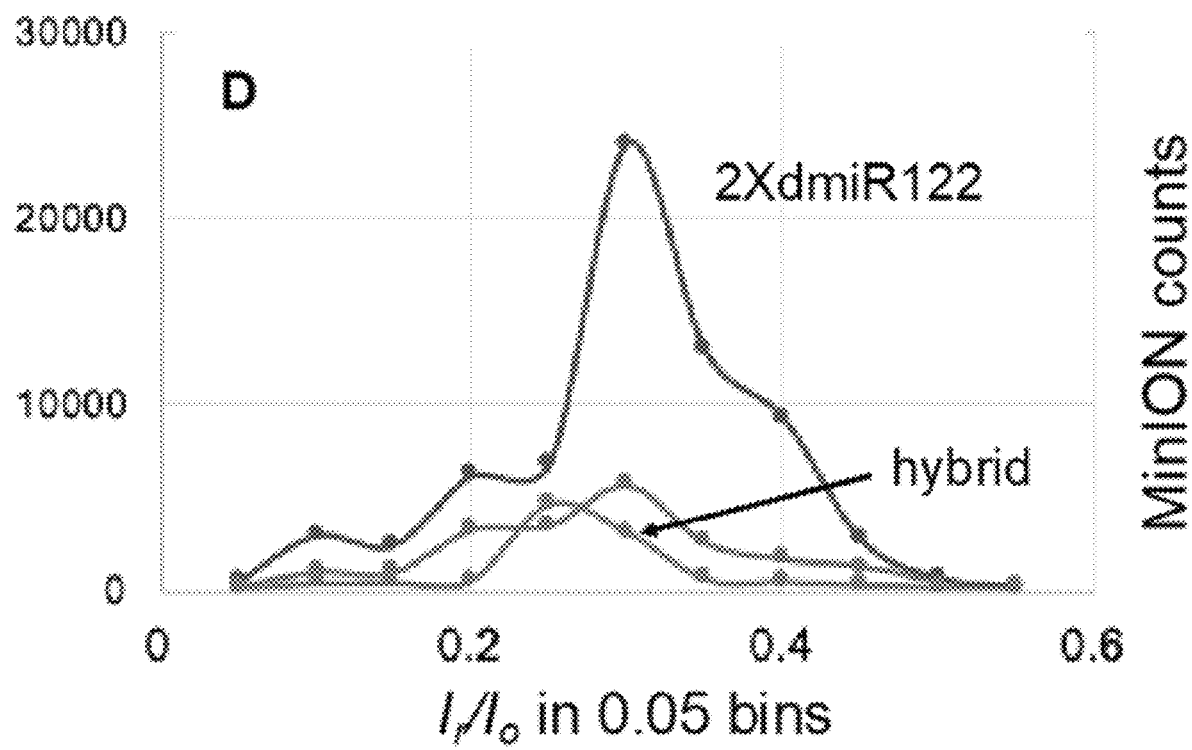
Figure 12B:
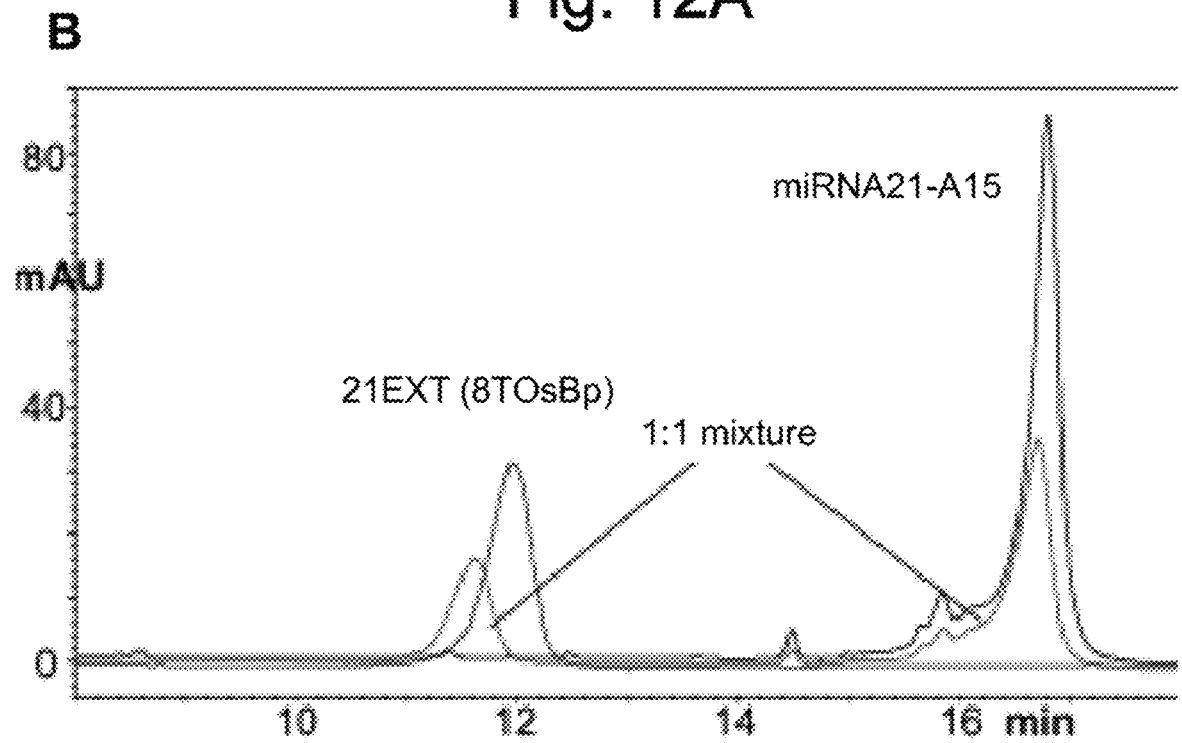

FIG. 5B shows another probe design, exemplified by probe 122EXT (sequence in Table 1). Probe 122EXT has the identical sequence of dmiR122 with the addition of 3 adjacent Ts at the 5'-end. This probe requires −220 mV to show numerous counts (solid trace), as seen by comparison to the nanopore experiment at −180 mV (dashed trace). A nanopore experiment conducted with probe 122EXT in a sample prepared in 15% human serum and 85% ONT buffer exhibits reduced counts compared to the sample prepared in over 95% ONT buffer. The reduction in counts may be attributed to the lower ionic strength due to the presence of serum, and/or to the aged flow cell and/or to serum interference. Despite the lower counts probe 122EXT is easily discriminated from the control/buffer test indicating the unhindered probe detection in an unknown sample that contains a body fluid, such as human serum.

miRNA21 is an important biomarker for a number of diseases (Thum, T. et al. (2008); Kao. H. et al. (2017); Fulci, V. et al. (2007)), so its identification was tested. HPLC tests with miRNA21 and probes dmiR21 (not shown) or 21EXT indicated no detectable hybridization with miRNA21 (FIG. 12A, FIG. 12B). Inability to form the hybrid was attributed to the presence of more than 6 T(OsBp) moieties and the fact that these moieties are spread over the 22 nt sequence. Advanced probe design led to probes that efficiently hybridized with miRNA21. Probe dmiR21(OMe) is a 22 nt oligo, complementary to miRNA21, where all bases are 2'-OMe, Ts are replaced with di, and osmylation resulted in the addition of 2.85 OsBp moieties, on average, per molecule (osmylation protocol d, see Table 1). The osmylated product is a mixture containing primarily molecules with 2 or 3 OsBp moieties, and also molecules containing OsBp moieties at different bases (called here topoisomers) (Sultan M., Kanavarioti, A. (2019); Kanavarioti, A. et al. (2012)). Chromatography resolved molecules that carry one, two or three OsBp moieties and often resolves topoisomers too (Kanavarioti, A. (2016). This is why the HPLC profile of the probe consists of two separate peaks attributed to molecules with 2 tags and to molecules with 3 tags (FIG. 6A). Similarly, the HPLC profile of the hybrid appears as multiple peaks (FIG. 6A). HPLC was also used to test the stability of RNAs (see below) and the stability of the hybrid of dmiR21(OMe) with miRNA21 in a sample solvent that contains 15% human serum and 85% ONT buffer. FIG. 26B illustrates that the tested RNAs, i.e., miRNA140 and the 100 nt RNA, both degraded within minutes, whereas the hybrid peak remained practically unchanged, suggesting that the hybrids formed between our probes and their RNA targets are expected to be stable during the duration of an experiment in human serum.

Hybridization is consistent with the distinct HPLC profiles observed with the probe and the hybrid samples (FIG. 6A). Because dmiR21(OMe) does not contain 3 adjacent T(OsBp), applied voltage at −180 mV was sufficient to thread this probe via the pore. Plenty of events were reported with a 0.75 nmole probe sample and markedly fewer with a 1.5 nmole hybrid sample (FIG. 6B, compare solid trace with dashed trace). Counts with the hybrid appear comparable to counts obtained with buffer (not shown). Additional nanopore experiment were conducted with identical probe and hybrid loads but in the presence of other RNA components. These components were a non-target nucleic acid, miRNA140, and a 100 nt RNA, at a total 10-fold higher load compared to the probe. The nanopore profiles of the probe samples with or without the excess non-target RNA are distinct suggesting influence by the excess material and/or an aged flow cell. Still the two experiments in the presence of the non-target RNA show efficient identification of the target by comparing the numerous counts of the probe sample to the few counts of the hybrid sample (second dashed line, almost indistinguishable from the first dashed line (hybrids)). This discrimination suggests that the presence of non-target miRNAs and longer RNAs in a complex mixture do not prevent target identification.

Figure 7A:
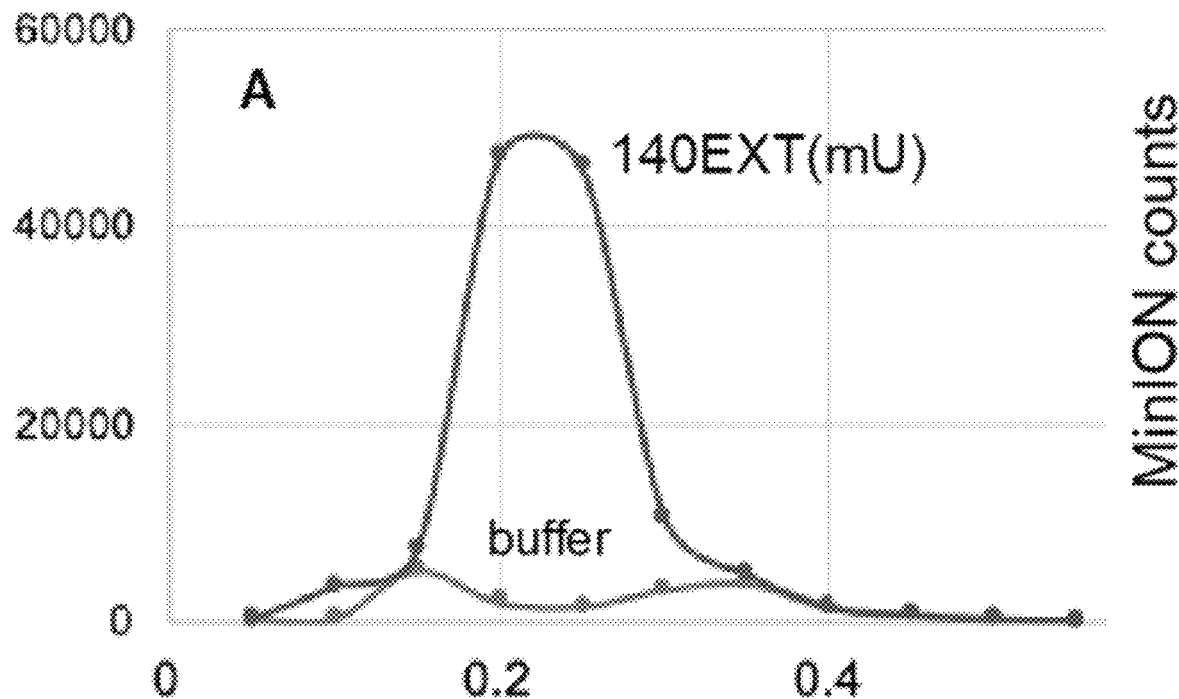
Figure 7B:
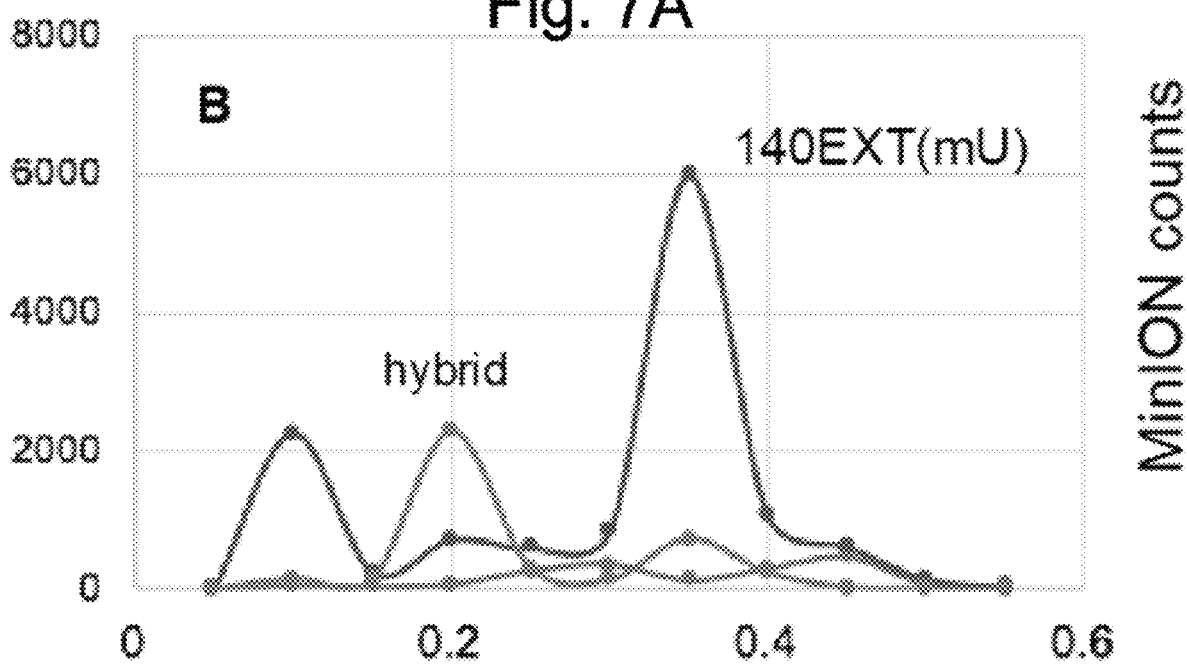
Figure 7C:
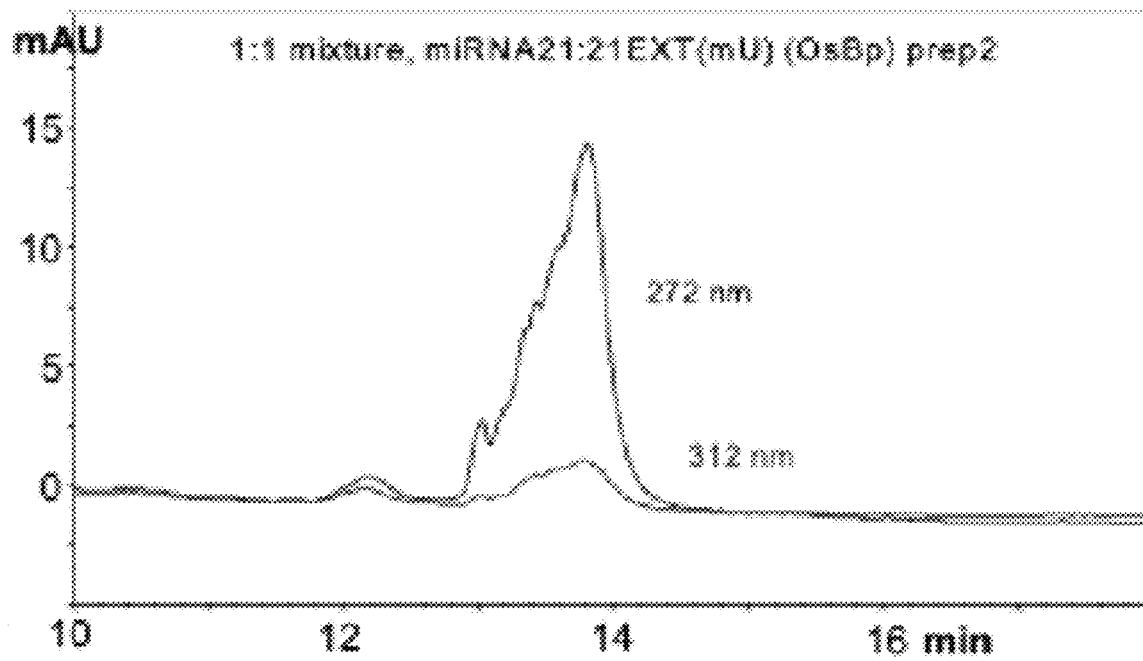
Figure 7D:
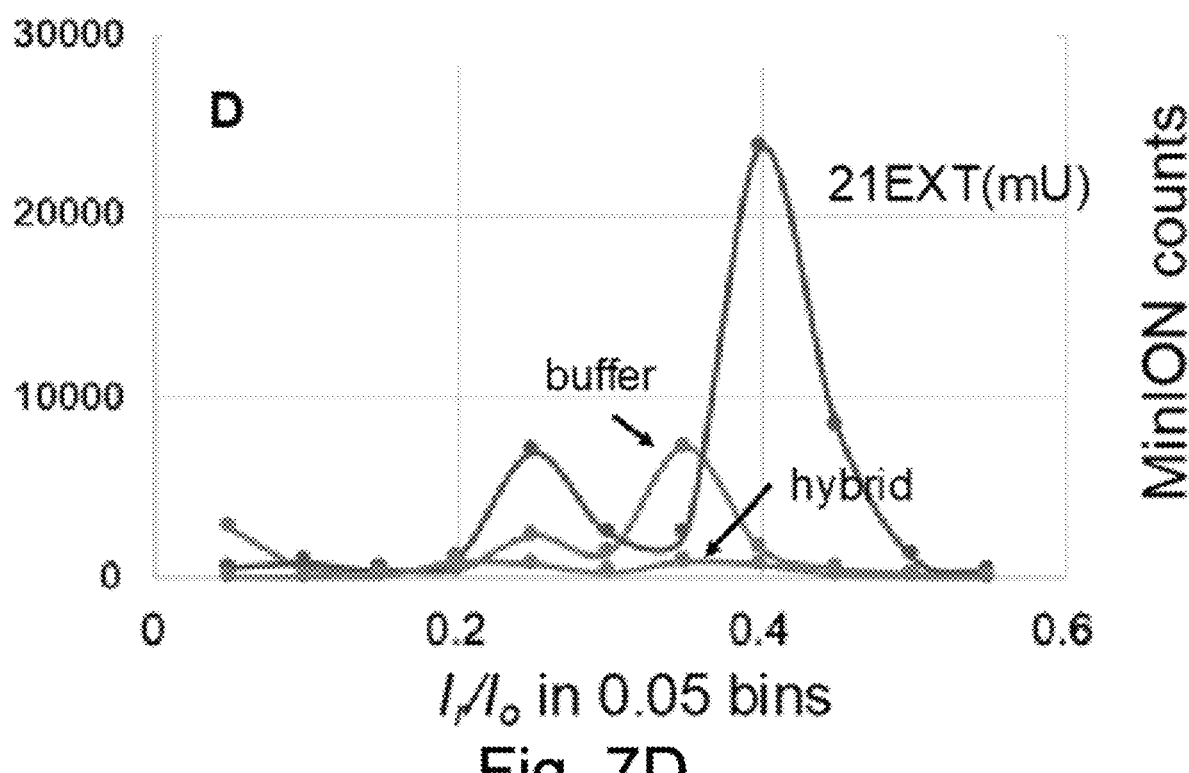
Figure 9A:
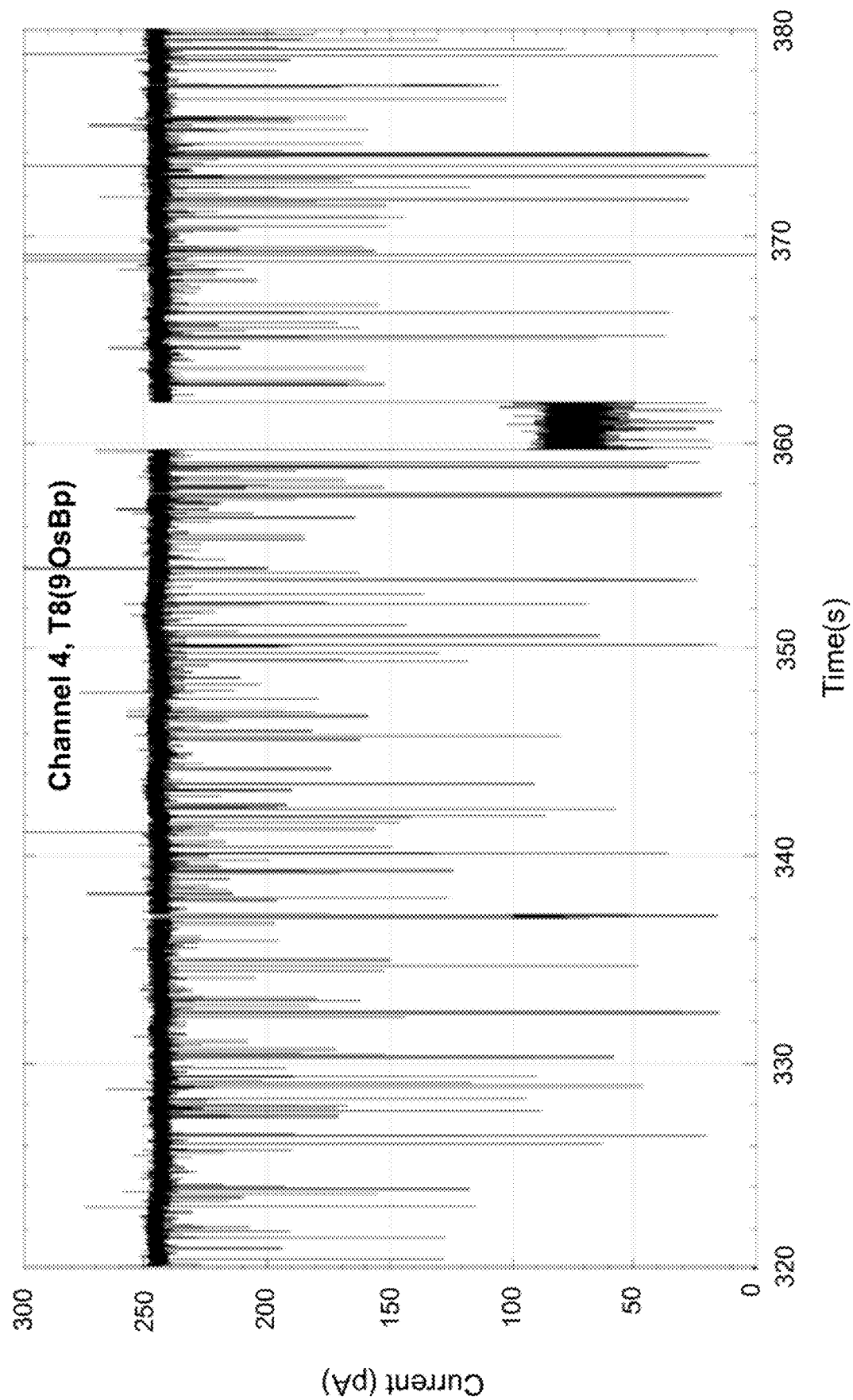
Figure 9B:
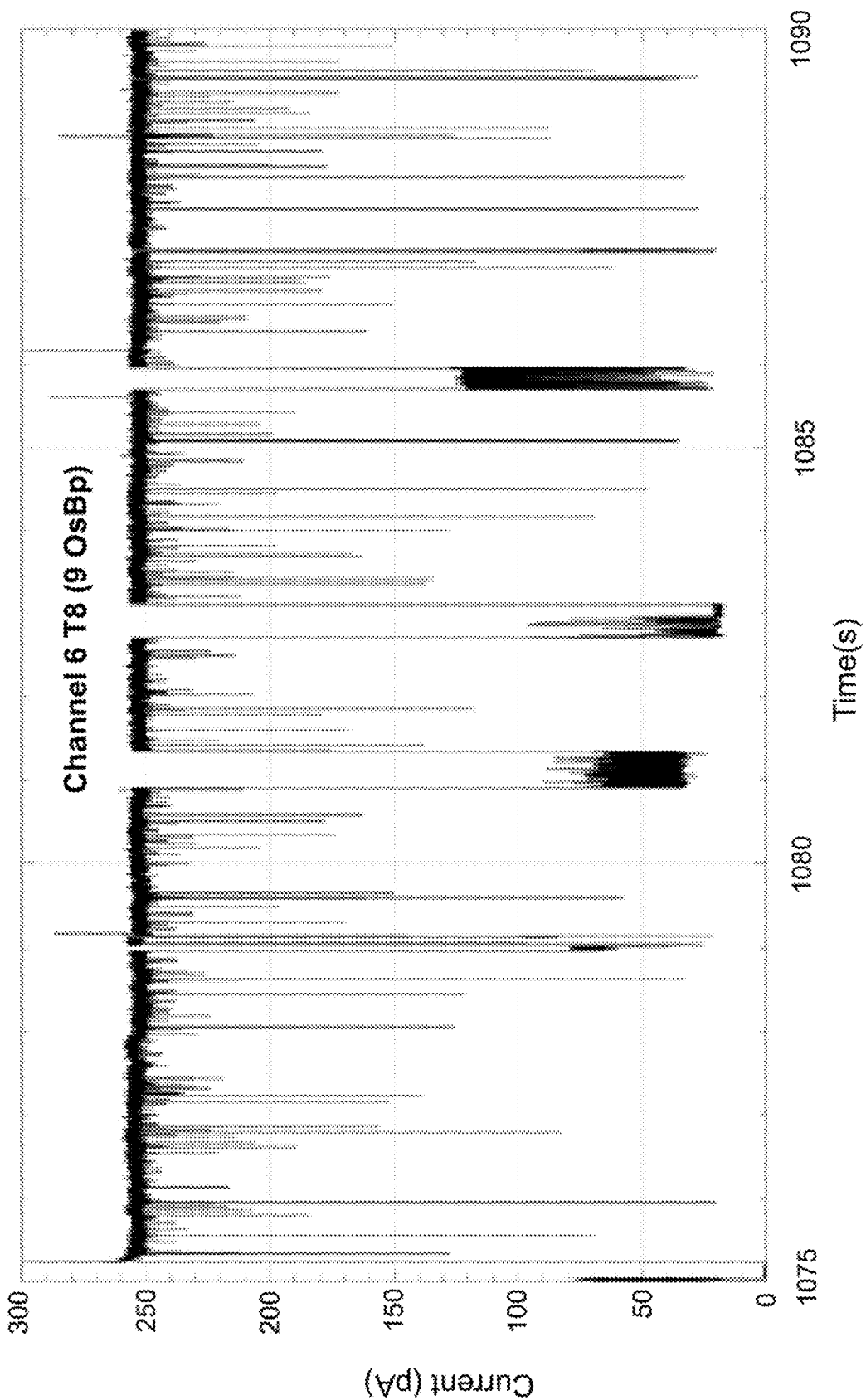
Figure 9C:
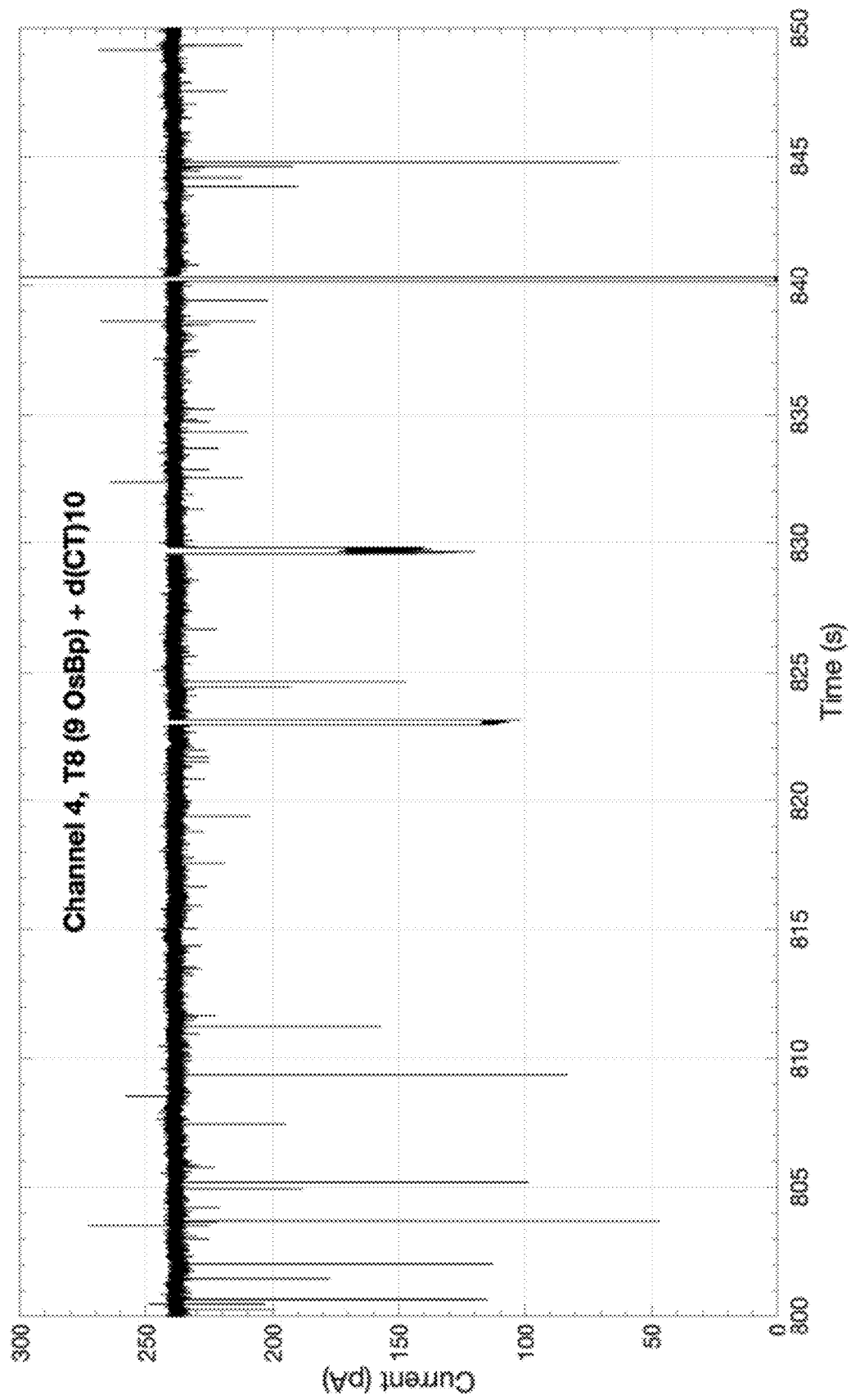
Figure 9D:
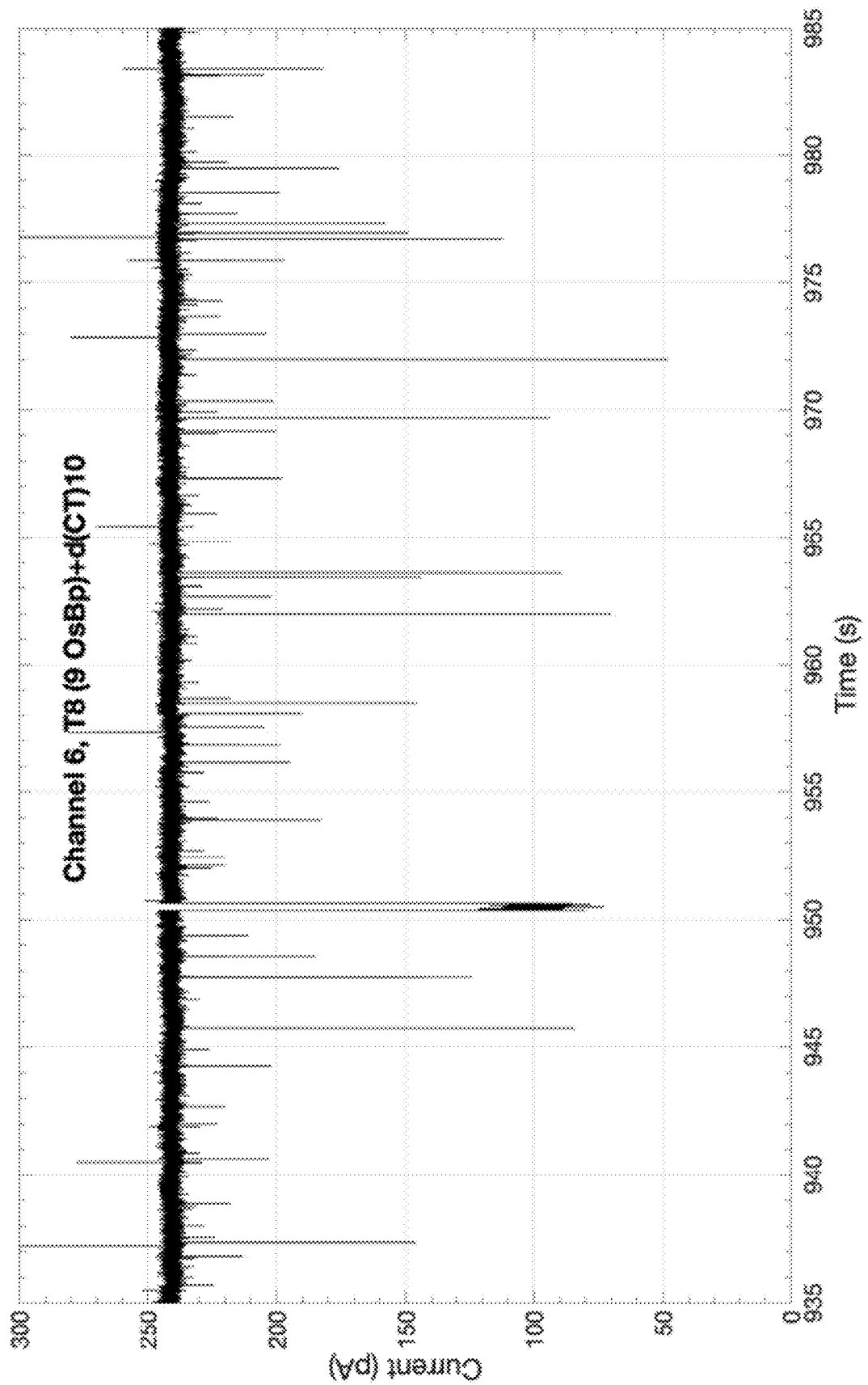
Figure 10A:
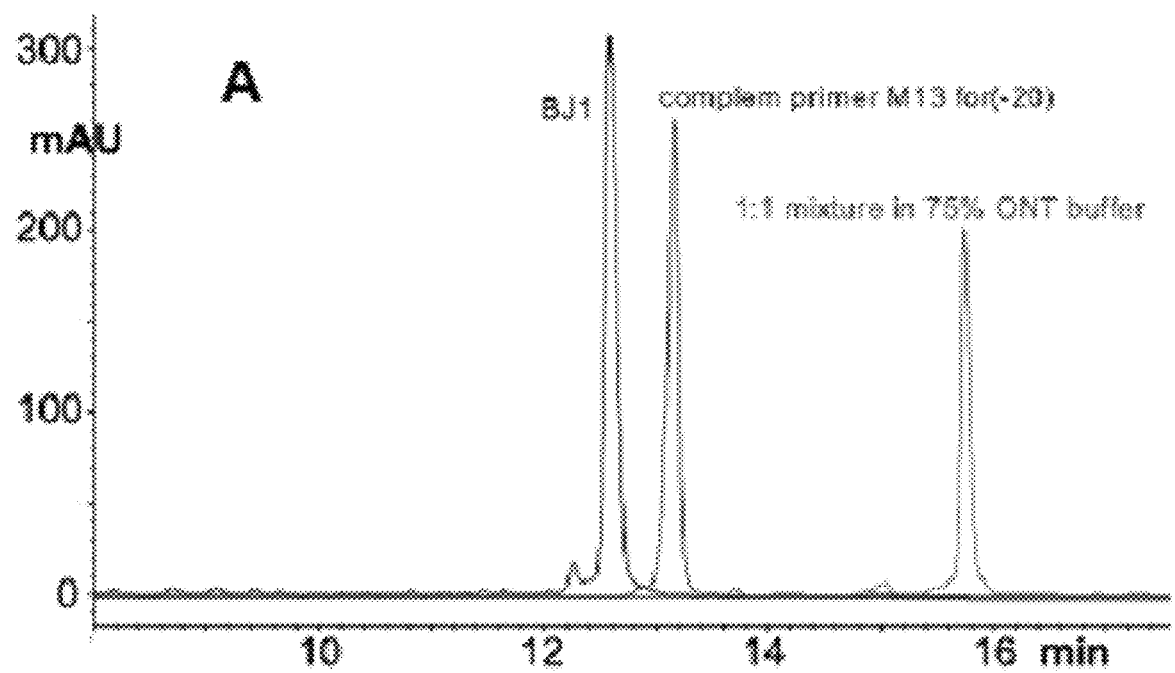
Figure 10B:
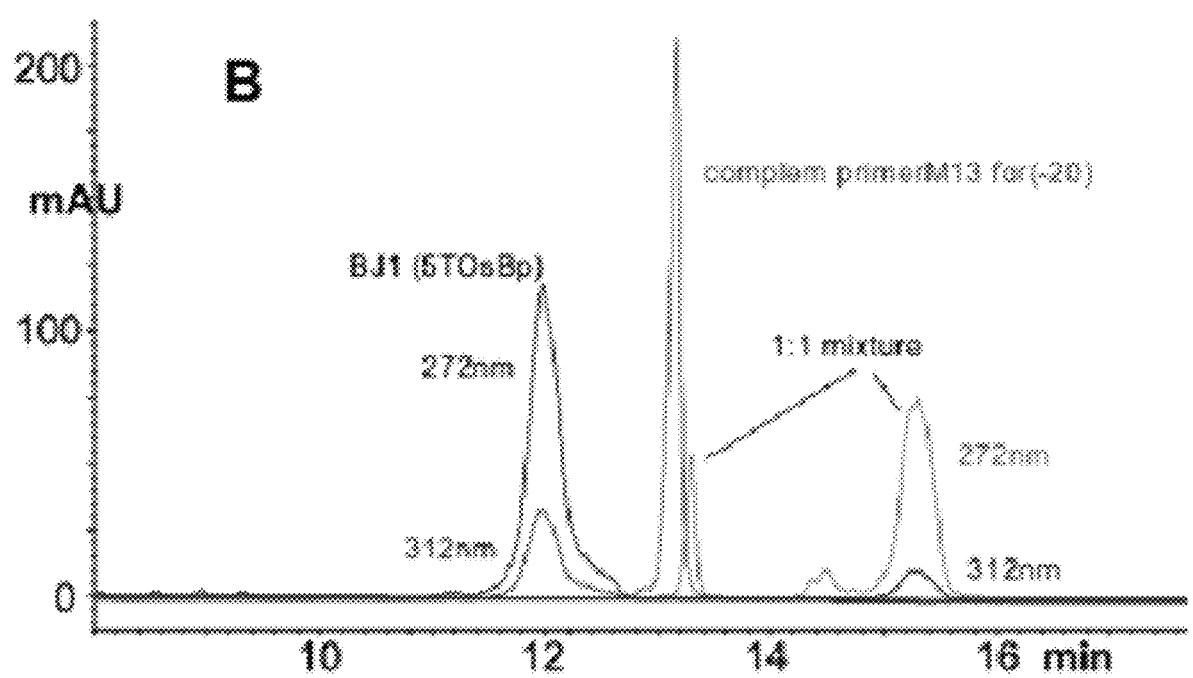
Figure 10C:
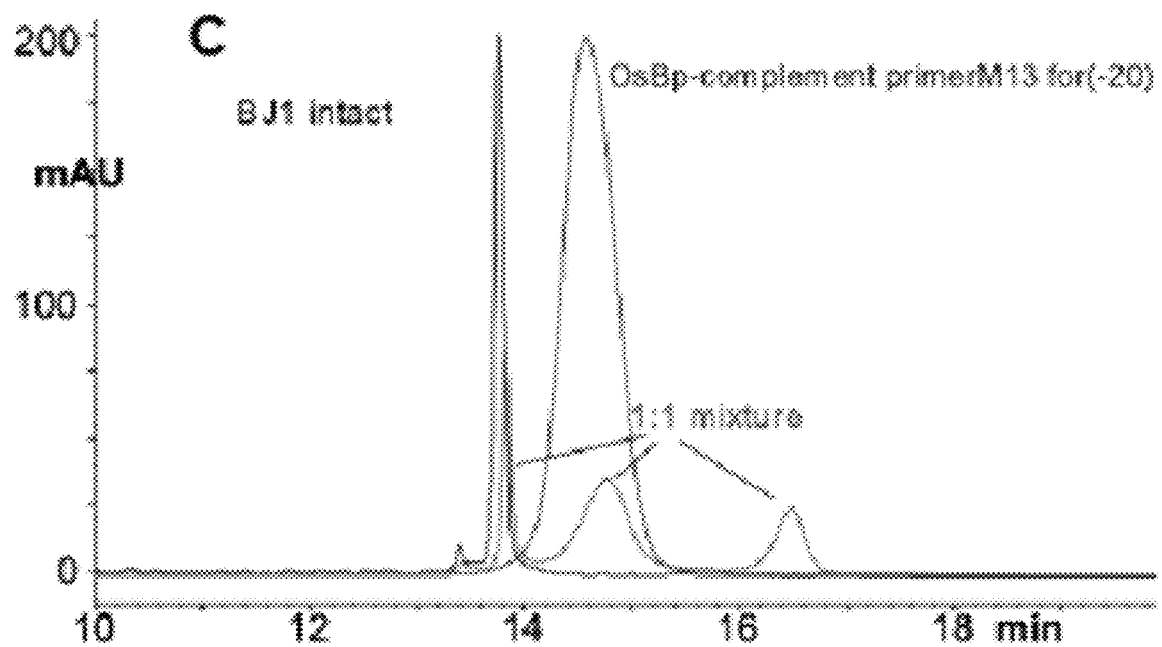
Figure 10D:
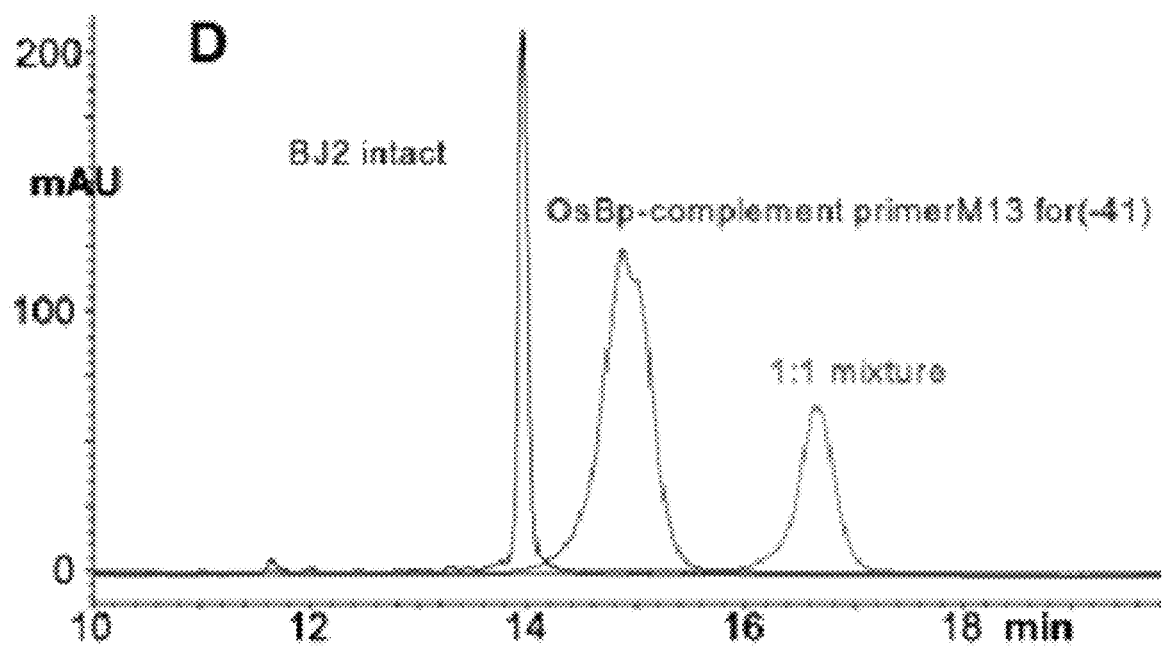

Due to the importance of miRNAs as biomarkers (Li, X-D. et al. (2017); Thum, T. et al. (2008); Lai, J. Y. et al. (2015); Kao, H. et al. (2017); Fulci, V. et al. (2007); Wang, Y. et al. (2020)), experiments were conducted at extra low load with a probe design that is broadly applicable to any target sequence and has optimal translocation properties. Probes 140EXTmU and 21EXTmU to target miRNA140 and miRNA21, respectively, were selected. These probes have a sequence complementary to their target, mU replacing T within the sequence, 3 additional adjacent dTs at the 5'-end, and 2 or 3 additional dAs at the 3'-end. These oligos were osmylated using the validated labeling process that adds, on average, 4 to 5 OsBp tags per molecule, 3 of which occupy the 5'-end, and the other 1 or 2 are randomly allocated within the sequence (see Table 1). Due to the heavy crowding at the one end of the probe, applied voltage in the range of −210±10 mV is required for probe efficient translocation and detection (per discussion above). FIG. 7A illustrates detection with excellent sensitivity at the 47 fmole level with 140EXT(mU), and FIG. 7B illustrates detection of this probe at an even higher sensitivity of 3.5 amole probe load. Identification of the target miRNA140 is also evident by comparing the probe to the hybrid with hybrid load also at 3.5 amole. FIG. 7C shows the HPLC profile of the hybrid sample between probe 21EXT(mU) and miRNA21, which was then diluted by a $3 \times 10^8$ factor for the nanopore experiment to test the hybrid at the 2.7 amole level (FIG. 7D). The 21EXT(mU) probe sample (HPLC profile not shown) was diluted by a $1 \times 10^9$ factor in order to conduct the nanopore experiment at the 0.9 amole level of (FIG. 7D) which is the lowest load tested in this study. Identification of miRNA21 is evident in FIG. 7D by visual comparison of the probe counts to the counts of the hybrid. The reason that the counts observed with the 140EXT(mU) probe (top, reaching 6,000) are fewer compared to the counts observed with the 21EXT (mU) probe (bottom, reaching 24,000) is, at least partially, due to an aged flow cell that had only about 30% of working pores. Whether or not proportionality in probe counts can be obtained from the ONT/OsBp platform for a specific probe was not tested here, primarily because probe concentration is a known quantity. Most importantly, identification of the target is based on a nanopore profile that exhibits an insignificant number of counts, comparable to the counts of the control/buffer experiment. The main reason we tested every probe by nanopore, is because we wanted to compare different probe designs and confirm high detectability and high sensitivity. The potential of the ONT/OsBp nanopore platform The above experiments range in probe load from 0.38 nmole to 0.9 amole, practically spanning 9 orders of magnitude. In this range evidence is presented for probe detection, and clear distinction between the sample that contains the target and the sample that doesn't. A lower detectability limit is proposed as 3-times higher count of events with probe alone compared to the counts of the hybrid. Proportionality between the count of events and the probe concentration was not tested here, as the duration of the experiments remains in the range of 1 to 3 h and does not reflect the sample load variation. Since our test does not detect the hybrid and therefore does not measure the hybrid molecules, quantification of the target depends on the known probe load. The test requires an estimate for target load and depending on the outcome of the first experiment, one can vary the probe load by a factor of 5 below or above in the next experiment. It is estimated that in certain aspects, target quantification can be attained with about 30% accuracy. A number of representative probe designs were explored and one design proposed that can practically match any ssDNA or ssRNA oligo target. This type of probe, with examples identified as 140EXT(mU) and 21EXT(mU), exhibited high sensitivity at the amole load level. No attempt was made to test for specificity. Discrimination between one target and another target with similar sequence will need to be addressed case-by-case. The HPLC method developed here can evaluate hybridization between a target and a tentative probe and it can also assess probe hybridization extent and tentative discrimination between two targets with similar sequence. Here the flow cell temperature was at the factory preset temperature, but nanopore proteins are known to be stable in a certain temperature range. Flow cell temperature, if left at the discretion of the user, can provide a means to improve specificity. We also did not replace the proprietary ONT Flush buffer. The latter was developed for sequencing, and a different buffer may be developed to be more suitable for other applications including the present invention.

Preliminary experiments indicated that the hybrid of miRNA21 with dmiR21(OMe) is relatively stable in a 15%-85% serum-ONT buffer and that probe 122EXT is detectable by nanopore in a 15%-85% serum-ONT buffer. These experiments suggest that using the ONT/OsBp nanopore platform with blood serum samples is feasible. Considering that the MinION flow cell uses 75 µL sample volume and 15% could be blood serum, then approximately 11 µL of a human serum sample can be directly tested in a nanopore experiment. Assuming that an 11 µL human serum sample contains about 3 amole of miRNA21, miRNA140, or tentatively any other miRNA, a probe designed according the present invention should be able to detect it, and as a corollary detect the presence/absence of the target. In this context, aspects of the invention qualify as a follow-up, point-of-care diagnostic test.

The breadth and scope of the present disclosure should not be limited by any of the above-described exemplary embodiments, but should be defined only in accordance with the following claims and their equivalents.

REFERENCES

1. Bronkhorst, A. J., Ungerer. V., & Holdenrieder, S. Early detection of cancer using circulating tumor DNA: biological, physiological and analytical considerations. Critical Reviews in Clinical Laboratory Sciences, 1-17. Advance online publication. https://doi.org/10.1080/10408363.2019.1700902 (2019).
2. Vidal, J., Taus, A., & Montagut, C. Dynamic treatment stratification using ctDNA. Recent results in cancer research, 215, 263-273, https://doi.org/10.1007/978-3-030-26439-0_14 (2020).
3. Pös, O., Biró, O., Szemes, T., & Nagy, B. Circulating cell-free nucleic acids: characteristics and applications. European Journal of Human Genetics: EJHG, 26(7), 937-945, https://doi.org/10.1038/s41431-018-0132-4 (2018).
4. Oellerich, M., Schütz, E., Beck, J., & Walson, P. D. Circulating cell-free DNA-diagnostic and prognostic applications in personalized cancer therapy. Therapeutic Drug Monitoring, 41(2), 115-120, https://doi.org/10.1097/FTD.0000000000000566 (2019).
5. Stewart, C. M., & Tsui, D. Circulating cell-free DNA for non-invasive cancer management. Cancer Genetics, 228-229, 169-179, https://doi.org/10.1016/j.cancergen.2018.02.005 (2018).
6. Giannopoulou, L., Kasimir-Bauer, S., & Lianidou, E. S. Liquid biopsy in ovarian cancer: recent advances on circulating tumor cells and circulating tumor DNA, Clinical Chemistry and Laboratory Medicine (CCLM), 56(2), 186-197, https://doi.org/10.1515/cclm-2017-0019 (2018).
7. Satyal, U., Srivastava, A., & Abbosh, P. H. Urine biopsy-liquid gold for molecular detection and surveillance of bladder cancer. Frontiers in Oncology, 9, 1266, https://doi.org/10.3389/fonc.2019.01266 (2019).
8. Finotti, A. et al. Liquid biopsy and PCR-free ultrasensitive detection systems in oncology (Review). International Journal of Oncology, 53(4), 1395-1434, https://doi.org/10.3892/ijo.2018.4516 (2018).
9. Valpione, S., & Campana, L. Detection of circulating tumor DNA (ctDNA) by digital droplet polymerase chain reaction (dd-PCR) in liquid biopsies. Methods in Enzymology, 629, 1-15, https://doi.org/10.1016/bs.mie.2019.08.002 (2019).
10. Kwapisz D. The first liquid biopsy test approved. Is it a new era of mutation testing for non-small cell lung cancer? Annals of Translational Medicine, 5(3). 46, https://doi.org/10.21037/atm.2017.01.32 (2017).
11. Kim H K, Yeom J H, Kay M A. Transfer RNA-Derived Small RNAs: Another Layer of Gene Regulation and Novel Targets for Disease Therapeutics. Mol Ther. 2020 Sep. 6:S1525-0016(20)30470-6. doi: 10.1016/j.ymthe.2020.09.013. Epub ahead of print. PMID: 32956625.
12. Poller W. et. al. Non-coding RNAs in cardiovascular diseases: diagnostic and therapeutic perspectives. Eur Heart J. 2018 Aug. 1; 39(29):2704-2716. doi: 10.1093/eurheartj/ehx165. PMID: 28430919; PMCID: PMC6454570.
13. Mitchell, P. et al. Circulating microRNAs as stable blood-based markers for cancer detection. Proceedings of the National Academy of Sciences of the United States of America, 105, 30, 10513-10518, https://doi.org/10.1073/pnas.0804549105 (2008).
14. Aggarwal, V., Priyanka, K., & Tuli, H. S. Emergence of circulating microRNAs in breast cancer as diagnostic and therapeutic efficacy biomarkers. Molecular diagnosis & therapy, 24(2), 153-173, https://doi.org/10.1007/s40291-020-00447-w (2020).
15. Meseure, D., Drak Alsibai, K., Nicolas. A., Bieche, 1. & Morillon, A. Long noncoding RNAs as new architects in cancer epigenetics, prognostic biomarkers, and potential therapeutic targets. Biomed Res Int., 320214, https://doi.org/10.1155/2015/320214 (2015).
16. Ambros, V. MicroRNAs: tiny regulators with great potential. Cell, 107, 823-826, (2001).
17. Bartel, D. P. MicroRNAs: genomics, biogenesis, mechanism, and function. Cell, 116, 281-297 (2004).
18. Mail, C., Rocke, D. M., Durbin-Johnson, B., & Weiss, R. H. Stability of miRNA in human urine supports its biomarker potential. Biomarkers in Medicine, 7(4), 623-631, https://doi.org/10.2217/bmm.13.44 (2013).
19. Alles J. et al. An estimate of the total number of true human miRNAs. Nucleic Acids Research, 47(7), 3353-3364, https://doi.org/10.1093/nar/gkz097 (2019).
20. See in Wikipedia under microRNA/disease.
21. Farazi, T. A., Hoell, J. I., Morozov, P., & Tuschl, T. MicroRNAs in human cancer. Advances in Experimental Medicine and Biology, 774, 1-20, https://doi.org/10.1007/978-94-007-5590-1_1 (2013).
22. Pogribny, 1. P. MicroRNAs as biomarkers for clinical studies. Experimental Biology and Medicine, 243(3), 283-290, http://doi.org/10.1177/1535370217731291 (2017).
23. Rupaimoole, R. & Slack, F. J. MicroRNA therapeutics: towards a new era for the management of cancer and other diseases. Nat Rev Drug Discov, 16(3), 203-222, https://doi.org/10.1038/nrd.2016.246 (2017).
24. Raabe, C., Tang T., Brosius J., & Rozhdestvensky, T. Biases in small RNA deep sequencing data. Nucleic Acids Research, 42(3), 1414-1426, https://doi.org/10.1093/nar/gkt1021 (2014).
25. Ferracin, M., & Negrini, M. Quantification of circulating microRNAs by droplet digital PCR. Methods in Molecular Biology (Clifton, N.J.), 1768, 445-457, https://doi.org/10.1007/978-1-4939-7778-9_25 (2018).
26. Valihrach, L., Androvic, P., & Kubista, M. Circulating miRNA analysis for cancer diagnostics and therapy. Molecular Aspects of Medicine, 72, 100825, https://doi.org/10.1016/j.mam.2019.10.002 (2020).
27. Gines, G., Menezes, R., Xiao, W., Rondelez, Y., Taly, V. Emerging isothermal amplification technologies for microRNA biosensing: applications to liquid biopsies. Molecular Aspects of Medicine, 72, 100832, https://doi.org/10.1016/j.mam.2019.11.002 (2020).
28. Kasianowicz, J. J., Brandin, E., Branton, D. & Deamer, D. W. Characterization of individual polynucleotide molecules using a membrane channel. Proc Natl Acad Sci USA, 93, 13770-13773, (1996).
29. Butler, T. Z., Gundlach, J. H. & Troll, M. Ionic current blockades from DNA and RNA molecules in the alpha-hemolysin nanopore. Biophys J. 93, 3229-3240, https://doi.org/10.1529/biophysj.107.107003 (2007).
30. Maglia, G., Heron, A. J., Stoddart, D., Japrung, D. & Bayley, H. Analysis of single nucleic acid molecules with protein nanopores. Methods Enzymol. 475, 591-623, https://doi.org/10.1016/S0076-6879(10)75022-9 (2010).
31. Haque, F., Li, J., Wu, H. C., Liang, X. J. & Guo, P. Solid-state and biological nanopore for real-time sensing of single chemical and sequencing of DNA. Nano Today, 8, 56-74, https://doi.org/10.1016/j.nantod.2012.12.008 (2013).
32. Fuller C. W. et al. Real-time single-molecule electronic DNA sequencing by synthesis using polymer-tagged nucleotides on a nanopore array. Proc Natl Acad Sci USA, 113(19), 5233-5238, https://doi.org/10.1073/pnas.1601782113 (2016).
33. Laszlo, A. H. et al. Decoding long nanopore sequencing reads of natural DNA. National Biotechnology, 32, 829-833, https://doi.org/10.1038/nbt.2950 (2014).
34. Oxford Nanopore Technologies website: nanoporetech.com, under Resources/Publications.
35. Cao, B. et al. Structure of the nonameric bacterial amyloid secretion channel. Proc Natl Acad Sci USA, 111(50) E5439-E5444, https://doi.org/10.1073/pnas.1411942111 (2014).
36. Chen, X., Wang, L., & Lou, J. Nanotechnology strategies for the analysis of circulating tumor DNA: a review. Med Sci Monit, 26, e921040. https://doi.org/10.12659/MSM.921040 (2020).
37. Chaudhary, V., Jangra, S. & Yadav, N. R. Nanotechnology based approaches for detection and delivery of microRNA in healthcare and crop protection. J Nanobiotechnol, 16, 40, https://doi.org/10.1186/s12951-018-0368-8 (2018).
38. Wanunu M, Dadosh T, Ray V, Jin J, McReynolds L, Drndić M. Rapid electronic detection of probe-specific microRNAs using thin nanopore sensors. Nat Nanotechnol, 2010; 5(11):807-814, https://doi.org/10.1038/nnano.2010.202 (2010).
39. Gu, L. Q. & Wang Y. Nanopore single-molecule detection of circulating microRNAs. Methods Mol Bio, 1024, 255-68. https://doi.org/10.1007/978-1-62703-453-1_21 (2013).
40. Arata, H., Hosokawa, K., & Maeda, M. Rapid sub-attomole microRNA detection on a portable microfluidic chip. Anal Sci, 30(1), 129-135, https://doi.org/10.2116/analsci.30.129 (2014).
41. Henley, R. Y., Vazquez-Pagan, A. G., Johnson, M., Kanavarioti, A. & Wanunu, M. Osmium-based pyrimidine contrast tags for enhanced nanopore-based DNA base discrimination. PLOS One, 10(12), c0142155, https://doi.org/10.1371/journal.pone.0142155 (2015).
42. Xi, D. et al. Nanopore-based selective discrimination of microRNAs with single-nucleotide difference using locked nucleic acid-modified probes. Anal. Chem, 88, 10540-10546, https://doi.org/10.1021/acs.analchem.6b02620 (2016).
43. Zahid, O. K., Wang, F., Ruzicka, J. A., Taylor, E. W. & Hall, A. R. Sequence-specific recognition of microRNAs and other short nucleic acids with solid-state nanopores. Nano Lett, 16(3), 2033-2039, https://doi.org/10.1021-acs.nanolett.6b00001 (2016).
44. Ding, Y. & Kanavarioti, A. Single pyrimidine discrimination during voltage-driven translocation of osmylated oligodeoxynucleotides via the α-hemolysin nanopore. Beilstein J Nanotechnol, 7, 91-101, https://doi.org/10.3762/bjnano.7.11 (2016).
45. Tian, K., Shi, R., Gu, A., Pennella, M., & Gu, L. Q. Polycationic probe-guided nanopore single-molecule counter for selective miRNA detection. Methods in molecular biology (Clifton, N.J.), 1632, 255-268, https://doi.org/10.1007/978-1-4939-7138-1_17 (2017).
46. Zhang, Y., Rana. A., Stratton, Y., Czyzyk-Krzeska. M. F., & Esfandiari. L. (2017). Sequence-Specific Detection of MicroRNAs Related to Clear Cell Renal Cell Carcinoma at fM Concentration by an Electroosmotically Driven Nanopore-Based Device. Analytical Chemistry, 89(17), 9201-9208. https://doi.org/10.1021/acs.analchem.7b01944.
47. Huang. G., Willems, K., Soskine, M., Wloka, C. & Maglia, G. Electro-osmotic capture and ionic discrimination of peptide and protein biomarkers with FraC nanopores. Nature Communications, 8(1), 935, https://doi.org/10.103/s41467-017-01006-4 (2017).
48. Galenkamp, N. S., Soskine. M., Hermans, J., Wloka, C. & Maglia, G. Direct electrical quantification of glucose and asparagine from bodily fluids using nanopores. Nature Communications, 9(1) https://doi.org/10.1038/s41467-018-06534-1 (2018).
49. Sultan M., Kanavarioti, A. Nanopore device-based fingerprinting of RNA oligos and microRNAs enhanced with an osmium tag. Sci Rep, 9(1):14180. https://doi.org/10.1038/s41598-019-50459-8 (2019).
50. Cao, C. et al. Single-molecule sensing of peptides and nucleic acids by engineered aerolysin nanopores. Nature Communications, 10, 4918, https://doi.org/10.1038/s41467-019-12690-9 (2019).
51. Hao, W., Haoran T., Cheng Y., & Yongxin, L. Selective single molecule nanopore sensing of microRNA using PNA functionalized magnetic core—shell Fe3 O4—Au nanoparticles. Analytical Chemistry, 91(12), 7%5-7970, https://doi.org/10.1021/acs.analchem.9b02025 (2019).
52. Workman, R. E. et al. Nanopore native RNA sequencing of a human poly(A) transcriptome. Nat Methods. 16(12): 1297-1305. https://doi.org/10.1038/s41592-019-0617-2 (2019).

53. Wilson, B. D., Eisenstein. M. & Soh, H. T. High-fidelity nanopore sequencing of ultra-short DNA targets. Anal. Chem, 91, 6783-6789, https://doi.org/10.1021/acs.analchem.9b00856 (2019).
54. Kanavarioti, A. Osmylated DNA, a novel concept for sequencing DNA using nanopores. Nanotechnology 26, 134003, https://doi.org/10.1088/0957-4484/26/13/134003 (2015).
55. Chang, C. H., Beer, M. & Marzilli, L. G. Osmium-labeled polynucleotides. The reaction of osmium tetroxide with deoxyribonucleic acids and synthetic polynucleotides in the presence of tertiary nitrogen donor ligands. Biochem, 16(1), 33-38 (1977).
56. Palecek E. Probing DNA structure with osmium tetroxide complexes in vitro. Methods in Enzymology, 212, 139-155, https://www.ncbi.nlm.nih.gov/pubmed/1518446 (1992).
57. Reske T., Surkus, A-E., Duwensee, H. & Flechsig G.-U. Kinetics of the labeling reactions of thymidine, cytosine and uracil with osmium tetroxide bipyridine. Microchimica Acta, 166(3-4), 197-201, https://doi.org/10.1007/s00604-009-0195-6 (2009).
58. Kanavarioti, A. et al. Capillary electrophoretic separation-based approach to determine the labeling kinetics of oligodeoxynucleotides. Electrophoresis, 33, 3529-3543, https://doi.org/10.1002/elps.201200214 (2012).
59. Kanavarioti, A. False positives and false negatives measure less than 0.001% in labeling ssDNA with osmium tetroxide 2,2'-bipyridine. Beilstein J Nanotechnol, 7, 1434-1446, https://doi.org/10.3762/bjnano.7.135 (2016).
60. Debnath, T. K. & Okamoto, A. Osmium tag for post-transcriptionally modified RNA. ChemBioChem, 19, 1653-1656, https://doi.org/10.1002/cbic.201800274 (2018).
61. Kanavarioti, A. HPLC methods for purity evaluation of man-made single-stranded RNAs. Sci Rep, 9(1), 1019, https://doi.org/10.1038/s41598-018-37642-z (2019).
62. Kanavarioti, A., & Kang, A. See RNA(OsBp) event detection Python package in a public repository: https://github.com/kangaroo96/osbp_detect and for step-by-step installation instructions see here: https://github.com/kangaroo96/osbp_detect/blob/master/instructions.md.
63. Majlessi, M., Nelson N. C. & Becker, M. M. Advantages of 2'-O-methyl oligoribonucleotide probes for detecting RNA targets. Nucleic Acids Res, 26, 2224-2229 (1998).
64. Li, X-D. et al. Elevated plasma miRNA-122, -140-3p, -720, -2861, and -3149 during early period of acute coronary syndrome are derived from peripheral blood mononuclear cells. PLoS ONE, 12(9), e0184256, https://doi.org/10.1371/journal.pone.0184256 (2017).
65. Thum. T. et al. MicroRNA-21 contributes to myocardial disease by stimulating MAP kinase signaling in fibroblasts. Nature, 456, 7224, 980-984, https://doi.org/10.1038/nature07511 (2008).
66. Lai, J. Y. et al. MicroRNA-21 in glomerular injury. Journal of the American Society of Nephrology: JASN, 26, 4, 805-816, https-//doi.org/10.1681/ASN.2013121274 (2015).
67. Kao, H. et al. Urine miR-21-5p as a potential non-invasive biomarker for gastric cancer. Oncotarget, 8, 34, 56389-56397, https://doi.org:10.18632/oncotarget.16916 (2017).
68. Fulci. V. et al. Quantitative technologies establish a novel microRNA profile of chronic lymphocytic leukemia. Blood, 109, 11, 4944-51, https://doi.org/10.1182/blood-2006-12-062398 (2007).
69. Wang, Y. et al. Circulating miRNA-21 as a diagnostic biomarker in elderly patients with type 2 cardiorenal syndrome. Sci Rep, 10, 4894, https://doi.org/10.1038/s41598-020-61836-z (2020).
70. MSDS and Information is obtained from the following link to UCLA Chemistry Department, see https://www-.chemistry.ucla.edu/sites/default/files/safety/sopSOP_Osmium_Tetroxide.pdf

---

What is claimed is:

1. An osmylated single-stranded oligonucleotide probe molecule for use in detecting a target nucleic acid molecule, the osmylated-probe comprising at least one thymidine (T) residue covalently bonded to an Osmium tetroxide (OsO$_4$)-2,2'-bypyridine group (OsBp group) and comprising a sequence that is at least partially complementary to the sequence of the target nucleic acid molecule sufficient to create a hybridized double-stranded complex:

(i) wherein the osmylated probe comprises at least three adjacent thymidine (T) residues located at the 5'-end of the probe or wherein the osmylated probe comprises at least three adjacent thymidine (T) residues located at the 3'-end of the probe, wherein one or more of said 5'-end or 3'-end adjacent T residues does not hybridize to the target nucleic acid molecule;

(ii) wherein T residues in the probe sequence, other than the adjacent T residues located at the 5'-end or the 3'-end of the probe, are replaced in the probe molecule by uridine (U), 2'-OMe-Uridine (mU), or deoxyuridine (dU); and (iii) wherein the osmylated probe further comprises one, two, three, four, five, or six adenosine residues (dA or A) at the 5'-end of the probe or at the 3'-end of the probe, wherein one or more of said 5'-end or 3'-end adenosine residues (dA or A) does not hybridize to the target nucleic acid molecule.

2. The osmylated single-stranded oligonucleotide probe molecule of claim 1, wherein the osmylated probe has a length of about 12 to 50 nucleotides.

3. The osmylated single-stranded oligonucleotide probe molecule of claim 1, wherein the probe is a DNA oligonucleotide probe.

4. The osmylated single-stranded oligonucleotide probe molecule of claim 3, wherein at least one of the sugars in the nucleic acid backbone of the oligonucleotide probe is 2'-OMe-substituted.

5. The osmylated single-stranded oligonucleotide probe molecule of claim 1, wherein the probe is an RNA oligonucleotide probe.

6. The osmylated single-stranded oligonucleotide probe molecule of claim 5, wherein at least one of the sugars in the nucleic acid backbone of the oligonucleotide probe is 2'-OMe-substituted.

7. The osmylated single-stranded oligonucleotide probe molecule of claim 1,
wherein none of said 5'-end or 3'-end adjacent T residues hybridizes to the target nucleic acid molecule; and/or
wherein none of said 5'-end or 3'-end dA or A residues hybridizes to the target nucleic acid molecule.

8. The osmylated probe of claim 1, wherein the probe is prepared by reacting an aqueous solution comprising $OsO_4$ and a substituted or unsubstituted 2,2'-bipyridine (osmylating reagent) with an oligonucleotide probe to form the $OsO_4$-2,2'-bipyridine-conjugated probe, and purifying the conjugated probe from excess osmylating reagent.

9. The osmylated probe of claim 1, wherein the probe is prepared by ligation of a (dT(OsBp))n oligo to the 5'-end or 3'-end of the probe, wherein n is 2, 3, or 4.

10. A kit comprising the osmylated single-stranded oligonucleotide probe molecule of claim 1 and a control target nucleic acid molecule that can hybridize to the probe.

11. The osmylated single-stranded oligonucleotide probe molecule of claim 1, further:

(iii) wherein at least 95% of the adjacent T residues located at the 5'-end or the 3'-end of the probe are covalently bonded to an Osmium tetroxide $(OsO_4)$-2,2'-bypyridine group (OsBp group); and (iv) wherein not more than 10% of the pyrimidine residues, other than the adjacent T residues located at the 5'-end or the 3'-end of the probe are covalently bonded to an OsBp group.

12. The osmylated single-stranded oligonucleotide probe molecule of claim 11, wherein the osmylated probe has a length of about 12 to 50 nucleotides.

13. The osmylated single-stranded oligonucleotide probe molecule of claim 11, wherein the probe is a DNA oligonucleotide probe.

14. The osmylated single-stranded oligonucleotide probe molecule of claim 13, wherein at least one of the sugars in the nucleic acid backbone of the oligonucleotide probe is 2'-OMe-substituted.

15. The osmylated single-stranded oligonucleotide probe molecule of claim 11, wherein the probe is an RNA oligonucleotide probe.

16. The osmylated single-stranded oligonucleotide probe molecule of claim 15, wherein at least one of the sugars in the nucleic acid backbone of the oligonucleotide probe is 2'-OMe-substituted.

17. The osmylated single-stranded oligonucleotide probe molecule of claim 11,
wherein none of said 5'-end or 3'-end adjacent T residues hybridizes to the target nucleic acid molecule; and/or
wherein none of said 5'-end or 3'-end dA or A residues hybridizes to the target nucleic acid molecule.

18. The osmylated single-stranded oligonucleotide probe molecule of claim 11, wherein the probe is prepared by reacting an aqueous solution comprising $OsO_4$ and a substituted or unsubstituted 2,2'-bipyridine (osmylating reagent) with an oligonucleotide probe to form the $OsO_4$-2,2'-bipyridine-conjugated probe, and purifying the conjugated probe from excess osmylating reagent.

19. The osmylated single-stranded oligonucleotide probe molecule of claim 11, wherein the probe is prepared by ligation of a $(dT(OsBp))_n$ oligo to the 5'-end or 3'-end of the probe, wherein n is 2, 3, or 4.

20. A kit comprising the osmylated single-stranded oligonucleotide probe molecule of claim 11, and a control target nucleic acid molecule that can hybridize to the probe.

* * * * *

SEQUENCE LISTING

```
Sequence total quantity: 36
SEQ ID NO: 1            moltype = DNA  length = 17
FEATURE                 Location/Qualifiers
source                  1..17
                        mol_type = other DNA
                        organism = synthetic construct
                        note = Synthetic
SEQUENCE: 1
gtaaaacgac ggccagt                                                    17

SEQ ID NO: 2            moltype = DNA  length = 24
FEATURE                 Location/Qualifiers
source                  1..24
                        mol_type = other DNA
                        organism = synthetic construct
                        note = Synthetic
SEQUENCE: 2
cgccagggtt ttcccagtca cgac                                            24

SEQ ID NO: 3            moltype = DNA  length = 17
FEATURE                 Location/Qualifiers
source                  1..17
                        mol_type = other DNA
                        organism = synthetic construct
                        note = Synthetic
SEQUENCE: 3
caggaaacag ctatgac                                                    17
```

-continued

```
SEQ ID NO: 4              moltype = DNA   length = 23
FEATURE                   Location/Qualifiers
source                    1..23
                          mol_type = other DNA
                          organism = synthetic construct
                          note = Synthetic
SEQUENCE: 4
agcggataac aatttcacac agg                                           23

SEQ ID NO: 5              moltype = DNA   length = 35
FEATURE                   Location/Qualifiers
source                    1..35
                          mol_type = other DNA
                          organism = synthetic construct
                          note = Synthetic
SEQUENCE: 5
ttggcactgg ccgtcgtttt acaacgtcgt gactg                              35

SEQ ID NO: 6              moltype = DNA   length = 30
FEATURE                   Location/Qualifiers
source                    1..30
                          mol_type = other DNA
                          organism = synthetic construct
                          note = Synthetic
SEQUENCE: 6
cagtcacgac gttgtaaaac gacggccagt                                    30

SEQ ID NO: 7              moltype = DNA   length = 23
FEATURE                   Location/Qualifiers
source                    1..23
                          mol_type = other DNA
                          organism = synthetic construct
                          note = Synthetic
modified_base             5
                          mod_base = OTHER
                          note = 2'-O-methyluridine
modified_base             20
                          mod_base = OTHER
                          note = 2'-O-methyluridine
misc_feature              1..4
                          note = DNA
misc_feature              5
                          note = RNA
misc_feature              6..19
                          note = DNA
misc_feature              20
                          note = RNA
misc_feature              21..23
                          note = DNA
SEQUENCE: 7
tttgtaaaac gacggccagt aaa                                           23

SEQ ID NO: 8              moltype = DNA   length = 35
FEATURE                   Location/Qualifiers
source                    1..35
                          mol_type = other DNA
                          organism = synthetic construct
                          note = Synthetic
SEQUENCE: 8
acaacgtcgt gactgggaaa accctggcgt taccc                              35

SEQ ID NO: 9              moltype = DNA   length = 30
FEATURE                   Location/Qualifiers
source                    1..30
                          mol_type = other DNA
                          organism = synthetic construct
                          note = Synthetic
SEQUENCE: 9
gggtaacgcc agggttttcc cagtcacgac                                    30

SEQ ID NO: 10             moltype = DNA   length = 30
FEATURE                   Location/Qualifiers
source                    1..30
                          mol_type = other DNA
                          organism = synthetic construct
                          note = Synthetic
```

```
SEQUENCE: 10
gggtaacgcc agggtttccc cagtcacgac                                              30

SEQ ID NO: 11              moltype = DNA   length = 30
FEATURE                    Location/Qualifiers
source                     1..30
                           mol_type = other DNA
                           organism = synthetic construct
                           note = Synthetic
SEQUENCE: 11
gggtaacgcc agggttttc cagtcacgac                                               30

SEQ ID NO: 12              moltype = DNA   length = 30
FEATURE                    Location/Qualifiers
source                     1..30
                           mol_type = other DNA
                           organism = synthetic construct
                           note = Synthetic
modified_base              4
                           mod_base = OTHER
                           note = 2'-O-methylcytidine
modified_base              5
                           mod_base = OTHER
                           note = 2'-O-methylguanosine
modified_base              6
                           mod_base = OTHER
                           note = 2'-O-methylcytidine
modified_base              7
                           mod_base = OTHER
                           note = 2'-O-methylcytidine
modified_base              8
                           mod_base = OTHER
                           note = 2'-O-methyladenosine
modified_base              9
                           mod_base = OTHER
                           note = 2'-O-methylguanosine
modified_base              10
                           mod_base = OTHER
                           note = 2'-O-methylguanosine
modified_base              11
                           mod_base = OTHER
                           note = 2'-O-methylguanosine
modified_base              12
                           mod_base = OTHER
                           note = 2'-O-methyluridine
modified_base              13
                           mod_base = OTHER
                           note = 2'-O-methyluridine
modified_base              14
                           mod_base = OTHER
                           note = 2'-O-methyluridine
modified_base              15
                           mod_base = OTHER
                           note = 2'-O-methyluridine
modified_base              16
                           mod_base = OTHER
                           note = 2'-O-methylcytidine
modified_base              17
                           mod_base = OTHER
                           note = 2'-O-methylcytidine
modified_base              18
                           mod_base = OTHER
                           note = 2'-O-methylcytidine
modified_base              19
                           mod_base = OTHER
                           note = 2'-O-methyladenosine
modified_base              20
                           mod_base = OTHER
                           note = 2'-O-methylguanosine
modified_base              21
                           mod_base = OTHER
                           note = 2'-O-methyluridine
modified_base              22
                           mod_base = OTHER
                           note = 2'-O-methylcytidine
modified_base              23
                           mod_base = OTHER
                           note = 2'-O-methyladenosine
```

| | | |
|---|---|---|
| modified_base | 24 | |
| | mod_base = OTHER | |
| | note = 2'-O-methylcytidine | |
| modified_base | 25 | |
| | mod_base = OTHER | |
| | note = 2'-O-methylguanosine | |
| modified_base | 26 | |
| | mod_base = OTHER | |
| | note = 2'-O-methyladenosine | |
| modified_base | 27 | |
| | mod_base = OTHER | |
| | note = 2'-O-methylcytidine | |
| modified_base | 28 | |
| | mod_base = OTHER | |
| | note = 2'-O-methyladenosine | |
| modified_base | 29 | |
| | mod_base = OTHER | |
| | note = 2'-O-methyladenosine | |
| modified_base | 30 | |
| | mod_base = OTHER | |
| | note = 2'-O-methyladenosine | |
| misc_feature | 1..3 | |
| | note = DNA | |
| misc_feature | 4..30 | |
| | note = RNA | |
| SEQUENCE: 12 | | |
| tttcgccagg gttttcccag tcacgacaaa | | 30 |
| SEQ ID NO: 13 | moltype = DNA  length = 30 | |
| FEATURE | Location/Qualifiers | |
| source | 1..30 | |
| | mol_type = other DNA | |
| | organism = synthetic construct | |
| | note = Synthetic | |
| modified_base | 1 | |
| | mod_base = OTHER | |
| | note = 2'-O-methyladenosine | |
| modified_base | 2 | |
| | mod_base = OTHER | |
| | note = 2'-O-methyladenosine | |
| modified_base | 3 | |
| | mod_base = OTHER | |
| | note = 2'-O-methyladenosine | |
| modified_base | 4 | |
| | mod_base = OTHER | |
| | note = 2'-O-methylcytidine | |
| modified_base | 5 | |
| | mod_base = OTHER | |
| | note = 2'-O-methylguanosine | |
| modified_base | 6 | |
| | mod_base = OTHER | |
| | note = 2'-O-methylcytidine | |
| modified_base | 7 | |
| | mod_base = OTHER | |
| | note = 2'-O-methylcytidine | |
| modified_base | 8 | |
| | mod_base = OTHER | |
| | note = 2'-O-methyladenosine | |
| modified_base | 9 | |
| | mod_base = OTHER | |
| | note = 2'-O-methylguanosine | |
| modified_base | 10 | |
| | mod_base = OTHER | |
| | note = 2'-O-methylguanosine | |
| modified_base | 11 | |
| | mod_base = OTHER | |
| | note = 2'-O-methylguanosine | |
| modified_base | 12 | |
| | mod_base = OTHER | |
| | note = 2'-O-methyluridine | |
| modified_base | 13 | |
| | mod_base = OTHER | |
| | note = 2'-O-methyluridine | |
| modified_base | 14 | |
| | mod_base = OTHER | |
| | note = 2'-O-methyluridine | |
| modified_base | 15 | |
| | mod_base = OTHER | |
| | note = 2'-O-methyluridine | |

```
modified_base          16
                       mod_base = OTHER
                       note = 2'-O-methylcytidine
modified_base          17
                       mod_base = OTHER
                       note = 2'-O-methylcytidine
modified_base          18
                       mod_base = OTHER
                       note = 2'-O-methylcytidine
modified_base          19
                       mod_base = OTHER
                       note = 2'-O-methyladenosine
modified_base          20
                       mod_base = OTHER
                       note = 2'-O-methylguanosine
modified_base          21
                       mod_base = OTHER
                       note = 2'-O-methyluridine
modified_base          22
                       mod_base = OTHER
                       note = 2'-O-methylcytidine
modified_base          23
                       mod_base = OTHER
                       note = 2'-O-methyladenosine
modified_base          24
                       mod_base = OTHER
                       note = 2'-O-methylcytidine
modified_base          25
                       mod_base = OTHER
                       note = 2'-O-methylguanosine
modified_base          26
                       mod_base = OTHER
                       note = 2'-O-methyladenosine
modified_base          27
                       mod_base = OTHER
                       note = 2'-O-methylcytidine
misc_feature           1..27
                       note = RNA
misc_feature           28..30
                       note = DNA
SEQUENCE: 13
aaacgccagg gttttcccag tcacgacttt                                30

SEQ ID NO: 14          moltype = DNA  length = 30
FEATURE                Location/Qualifiers
source                 1..30
                       mol_type = other DNA
                       organism = synthetic construct
                       note = Synthetic
modified_base          12
                       mod_base = OTHER
                       note = 2'-O-methyluridine
modified_base          13
                       mod_base = OTHER
                       note = 2'-O-methyluridine
modified_base          14
                       mod_base = OTHER
                       note = 2'-O-methyluridine
modified_base          15
                       mod_base = OTHER
                       note = 2'-O-methyluridine
modified_base          21
                       mod_base = OTHER
                       note = 2'-O-methyluridine
misc_feature           1..11
                       note = DNA
misc_feature           12..15
                       note = RNA
misc_feature           16..20
                       note = DNA
misc_feature           21
                       note = RNA
misc_feature           22..30
                       note = DNA
SEQUENCE: 14
tttcgccagg gttttcccag tcacgacaaa                                30
```

```
SEQ ID NO: 15            moltype = RNA  length = 22
FEATURE                  Location/Qualifiers
source                   1..22
                         mol_type = other RNA
                         organism = synthetic construct
                         note = Synthetic
SEQUENCE: 15
tagcttatca gactgatgtt ga                                              22

SEQ ID NO: 16            moltype = RNA  length = 37
FEATURE                  Location/Qualifiers
source                   1..37
                         mol_type = other RNA
                         organism = synthetic construct
                         note = Synthetic
SEQUENCE: 16
tagcttatca gactgatgtt gaaaaaaaaa aaaaaaa                              37

SEQ ID NO: 17            moltype = RNA  length = 22
FEATURE                  Location/Qualifiers
source                   1..22
                         mol_type = other RNA
                         organism = synthetic construct
                         note = Synthetic
SEQUENCE: 17
tcaacatcag tctgataagc ta                                              22

SEQ ID NO: 18            moltype = DNA  length = 22
FEATURE                  Location/Qualifiers
source                   1..22
                         mol_type = other DNA
                         organism = synthetic construct
                         note = Synthetic
SEQUENCE: 18
tcaacatcag tctgataagc ta                                              22

SEQ ID NO: 19            moltype = DNA  length = 24
FEATURE                  Location/Qualifiers
source                   1..24
                         mol_type = other DNA
                         organism = synthetic construct
                         note = Synthetic
SEQUENCE: 19
tttcaacatc agtctgataa gcta                                            24

SEQ ID NO: 20            moltype = RNA  length = 22
FEATURE                  Location/Qualifiers
source                   1..22
                         mol_type = other RNA
                         organism = synthetic construct
                         note = Synthetic
modified_base            1
                         mod_base = OTHER
                         note = 2'-O-methyluridine
modified_base            2
                         mod_base = OTHER
                         note = 2'-O-methylcytidine
modified_base            3
                         mod_base = OTHER
                         note = 2'-O-methyladenosine
modified_base            4
                         mod_base = OTHER
                         note = 2'-O-methyladenosine
modified_base            5
                         mod_base = OTHER
                         note = 2'-O-methylcytidine
modified_base            6
                         mod_base = OTHER
                         note = 2'-O-methyladenosine
modified_base            7
                         mod_base = OTHER
                         note = 2'-O-methyluridine
modified_base            8
                         mod_base = OTHER
                         note = 2'-O-methylcytidine
modified_base            9
                         mod_base = OTHER
                         note = 2'-O-methyladenosine
```

| | | |
|---|---|---|
| modified_base | 10 | |
| | mod_base = OTHER | |
| | note = 2'-O-methylguanosine | |
| modified_base | 11 | |
| | mod_base = OTHER | |
| | note = 2'-O-methyluridine | |
| modified_base | 12 | |
| | mod_base = OTHER | |
| | note = 2'-O-methylcytidine | |
| modified_base | 13 | |
| | mod_base = OTHER | |
| | note = 2'-O-methyluridine | |
| modified_base | 14 | |
| | mod_base = OTHER | |
| | note = 2'-O-methylguanosine | |
| modified_base | 15 | |
| | mod_base = OTHER | |
| | note = 2'-O-methyladenosine | |
| modified_base | 16 | |
| | mod_base = OTHER | |
| | note = 2'-O-methyluridine | |
| modified_base | 17 | |
| | mod_base = OTHER | |
| | note = 2'-O-methyladenosine | |
| modified_base | 18 | |
| | mod_base = OTHER | |
| | note = 2'-O-methyladenosine | |
| modified_base | 19 | |
| | mod_base = OTHER | |
| | note = 2'-O-methylguanosine | |
| modified_base | 20 | |
| | mod_base = OTHER | |
| | note = 2'-O-methylcytidine | |
| modified_base | 21 | |
| | mod_base = OTHER | |
| | note = 2'-O-methyluridine | |
| modified_base | 22 | |
| | mod_base = OTHER | |
| | note = 2'-O-methyladenosine | |
| SEQUENCE: 20 | | |
| tcaacatcag tctgataagc ta | | 22 |
| | | |
| SEQ ID NO: 21 | moltype = DNA   length = 26 | |
| FEATURE | Location/Qualifiers | |
| source | 1..26 | |
| | mol_type = other DNA | |
| | organism = synthetic construct | |
| | note = Synthetic | |
| modified_base | 9 | |
| | mod_base = OTHER | |
| | note = 2'-O-methyluridine | |
| modified_base | 13 | |
| | mod_base = OTHER | |
| | note = 2'-O-methyluridine | |
| modified_base | 15 | |
| | mod_base = OTHER | |
| | note = 2'-O-methyluridine | |
| modified_base | 18 | |
| | mod_base = OTHER | |
| | note = 2'-O-methyluridine | |
| modified_base | 23 | |
| | mod_base = OTHER | |
| | note = 2'-O-methyluridine | |
| misc_feature | 1..8 | |
| | note = DNA | |
| misc_feature | 9 | |
| | note = RNA | |
| misc_feature | 10..12 | |
| | note = DNA | |
| misc_feature | 13 | |
| | note = RNA | |
| misc_feature | 14 | |
| | note = DNA | |
| misc_feature | 15 | |
| | note = RNA | |
| misc_feature | 16..17 | |
| | note = DNA | |
| misc_feature | 18 | |
| | note = RNA | |

| | |
|---|---|
| misc_feature | 19..22<br>note = DNA |
| misc_feature | 23<br>note = RNA |
| misc_feature | 24..26<br>note = DNA |

SEQUENCE: 21
tttcaacatc agtctgataa gctaaa                                             26

| | |
|---|---|
| SEQ ID NO: 22<br>FEATURE<br>source | moltype = RNA  length = 22<br>Location/Qualifiers<br>1..22<br>mol_type = other RNA<br>organism = synthetic construct<br>note = Synthetic |

SEQUENCE: 22
tggagtgtga caatggtgtt tg                                                 22

| | |
|---|---|
| SEQ ID NO: 23<br>FEATURE<br>source | moltype = RNA  length = 22<br>Location/Qualifiers<br>1..22<br>mol_type = other RNA<br>organism = synthetic construct<br>note = Synthetic |

SEQUENCE: 23
caaacaccat tgtcacactc ca                                                 22

| | |
|---|---|
| SEQ ID NO: 24<br>FEATURE<br>source | moltype = DNA  length = 22<br>Location/Qualifiers<br>1..22<br>mol_type = other DNA<br>organism = synthetic construct<br>note = Synthetic |

SEQUENCE: 24
caaacaccat tgtcacactc ca                                                 22

| | |
|---|---|
| SEQ ID NO: 25<br>FEATURE<br>source | moltype = DNA  length = 44<br>Location/Qualifiers<br>1..44<br>mol_type = other DNA<br>organism = synthetic construct<br>note = Synthetic |

SEQUENCE: 25
caaacaccat tgtcacactc cacaaacacc attgtcacac tcca                         44

| | |
|---|---|
| SEQ ID NO: 26<br>FEATURE<br>source | moltype = DNA  length = 25<br>Location/Qualifiers<br>1..25<br>mol_type = other DNA<br>organism = synthetic construct<br>note = Synthetic |

SEQUENCE: 26
tttcaaacac cattgtcaca ctcca                                              25

| | |
|---|---|
| SEQ ID NO: 27<br>FEATURE<br>source | moltype = RNA  length = 22<br>Location/Qualifiers<br>1..22<br>mol_type = other RNA<br>organism = synthetic construct<br>note = Synthetic |
| modified_base | 1<br>mod_base = OTHER<br>note = 2'-O-methylcytidine |
| modified_base | 2<br>mod_base = OTHER<br>note = 2'-O-methyladenosine |
| modified_base | 3<br>mod_base = OTHER<br>note = 2'-O-methyladenosine |
| modified_base | 4<br>mod_base = OTHER<br>note = 2'-O-methyladenosine |
| modified_base | 5<br>mod_base = OTHER<br>note = 2'-O-methylcytidine |
| modified_base | 6<br>mod_base = OTHER<br>note = 2'-O-methyladenosine |

```
modified_base       7
                    mod_base = OTHER
                    note = 2'-O-methylcytidine
modified_base       8
                    mod_base = OTHER
                    note = 2'-O-methylcytidine
modified_base       9
                    mod_base = OTHER
                    note = 2'-O-methyladenosine
modified_base       10
                    mod_base = OTHER
                    note = 2'-O-methyluridine
modified_base       11
                    mod_base = OTHER
                    note = 2'-O-methyluridine
modified_base       12
                    mod_base = OTHER
                    note = 2'-O-methylguanosine
modified_base       13
                    mod_base = OTHER
                    note = 2'-O-methyluridine
modified_base       14
                    mod_base = OTHER
                    note = 2'-O-methylcytidine
modified_base       15
                    mod_base = OTHER
                    note = 2'-O-methyladenosine
modified_base       16
                    mod_base = OTHER
                    note = 2'-O-methylcytidine
modified_base       17
                    mod_base = OTHER
                    note = 2'-O-methyladenosine
modified_base       18
                    mod_base = OTHER
                    note = 2'-O-methylcytidine
modified_base       19
                    mod_base = OTHER
                    note = 2'-O-methyluridine
modified_base       20
                    mod_base = OTHER
                    note = 2'-O-methylcytidine
modified_base       21
                    mod_base = OTHER
                    note = 2'-O-methylcytidine
modified_base       22
                    mod_base = OTHER
                    note = 2'-O-methyladenosine
SEQUENCE: 27
caaacaccat tgtcacactc ca                                              22

SEQ ID NO: 28       moltype = RNA  length = 22
FEATURE             Location/Qualifiers
source              1..22
                    mol_type = other RNA
                    organism = synthetic construct
                    note = Synthetic
SEQUENCE: 28
cagtggtttt accctatggt ag                                              22

SEQ ID NO: 29       moltype = DNA  length = 22
FEATURE             Location/Qualifiers
source              1..22
                    mol_type = other DNA
                    organism = synthetic construct
                    note = Synthetic
SEQUENCE: 29
ctaccatagg gtaaaaccac tg                                              22

SEQ ID NO: 30       moltype = DNA  length = 44
FEATURE             Location/Qualifiers
source              1..44
                    mol_type = other DNA
                    organism = synthetic construct
                    note = Synthetic
SEQUENCE: 30
ctaccatagg gtaaaaccac tgctaccata gggtaaaacc actg                      44
```

```
SEQ ID NO: 31          moltype = DNA  length = 27
FEATURE                Location/Qualifiers
source                 1..27
                       mol_type = other DNA
                       organism = synthetic construct
                       note = Synthetic
modified_base          5
                       mod_base = OTHER
                       note = 2'-O-methyluridine
modified_base          10
                       mod_base = OTHER
                       note = 2'-O-methyluridine
modified_base          15
                       mod_base = OTHER
                       note = 2'-O-methyluridine
modified_base          24
                       mod_base = OTHER
                       note = 2'-O-methyluridine
misc_feature           1..4
                       note = DNA
misc_feature           5
                       note = RNA
misc_feature           6..9
                       note = DNA
misc_feature           10
                       note = RNA
misc_feature           11..14
                       note = DNA
misc_feature           15
                       note = RNA
misc_feature           16..23
                       note = DNA
misc_feature           24
                       note = RNA
misc_feature           25..27
                       note = DNA
SEQUENCE: 31
tttctaccat agggtaaaac cactgaa                                           27

SEQ ID NO: 32          moltype = DNA  length = 20
FEATURE                Location/Qualifiers
source                 1..20
                       mol_type = other DNA
                       organism = synthetic construct
                       note = Synthetic
SEQUENCE: 32
ctctctctct ctctctctct                                                   20

SEQ ID NO: 33          moltype = RNA  length = 32
FEATURE                Location/Qualifiers
source                 1..32
                       mol_type = other RNA
                       organism = synthetic construct
                       note = Synthetic
SEQUENCE: 33
agagagagcc agagagagcc agagagcctt ca                                     32

SEQ ID NO: 34          moltype = RNA  length = 100
FEATURE                Location/Qualifiers
source                 1..100
                       mol_type = other RNA
                       organism = synthetic construct
                       note = Synthetic
SEQUENCE: 34
ttacagccac gtctacagca gttttagagc tagaaatagc aagttaaaat aaggctagtc       60
cgttatcaac ttgaaaaagt ggcaccgagt cggtgctttt                            100

SEQ ID NO: 35          moltype = RNA  length = 97
FEATURE                Location/Qualifiers
source                 1..97
                       mol_type = other RNA
                       organism = synthetic construct
                       note = Synthetic
modified_base          1
                       mod_base = OTHER
                       note = 2'-O-methyluridine
```

-continued

```
modified_base        2
                     mod_base = OTHER
                     note = 2'-O-methyluridine
modified_base        3
                     mod_base = OTHER
                     note = 2'-O-methyladenosine
modified_base        26
                     mod_base = OTHER
                     note = 2'-O-methylguanosine
modified_base        27
                     mod_base = OTHER
                     note = 2'-O-methylcytidine
modified_base        28
                     mod_base = OTHER
                     note = 2'-O-methyluridine
modified_base        29
                     mod_base = OTHER
                     note = 2'-O-methyladenosine
modified_base        30
                     mod_base = OTHER
                     note = 2'-O-methylguanosine
modified_base        31
                     mod_base = OTHER
                     note = 2'-O-methyladenosine
modified_base        32
                     mod_base = OTHER
                     note = 2'-O-methyladenosine
modified_base        33
                     mod_base = OTHER
                     note = 2'-O-methyladenosine
modified_base        34
                     mod_base = OTHER
                     note = 2'-O-methyluridine
modified_base        35
                     mod_base = OTHER
                     note = 2'-O-methyladenosine
modified_base        36
                     mod_base = OTHER
                     note = 2'-O-methylguanosine
modified_base        37
                     mod_base = OTHER
                     note = 2'-O-methylcytidine
modified_base        66
                     mod_base = OTHER
                     note = 2'-O-methyladenosine
modified_base        67
                     mod_base = OTHER
                     note = 2'-O-methylcytidine
modified_base        68
                     mod_base = OTHER
                     note = 2'-O-methyluridine
modified_base        69
                     mod_base = OTHER
                     note = 2'-O-methyluridine
modified_base        70
                     mod_base = OTHER
                     note = 2'-O-methylguanosine
modified_base        71
                     mod_base = OTHER
                     note = 2'-O-methyladenosine
modified_base        72
                     mod_base = OTHER
                     note = 2'-O-methyladenosine
modified_base        73
                     mod_base = OTHER
                     note = 2'-O-methyladenosine
modified_base        74
                     mod_base = OTHER
                     note = 2'-O-methyladenosine
modified_base        75
                     mod_base = OTHER
                     note = 2'-O-methyladenosine
modified_base        76
                     mod_base = OTHER
                     note = 2'-O-methylguanosine
modified_base        77
                     mod_base = OTHER
                     note = 2'-O-methyluridine
```

```
modified_base      78
                   mod_base = OTHER
                   note = 2'-O-methylguanosine
modified_base      79
                   mod_base = OTHER
                   note = 2'-O-methylguanosine
modified_base      80
                   mod_base = OTHER
                   note = 2'-O-methylcytidine
modified_base      81
                   mod_base = OTHER
                   note = 2'-O-methyladenosine
modified_base      82
                   mod_base = OTHER
                   note = 2'-O-methylcytidine
modified_base      83
                   mod_base = OTHER
                   note = 2'-O-methylcytidine
modified_base      84
                   mod_base = OTHER
                   note = 2'-O-methylguanosine
modified_base      85
                   mod_base = OTHER
                   note = 2'-O-methyladenosine
modified_base      86
                   mod_base = OTHER
                   note = 2'-O-methylguanosine
modified_base      87
                   mod_base = OTHER
                   note = 2'-O-methyluridine
modified_base      88
                   mod_base = OTHER
                   note = 2'-O-methylcytidine
modified_base      89
                   mod_base = OTHER
                   note = 2'-O-methylguanosine
modified_base      90
                   mod_base = OTHER
                   note = 2'-O-methylguanosine
modified_base      91
                   mod_base = OTHER
                   note = 2'-O-methyluridine
modified_base      92
                   mod_base = OTHER
                   note = 2'-O-methylguanosine
modified_base      93
                   mod_base = OTHER
                   note = 2'-O-methylcytidine
modified_base      94
                   mod_base = OTHER
                   note = 2'-O-methyluridine
modified_base      95
                   mod_base = OTHER
                   note = 2'-O-methyluridine
modified_base      96
                   mod_base = OTHER
                   note = 2'-O-methyluridine
modified_base      97
                   mod_base = OTHER
                   note = 2'-O-methyluridine
SEQUENCE: 35
ttacagccac gtctacagtt ttagagctag aaatagcaag ttaaaataag gctagtccgt    60
tatcaacttg aaaaagtggc accgagtcgg tgctttt                             97

SEQ ID NO: 36      moltype = DNA   length = 20
FEATURE            Location/Qualifiers
source             1..20
                   mol_type = other DNA
                   organism = synthetic construct
SEQUENCE: 36
tctctctctc tctctctctc                                                20
```